(12) United States Patent
Munchhof et al.

(10) Patent No.: US 6,492,383 B1
(45) Date of Patent: Dec. 10, 2002

(54) THIENOPYRIMIDINE AND THIENOPYRIDINE DERIVATIVES USEFUL AS ANTICANCER AGENTS

(75) Inventors: Michael John Munchhof, Salem; Susan Beth Sobolov-Jaynes, Ivoryton; Matthew Arnold Marx, Waterford, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/502,129

(22) Filed: Feb. 10, 2000

Related U.S. Application Data

(63) Continuation-in-part of application No. PCT/IB98/01691, filed on Oct. 22, 1998.
(60) Provisional application No. 60/065,097, filed on Nov. 11, 2001, now abandoned.

(51) Int. Cl.[7] ..................... A61K 31/44; A61K 31/517; C07D 239/70; C07D 515/02
(52) U.S. Cl. .................. 514/301; 514/258.1; 544/253; 546/114
(58) Field of Search .................. 514/258.1, 301; 544/253; 546/114

(56) References Cited

U.S. PATENT DOCUMENTS

| 5,187,168 A | 2/1993 | Primeau | 514/259 |
| 5,654,307 A | 8/1997 | Bridges | 514/258 |

FOREIGN PATENT DOCUMENTS

| EP | 0071227 | 11/1987 |
| EP | 0364598 | 4/1990 |
| EP | 0452002 | 10/1991 |
| EP | 0778277 | 6/1997 |
| WO | 9317021 | 9/1993 |
| WO | 9519774 | 7/1995 |
| WO | 9640142 | 12/1996 |
| WO | 9713771 | 4/1997 |
| WO | 9729110 | 8/1997 |
| WO | 9802437 | 1/1998 |
| WO | 9802438 | 1/1998 |
| WO | 9940091 | 8/1999 |

*Primary Examiner*—Mukund J. Shah
*Assistant Examiner*—Tamthom N. Truong
(74) *Attorney, Agent, or Firm*—Peter C. Richardson; Paul H. Ginsburg; Adrian G. Looney

(57) ABSTRACT

The invention relates to compounds of the formulas 1 and 2

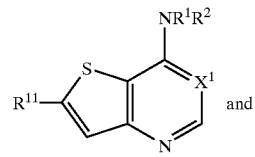

and

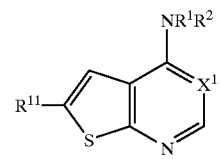

and to pharmaceutically acceptable salts and hydrates thereof, wherein $X^1$, $R^1$, $R^2$ and $R^{11}$ are as defined herein. The invention also relates to pharmaceutical compositions containing the compounds of formulas 1 and 2 and to methods of treating hyperproliferative disorders in a mammal by administering the compounds of formulas 1 and 2.

25 Claims, No Drawings

THIENOPYRIMIDINE AND THIENOPYRIDINE DERIVATIVES USEFUL AS ANTICANCER AGENTS

This application is a continuation-in-part of PCT/IB98/01691, filed Oct. 22, 1998, published May 20, 1999, which claims priority to U.S. Provisional Patent Application Ser. No. 60/065,097, filed Nov. 11, 2001, now abandoned, both of which are herein incorporated by reference in their entirety.

BACKGROUND OF THE INVENTION

This invention relates to novel bicyclic pyrimidine and pyridine derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

Compounds that are useful in the treatment of hyperproliferative diseases are also disclosed in the following co-pending patent applications: PCT international patent application number PCT/IB97100675 (filed Jun. 11, 1997), U.S. provisional patent application No. 601041846 (filed Apr. 9, 1997), U.S. provisional patent application No. 60/031862 (filed Nov. 27, 1996), U.S. provisional patent application No. 60/028881 (filed Oct. 17, 1996), PCT international patent application number PCT/IB97/00584 (filed May 22, 1997), U.S. patent application Ser. No. 08/653,786 (filed May 28, 1996), PCT international patent application publication number WO 96/40142 (published Dec. 19, 1996), PCT international patent application publication number WO 97/13771 (published Apr. 17, 1997), and PCT international patent application publication number WO 95/23141 (published Aug. 31, 1995). Each of the foregoing United States and PCT international patent applications is incorporated herein by reference in its entirety.

It is known that a cell may become cancerous by virtue of the transformation of a portion of its DNA into an oncogene (i.e. a gene that upon activation leads to the formation of malignant tumor cells). Many oncogenes encode proteins which are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes that span the cell membrane and possess an extracellular binding domain for growth factors such as epidermal growth factor, a transmembrane domain, and an intracellular portion that functions as a kinase to phosphorylate specific tyrosine residue in proteins and hence to influence cell proliferation. The foregoing tyrosine kinases may be classified as growth factor receptor (e.g. EGFR, PDGFR, FGFR and erbB2) or non-receptor (e.g. c-src and bcr-abl) kinases. It is known that such kinases are often aberrantly expressed in common human cancers such as breast cancer, gastrointestinal cancer such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers. It has also been shown that epidermal growth factor receptor (EGFR) is mutated or overexpressed in many human cancers such as brain, lung, squamous cell, bladder, gastric, breast, head and neck, oesophageal, gynecological and thyroid cancers. Thus, it is believed that inhibitors of receptor tyrosine kinases, such as the compounds of the present invention, are useful as selective inhibitors of the growth of mammalian cancer cells.

It has also been shown that EGFR inhibitors may be useful in the treatment of pancreatitis and kidney disease (such as proliferative glomerulonephritis and diabetes-induced renal disease), and may reduce successful blastocyte implantation and therefore may be useful as a contraceptive. See PCT international application publication number WO 95/19970 (published Jul. 27, 1995).

It is known that polypeptide growth factors such as vascular endothelial growth factor (VEGF) having a high affinity to the human kinase insert-domain-containing receptor (KDR) or the murine fetal liver kinase 1 (FLK-1) receptor have been associated with the proliferation of endothelial cells and more particularly vasculogenesis and angiogenesis. See PCT international application publication number WO 95/21613 (published Aug. 17, 1995). Agents, such as the compounds of the present invention, that are capable of binding to or modulating the KDR/FLK-1 receptor may be used to treat disorders related to vasculogenesis or angiogenesis such as diabetes, diabetic retinopathy, hemangioma, glioma, melanoma, Kaposi's sarcoma and ovarian, breast, lung, pancreatic, prostate, colon and epidermoid cancer.

SUMMARY OF THE INVENTION

The present invention relates to compounds of the formulas 1 and 2

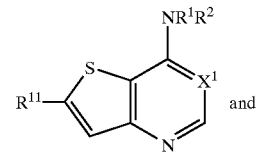 and

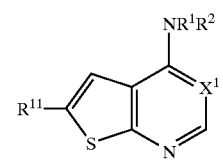

and to pharmaceutically acceptable salts and hydrates thereof, wherein:

wherein $X^1$ is N or CH;

$R^1$ is H, $C_1$–$C_6$ alkyl or —C(O)($C_1$–$C_6$ alkyl);

$R^2$ is $C_6$–$C_{10}$ aryl or 5–13 membered heterocyclic, wherein said $R^2$ groups are optionally substituted by 1 to 5 $R^5$ substituents, each $R^5$ is independently selected from halo, cyano, nitro, trifluoromethoxy, trifluoromethyl, azido, —C(O)$R^8$, —C(O)O$R^8$, —OC(O)$R^8$, —OC(O)O$R^8$, —N$R^6$C(O)$R^7$, —C(O)N$R^6R^7$, —N$R^6R^7$, —O$R^9$, —SO$_2$N$R^6R^7$, $C_1$–$C_6$ alkyl, —(CH$_2$)$_j$O(CH$_2$)$_q$N$R^6R^7$, —(CH$_2$)$_t$O (CH$_2$)$_q$O$R^9$, —(CH$_2$)$_t$O$R^9$, —S(O)$_j$($C_1$–$C_6$ alkyl), —(CH$_2$)$_t$($C_6$–$C_{10}$ aryl), —(CH$_2$)$_t$(5–10 membered heterocyclic); —C(O)(CH$_2$)$_t$($C_6$–$C_{10}$ aryl), —(CH$_2$)$_t$O (CH$_2$)$_j$($C_6$–$C_{10}$ aryl), —(CH$_2$)$_t$O(CH$_2$)$_q$(5–10 membered heterocyclic), —C(O)(CH$_2$)$_t$(5–10 membered heterocyclic), —(CH$_2$)$_j$N$R^7$(CH$_2$)$_q$N$R^6R^7$, —(CH$_2$)$_j$ N$R^7$CH$_2$C(O)N$R^6R^7$, —(CH$_2$)$_j$N$R^7$(CH$_2$)$_q$N$R^9$C(O) $R^8$, —(CH$_2$)$_j$N$R^7$(CH$_2$)$_j$O(CH$_2$)$_q$O$R^9$, —(CH$_2$)$_j$N$R^7$ (CH$_2$)$_q$S(O)$_j$($C_1$–$C_6$ alkyl), —(CH$_2$)$_j$N$R^7$(CH$_2$)$_t$$R^6$, —SO$_2$(CH$_2$)$_t$(C$_6$–C$_{10}$ aryl), and —SO$_2$(CH$_2$)$_t$(5–10 membered heterocyclic), wherein j is an integer ranging from 0 to 2, t is an integer ranging from 0 to 6, q is an integer ranging from 2 to 6, the —(CH$_2$)$_q$— and —(CH$_2$)$_t$— moieties of the foregoing R$^5$ groups optionally include a carbon-carbon double or triple bond where t is an integer between 2 and 6, and the alkyl, aryl and heterocyclic moieties of the foregoing R$^5$ groups are optionally substituted by 1 to 3 substituents independently selected from halo, cyano, nitro, trifluoromethyl, azido, —C(O)R$^8$, —C(O)OR$^8$, —OC(O)R$^8$, —OC(O)OR$^8$, —NR$^6$C(O)R$^7$, —C(O)NR$^6$R$^7$, —(CH$_2$)$_t$NR$^6$R$^7$, C$_1$–C$_6$ alkyl, —(CH$_2$)$_t$(C$_6$–C$_{10}$ aryl), —(CH$_2$)$_t$(5–10 membered heterocyclic), —(CH$_2$)$_t$O(CH$_2$)$_q$OR$^9$, and —(CH$_2$)$_t$OR$^9$, wherein t is an integer ranging from 0 to 6 and q is an integer ranging from 2 to 6;

each R$^6$ and R$^7$ is independently selected from H, C$_1$–C$_6$ alkyl, —(CH$_2$)$_t$(C$_6$–C$_{10}$ aryl), —(CH$_2$)$_t$(5–10 membered heterocyclic), —(CH$_2$)$_t$O(CH$_2$)$_q$OR$^9$, and —(CH$_2$)$_t$OR$^9$, wherein t is an integer ranging from 0 to 6 and q is an integer ranging from 2 to 6, and the alkyl, aryl and heterocyclic moieties of the foregoing R$^6$ and R$^7$ groups are optionally substituted by 1 to 3 substituents independently selected from halo, cyano, nitro, trifluoromethyl, azido, —C(O)R$^8$, —C(O)OR$^8$, —CO(O)R$^8$, —OC(O)OR$^8$, —NR$^9$C(O)R$^{10}$, —C(O)NR$^9$R$^{10}$, —NR$^9$R$^{10}$, C$_1$–C$_6$ alkyl, —(CH$_2$)$_t$(C$_6$–C$_{10}$ aryl), —(CH$_2$)$_t$(5–10 membered heterocyclic), —(CH$_2$)$_t$O(CH$_2$)$_q$OR$^9$, and —(CH$_2$)$_t$OR$^9$, wherein t is an integer ranging from 0 to 6 and q is an integer ranging from 2 to 6, with the proviso that where R$^6$ and R$^7$ are both attached to the same nitrogen, then R$^6$ and R$^7$ are not both bonded to the nitrogen directly through an oxygen;

each R$^8$ is independently selected from H, C$_1$–C$_{10}$ alkyl, —(CH$_2$)$_t$(C$_6$–C$_{10}$ aryl), and —(CH$_2$)$_t$(5–10 membered heterocyclic), wherein t is an integer ranging from 0 to 6;

each R$^9$ and R$^{10}$ is independently selected from H and C$_1$–C$_6$ alkyl; and, R$^{11}$ is H, C$_1$–C$_6$ alkyl, —C(O)NR$^6$R$^9$, —C(O)(C$_6$–C$_{10}$ aryl), —(CH$_2$)$_t$(C$_6$–C$_{10}$ aryl), or —(CH$_2$)$_t$(5–10 membered heterocyclic), wherein t is an integer ranging from 0 to 6, wherein said R$^{11}$ groups, other than H, are optionally substituted by 1 to 5 R$^5$ groups.

Preferred compounds include those of formula 1 wherein R$^{11}$ is —(CH$_2$)$_t$(C$_6$–C$_{10}$ aryl) or —(CH$_2$)$_t$(5–10 membered heterocyclic), wherein t is an integer ranging from 0 to 6, wherein said R$^{11}$ groups are optionally substituted by 1 to 5 R$^5$ groups. Specific preferred R$^{11}$ groups include phenyl or pyridyl, wherein said phenyl and pyridyl are optionally substituted by 1 to 5 R$^5$ groups.

Other preferred compounds include those of formula 1 wherein X$^1$ is CH.

Other preferred compounds include those of formula 1 wherein R$^2$ is phenyl optionally substituted by 1 to 5 R$^5$ substituents, or R$^2$ is a group of the formula

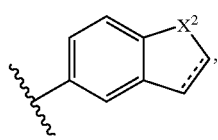
3

-continued

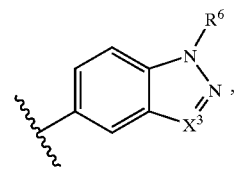
4

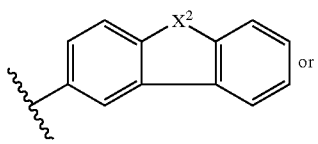
5 or

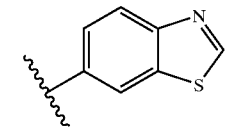
6 wherein X$^2$ is —S— or —N(R$^6$)—, X$^3$ is N or CH, the dashed line in formula 3 represents an optional double bond, and the above R$^2$ groups of formulas 3 and 5 are optionally substituted by 1 to 5 R$^5$ substituents and the R$^2$ groups of formulas 4 and 6 are optionally substituted by 1 to 3 R$^5$ substituents. Specifically preferred compounds include those wherein R$^2$ is a group of formula 3 above wherein said group is optionally substituted by 1 to 5 R$^5$ substituents.

Specific embodiments of the present invention include the following compounds:

(3-Ethynyl-phenyl)-(6-phenyl-thieno[3,2-d]pyrimidin-4-yl)-amine;
(3-Ethynyl-phenyl)-[6-(4-methoxy-phenyl)-thieno[3,2-d]pyrimidin-4-yl]-amine;
Benzo[b]thiophen-5-yl-(6-phenyl-thieno[3,2-d]pyrimidin-4-yl)-amine;
(1H-Indol-5-yl)-[6-(4-methoxy-phenyl)-thieno[3,2-d]pyrimidin-4-yl]-amine;
(1H-Indol-5-yl)-(6-phenyl-thieno[3,2-d]pyrimidin-4-yl)-amine;
(6-Phenyl-thieno[3,2-d]pyrimidin-4-yl)-(2-pyrrol-1-yl-phenyl)-amine;
(5-Phenyl-1H-pyrazol-3-yl)-(6-phenyl-thieno[3,2-d]pyrimidin-4-yl)-amine;
(5-Phenyl-1H-pyrazol-3-yl)-thieno[3,2-d]pyrimidin-4-yl-amine;
(1H-Indol-5-yl)-thieno[3,2-d]pyrimidin-4-yl-amine;
N-(5-Phenyl)-1-(6-phenyl-thieno[3,2-d]pyrimidin-4-yl)-1H-[1,2,4]triazole-3,5-diamine;
3-[3-Phenyl-5-(6-phenyl-thieno[3,2-d]pyrimidin-4-ylamino)-pyrazol-1-yl]-propionitrile;
(5-Furan-2-yl-2H-pyrazol-3-yl)-(6-phenyl-thieno[3,2-d]pyrimidin-4-yl)-amine;;
(6-Phenyl-thieno[3,2-d]pyrimidin-4-yl)-(5-thiophen-2-yl-2H-pyrazol-3-yl)-amine;
N-(6-Phenyl-thieno[3,2-d]pyrimidin-4-yl)-benzene-1,4-diamine;
N-[4-(6-Phenyl-thieno[3,2-d]pyrimidin-4-ylamino)-phenyl]-benzamide;
N-Methyl-N'-(6-phenyl-thieno[3,2-d]pyrimidin-4-yl)-benzene-1,4-diamine;
(1H-Indazol-5-yl)-(6-phenyl-thieno[3,2-d]pyrimidin-4-yl)-amine;
[5-(4-Chloro-phenyl)-2H-pyrazol-3-yl]-(6-phenyl-thieno[3,2-d]pyrimidin-4-yl)-amine;

Benzothiazol-6-yl-(6-phenyl-thieno[3,2-d]pyrimidin-4-yl)-amine;
4-(6-Phenyl-thieno[3,2-d]pyrimidin-4-ylamino)-benzamide;
4-Methyl-N-[4-(6-phenyl-thieno[3,2-d]pyrimidin-4-ylamino)-phenyl]-benzenesulfonamide;
N-Phenyl-N'-(6-phenyl-thieno[3,2-d]pyrimidin-4-yl)-benzene-1,4-diamine;
(6-Phenyl-thieno[3,2-d]pyrimidin-4-yl)-(2H-pyrazol-3-yl)-amine;
(1 H-Indazol-6-yl)-(6-phenyl-thieno[3,2-d]pyrimidin-4-yl)-amine;
N,N-Dimethyl-N'-(6-phenyl-thieno[3,2-d]pyrimidin-4-yl)-benzene-1,4-diamine;
(2,3-Dimethyl-1H-indol-5-yl)-(6-phenyl-thieno[3,2-d]pyrimidin-4-yl)-amine;
N-Ethyl-N'-(6-phenyl-thieno[3,2-d]pyrimidin-4-yl)-benzene-1,4-diamine;
[4-(1H-Indol-5-ylamino)-thieno[3,2-d]pyrimidin-6-yl]-phenyl-methanone;
(1H-Indol-5-yl)-(6-p-tolyl-thieno[3,2-d]pyrimidin-4-yl)-amine;
(5-Furan-2-yl-2H-pyrazol-3-yl)-thieno[3,2-d]pyrimidin-4-yl-amine;
Thieno[3,2-d]pyrimidin-4-yl-(5-thiophen-2-yl-2H-pyrazol-3-yl)-amine;
[5-(4-Chloro-phenyl)-2H-pyrazol-3-yl]-thieno[3,2-d]pyrimidin-4-yl-amine;
(2H-Pyrazol-3-yl)-thieno[3,2-d]pyrimidin-4-yl-amine;
Thieno[3,2-d]pyrimidin-4-yl-(5-p-tolyl-2H-pyrazol-3-yl)-amine;
4-[4-(1H-Indol-5-ylamino)-thieno[3,2-d]pyrimidin-6-yl]-benzaldehyde;
[6-(4-Chloro-phenyl)-thieno[3,2-d]pyrimidin-4-yl]-(1H-indol-5-yl)-amine;
[6-(4-Fluoro-phenyl)-thieno[3,2-d]pyrimidin-4-yl]-(1H-indol-5-yl)-amine;
(1H-Indol-5-yl)(6-thiophen-3-yl-thieno[3,2-d]pyrimidin-4-yl)-amine;
2-[3-(4-Chloro-phenyl)-5-(thieno[3,2-d]pyrimidin-4-ylamino)-pyrazol-1-yl]-ethanol;
(1H-Indol-5-yl)-[6-(4-trifluoromethyl-phenyl)-thieno[3,2-d]pyrimidin-4-yl]-amine;
(1H-Indol-5-yl)-[6-(4-methylsulfanyl-phenyl)-thieno[3,2-d]pyrimidin-4-yl]-amine;
(1H-Indol-5-yl)-[6-(3-nitro-phenyl)-thieno[3,2-d]pyrimidin-4-yl]-amine;,
[6-(3-Chloro-4-fluoro-phenyl)-thieno[3,2-d]pyrimidin-4-yl]-(1H-indol-5-yl)-amine;
[5-(4-Methoxy-phenyl)-2H-pyrazol-3-yl]-thieno[3,2-d]pyrimidin-4-yl-amine;
4-[5-(Thieno[3,2-d]pyrimidin-4-ylamino)-1H-pyrazol-3-yl]-benzoic acid methyl ester;
(5-Methyl-2H-pyrazol-3-yl)-thieno[3,2-d]pyrimidin-4-yl-amine;
5-(6-Phenyl-thieno[3,2-d]pyrimidin-4-ylamino)-1H-indole-2-carboxylic acid ethyl ester;
(6-Benzofuran-2-yl-thieno[3,2-d]pyrimidin-4-yl)-(1H-indol-5-yl)-amine;
Thieno[3,2-d]pyrimidin-4-yl-(5-m-tolyl-2H-pyrazol-3-yl)-amine;
[5-(3-Chloro-phenyl)-2H-pyrazol-3-yl]-thieno[3,2-d]pyrimidin-4-yl-amine;
[6-(4-Ethyl-phenyl)-thieno[3,2-d]pyrimidin-4-yl]-(1H-indol-5-yl)-amine;
4-[4-(1H-Indol-5-ylamino)-thieno[3,2-d]pyrimidin-6-yl]-benzoic acid methyl ester;
4-[5-(Thieno[3,2-d]pyrimidin-4-ylamino)-1H-pyrazol-3-yl]-benzoic acid;
(1H-Indol-5-yl)-(6-thiophen-2-yl-thieno[3,2-d]pyrimidin-4-yl)-amine;
[5-(2-Chloro-phenyl)-2H-pyrazol-3yl]thieno[3,2d]pyrimidin-4yl-amine:
(1H-Indol-5-yl)-(6-pyridin-3-yl-thieno[3,2-d]pyrimidin-4-yl)-amine;
(1H-Indol-5-yl)-[6-(3-methoxy-phenyl)-thieno[3,2-d]pyrimidin-4-yl]-amine;
{4-[4-(1H-Indol-5-ylamino)-thieno[3,2-d]pyrimidin-6-yl]-phenyl}-methanol;
[6-(3,4-Dimethoxy-phenyl)-thieno[3,2-d]pyrimidin-4-yl]-(1H-indol-5-yl)-amine;
[6-(4-Dimethylamino-phenyl)-thieno[3,2-d]pyrimidin-4-yl]-(1H-indol-5-yl)-amine;
[4-(1H-Indol-5-ylamino)-thieno[3,2-d]pyrimidin-6-yl]-phenyl-methanol;
4-(1H-Indol-5-ylamino)-thieno[3,2-d]pyrimidine-6-carboxylic acid (2-dimethylamino-ethyl)-amide;
(1H-Indol-5-yl)-[6-(4-trifluoromethoxy-phenyl)-thieno[3,2-d]pyrimidin-4-yl]-amine;
(1H-Indol-5-yl)-[6-(2-methoxy-phenyl)-thieno[3,2-d]pyrimidin-4-yl]-amine;
4-[4-(1H-Indol-5-ylamino)-thieno[3,2-d]pyrimidin-6-yl]-phenol;
[6-(5-Diethoxymethyl-thiophen-2-yl)-thieno[3,2-d]pyrimidin-4-yl]-(1H-indol-5-yl)-amine;
4-(1H-Indol-5-ylamino)-thieno[3,2-d]pyrimidine-6-carboxylic acid (2-methoxy-ethyl)-amide;
N-{4-[4-(1H-Indol-5-ylamino)-thieno[3,2-d]pyrimidin-6-yl]-benzyl}-N',N'-dimethyl-ethane-1,2-diamine;
(1H-Indol-5-yl)-(6-{4-[(2-methoxy-ethylamino)-methyl]-phenyl}-thieno[3,2-d]pyrimidin-4-yl)-amine;
(1H-Indol-5-yl)-{6-[2-(4-methyl-piperazin-1-yl)-phenyl]-thieno[3,2-d]pyrimidin-4-yl}-amine;
4-(1H-Indol-5-ylamino)-thieno[3,2-d]pyrimidine-6-carboxylic acid propylamide;
2-{4-[4-(1H-Indol-5-ylamino)-thieno[3,2-d]pyrimidin-6-yl]-benzylamino}-ethanol;
[6-(2,4-Dimethoxy-phenyl)-thieno[3,2-d]pyrimidin-4-yl]-(1H-indol-5-yl)-amine;
[6-(4-Diethylamino-phenyl)-thieno[3,2-d]pyrimidin-4-yl]-(1H-indol(-5-yl)-amine;
[6-(4-Ethoxy-phenyl)-thieno[3,2-d]pyrimidin-4-yl]-(1H-indol-5-yl)-amine;
3-{4-[4-(1H-Indol-5-ylamino)-thieno[3,2-d]pyrimidin-6-yl]-benzylamino}-propane-1,2-diol;
(1H-Indol-5-yl)-[6-(4-propylaminomethyl-phenyl)-thieno[3,2-d]pyrimidin-4-yl]-amine;
(1H-(Indol-5-yl)-(6-{4-[(3-methoxy-propylamino)-methyl]-phenyl}-thieno[3,2-d]pyrimidin-4-yl)-amine;
[6-(3-Fluoro-4-methoxy-phenyl)-thieno[3,2-d]pyrimidin-4-yl]-(1H-indol-5-yl)-amine;
(1H-Indol-5-yl)-[6-(3-methylsulfanyl-phenyl)-thieno[3,2-d]pyrimidin-4-yl]-amine;
(1H-Indol-5-yl)-[6-(5-methyl-thiophen-2-yl)-thieno[3,2-d]pyrimidin-4-yl]-amine;
(1H-Indol-5-yl)-(6-{4-[(2-piperazin-1-yl-ethyl amino)-methyl]-phenyl}-thieno[3,2-d]pyrimidin-4-yl)-amine;
(6-Benzo[1,3]dioxol-5-yl-thieno[3,2-d]pyrimidin-4-yl)-(1H-indol-5-yl)-amine;
{6-[4-(1-Ethoxy-ethoxy)-phenyl]-thieno[3,2-d]pyrimidin-4-yl}-(1H-indol-5-yl)-amine;
(1H-Indol-5-yl)-{6-[4-(2-pyrrolidin-1-yl-ethoxy)-phenyl]-thieno[3,2-d]pyrimidin-4-yl}-amine;
(1H-Indol-5-yl)-(6-{4-(2-methoxy-ethoxy)-phenyl]-thieno[3,2-d]pyrimidin-4-yl)-amine;

(1H-indol-5-yl)-(6-{4-[(2-morpholin-4-yl-ethylamino)-methyl]-phenyl}-thieno[3,2-d]pyrimidin-4-yl)-amine;
{6-[4-(2-Dimethylamino-ethoxy)-phenyl]-thieno[3,2-d]pyrimidin-4-yl}-(1H-indol-5-yl)-amine;
(1H-indol-5-yl)-[6-(4-methylaminomethyl-phenyl)-thieno[3,2-d]pyrimidin-4-yl]-amine;
5-(6-Phenyl-thieno[3,2-d]pyrimidin-4-ylamino)-1,3-dihydro-indol-2-one;
(1H-Benzotriazol-5-yl)-(6-phenyl-thieno[3,2-d]pyrimidin-4-yl)-amine;
(6-Phenyl-thieno[3,2-d]pyrimidin-4-yl)-[4-(2H-tetrazol-5-yl)-phenyl]-amine;
N-{4-[4-(1H-Indol-5-ylamino)-thieno[3,2-d]pyrimidin-6-yl]-benzyl}-N'-methyl-ethane-1,2-diamine;
(1-Benzenesulfonyl-1H-indol-5-yl)-(6-phenyl-thieno[3,2-d]pyrimidin-4-yl)-amine;
3-{4-[4-(1H-Indol-5-ylamino)-thieno[3,2-d]pyrimidin-6-yl]-benzylamino}-propan-1-ol;
(1H-indol-5-yl)-{6-[4-(4-methyl-piperazin-1-ylmethyl)-phenyl]-thieno[3,2-d]pyrimidin-4-yl}-amine;
2-{4-[4-(1H-Indol-5-ylamino)-thieno[3,2-d]pyrimidin-6-yl]-benzylamino}-propane-1,3-diol;
2-((2-Hydroxy-ethyl)-{4-(4-(1H-indol-5-ylamino)-thieno[3,2-d]pyrimidin-6-yl]-benzyl}-amino)-ethanol;
{5-[4-(1H-Indol-5-ylamino)-thieno[3,2-d]pyrimidin-6-yl]-thiophen-2-yl}-methanol;
2-(2-{4-[4-(1H-Indol-5-ylamino)-thieno[3,2-d]pyrimidin-6-yl]-benzylamino}-ethoxy)-ethanol;
2-(2-{4-[4-(1H-Indol-5-ylamino)-thieno[3,2-d]pyrimidin-6-yl]-benzylamino}-ethylamino)-ethanol;
[6-(4-{[2-(1H-Imidazol-4-yl)-ethylamino]-methyl}-phenyl)-thieno[3,2-d]pyrimidin-4-yl]-(1H-indol-5-yl)-amine;
(1H-Indol-5-yl)-{6-[4-(2-morpholin-4-yl-ethoxy)-phenyl]-thieno[3,2-d]pyrimidin-4-yl}-amine;
2-{4-[4-(1H-Indol-5-ylamino)-thieno[3,2-d]pyrimidin-6-yl]-phenoxy}-ethanol;
[4-(2-Ethyl-oxazol-5-yl)-phenyl]-(6-phenyl-thieno[3,2-d]pyrimidin-4-yl)-amine;
N-(2-Methoxy-phenyl)-N'-(6-phenyl-thieno[3,2-d]pyrimidin-4-yl)-benzene-1,4-diamine;
N-(4-Methoxy-phenyl)-N'-(6-phenyl-thieno[3,2-d]pyrimidin-4-yl)-benzene-1,4-diamine;
5-[4-(1H-Indol-5-ylamino)-thieno[3,2-d]pyrimidin-6-yl]-thiophene-2-carbaldehyde;
[5-(6-Phenyl-thieno[3,2-d]pyrimidin-4-ylamino)-1H-indol-2-yl]-methanol;
(2-Phenyl-1H-indol-3-yl)-(6-phenyl-thieno[3,2-d]pyrimidin-4-yl)-amine;
(9H-Carbazol-3-yl)-(6-phenyl-thieno[3,2-d]pyrimidin-4-yl)-amine;
(2-Methyl-1H-indol-5-yl)-(6-phenyl-thieno[3,2-d]pyrimidin-4-yl)-amine;
(1-Phenyl-ethyl)-(6-phenyl-thieno[3,2-d]pyrimidin-4-yl)-amine;
(1H-Indol-5-yl)-[6-(4-{[(thiophen-2-ylmethyl)-amino]-methyl}-phenyl)-thieno[3,2-d]pyrimidin-4-yl]-amine;
3-{4-[4-(1H-Indol-5-ylamino)-thieno[3,2-d]pyrimidin-6-yl]-benzylamino}-propionic acid methyl ester;
[6-(4-{[(Furan-2-ylmethyl)-amino]-methyl}-phenyl)-thieno[3,2-d]pyrimidin-4-yl]-(1H-indol-5-yl)-amine;
1-(3-{4-[4-(1H-Indol-5-ylamino)-thieno[3,2-d]pyrimidin-6-yl]-benzylamino}-propyl)-pyrrolidin-2-one;
N-{4-[4-(1H-Indol-5-ylamino)-thieno[3,2-d]pyrimidin-6-yl]-benzyl}-N',N'-dimethyl-propane-1,3-diamine;
(1H-Indol-5-yl)-[6-(4-morpholin-4-ylmethyl-phenyl)-thieno[3,2-d]pyrimidin-4-yl]-amine;
(2-{4-[4-(1H-Indol-5-ylamino)-thieno[3,2-d]pyrimidin-6-yl]-benzylamino}-acetylamino)-acetic acid ethyl ester;
1-(4-{4-[4-(1H-indol-5-ylamino)-thieno[3,2-d]pyrimidin-6-yl]-benzyl}-piperazin-1-yl)-ethanone;
(6-{4-[(2,2-Diphenyl-ethylamino)-methyl]-phenyl}-thieno[3,2-d]pyrimidin-4-yl)-(1H-indol-5-yl)-amine;
(1H-indol-5-yl)-{6-[4-(2-methoxymethyl-pyrrolidin-1-ylmethyl)-phenyl]-thieno[3,2-d]pyrimidin-4-yl}-amine;
N-(2-{4-[4-(1H-Indol-5-ylamino)-thieno[3,2-d]pyrimidin-6-yl]-benzylamino}-ethyl)-acetamide;
[6-(4-Cyclopropylaminomethyl-phenyl)-thieno[3,2-d]pyrimidin-4-yl]-(1H-indol-5-yl)-amine;
2-{4-[4-(1H-Indol-5-ylamino)-thieno[3,2-d]pyrimidin-6-yl]-benzylamino}-butan-1-ol;
2-({5-[4-(1H-Indol-5-ylamino)-thieno[3,2-d]pyrimidin-6-yl]-thiophen-2-ylmethyl}-amino)-ethanol;
(1H-Indol-5-yl)-(6-{4-[(2-pyrrolidin-1-yl-ethylamino)-methyl]-phenyl}-thieno[3,2-d]pyrimidin-4-yl)-amine;
(1H-Indol-5-yl)-(2-thiophen-2-yl-thieno[3,2-b]pyridin-7-yl)-amine;
{6-[4-(Benzylamino-methyl)-phenyl]-thieno[3,2-d]pyrimidin-4-yl}-(1H-indol-5-yl)-amine;
1-{4-[4-(1H-Indol-5-ylamino)-thieno[3,2-d]pyrimidin-6-yl]-benzyl}-piperidine-4-carboxylic acid amide;
(1H-Indol-5-yl)-{6-[4-(pyrrolidin-3-ylaminomethyl)-phenyl]-thieno[3,2-d]pyrimidin-4yl}-amine;
4-[7-(1H-Indol-5-ylamino)-thieno[3,2-b]pyridin-2-yl]-benzaldehyde;
(6-{4-[(3-Imidazol-1-yl-propylamino)-methyl]-phenyl}-thieno[3,2-d]pyrimidin-4-yl)-(1H-indol-5-yl)-amine;
N-{4-[4-(1H-Indol-5-ylamino)-thieno[3,2-d]pyrimidin-6-yl]-benzyl}-N',N'-dimethyl-hexane-1,6-diamine;
(1-Allyl-1H-indol-5-yl)-(6-phenyl-thieno[3,2-d]pyrimidin-4-yl)-amine;
(1-Methyl-1H-indol-5-yl)-(6-phenyl-thieno[3,2-d]pyrimidin-4-yl)-amine;
(1H-Indol-5-yl)-{6-[4-(4-phenyl-piperazin-1-ylmethyl)-phenyl]-thieno[3,2-d]pyrimidin-4-yl}-amine;
N-{5-[4-(1H-indol-5-ylamino)-thieno[3,2-d]pyrimidin-6-yl]-thiophen-2-ylmethyl}-N',N'-dimethyl-ethane-1,2-diamine;
N-{5-[4-(1H-indol-5-ylamino)-thieno[3,2-d]pyrimidin-6-yl]-thiophen-2-ylmethyl}-N'-methyl-ethane-1,2-diamine;
(1H-Indol-5-yl)-(6-{5-[(2-methoxy-ethylamino)-methyl]-thiophen-2-yl}-thieno[3,2-d]pyrimidin-4-yl)-amine;
2-Amino-3-(3-{4-[4-(1H-indol-5-ylamino)-thieno[3,2-d]pyrimidin-6-yl]-benzyl}-3H-imidazol-4-yl)-propionic acid methyl ester;
3-{4-[4-(1H-Indol-5-ylamino)-thieno[3,2-d]pyrimidin-6-yl]-benzylamino}-2,2-dimethyl-propan-1-ol;
4-[7-(1H-Indol-5-ylamino)-thieno[3,2-b]pyridin-2-yl]-phenol;
(9-Ethyl-9H-carbazol-3-yl)-(6-phenyl-thieno[3,2-d]pyrimidin-4-yl)-amine;
[1-(2-Diethylamino-ethyl)-1H-indol-5-yl]-(6-phenyl-thieno[3,2-d]pyrimidin-4-yl)-amine;
[1-(3-Diethylamino-propyl)-1H-indol-5-yl]-(6-phenyl-thieno[3,2-d]pyrimidin-4-yl)-amine;
(2-Bromo-thieno[3,2-b]pyridin-7-yl)-(1H-indol-5-yl)-amine;
[6-(4-Aminomethyl-phenyl)-thieno[3,2-d]pyrimidin-4-yl]-(1H-indol-5-yl)-amine;
3-Hydroxy-2-{4-[4-(1H-indol-5-ylamino)-thieno[3,2-d]pyrimidin-6-yl]-benzylamino}-propionic acid methyl ester;
Furan-2-yl-(4-{4-[4-(1H-indol-5-ylamino)-thieno[3,2-d]pyrimidin-6-yl]-benzyl}-piperazin-1-yl)-methanone;

(1H-indol-5-yl)-[2-(4-methylsulfanyl-phenyl)-thieno[3,2-b]pyridin-7-yl]-amine;
(6-(4-Dimethylaminomethyl-phenyl)-thieno[3,2-d]pyrimidin-4-yl]-(1H-indol-5-yl)-amine;
2-({4-[4-(1H-Indol-5-ylamino)-thieno[3,2-d]pyrimidin-6-yl]-benzyl}-methyl-amino)-ethanol;
(1-{4-[4-(1H-Indol-5-ylamino)-thieno[3,2-d]pyrimidin-6-yl]-benzyl}-pyrrolidin-2-yl)-methanol;
2-[2-(4-{4-[4-(1H-Indol-5-ylamino)-thieno[3,2-d]pyrimidin-6-yl]-benzyl}-piperazin-1-yl)-ethoxy]-ethanol;
[2-(4-Fluoro-phenyl)-thieno[3,2-b]pyridin-7-yl]-(1H-indol-5-yl)-amine;
4-[4-(1H-Indol-5-ylamino)-thieno[3,2-d]pyrimidin-6-yl]-benzoic acid;
(1H-Indol-5-yl)-thieno[3,2-b]pyridin-7-yl-amine;
2-{4-[7-(1H-Indol-5-ylamino)-thieno[3,2-b]pyridin-2-yl]-phenoxy}-ethanol;
(1H-Indol-5-yl)-(2-methyl-6-phenyl-thieno[3,2-d]pyrimidin-4-yl)-amine;
N-(4-Methoxy-phenyl)-N'-(2-methyl-6-phenyl-thieno[3,2-d]pyrimidin-4-yl)-benzene-1,4-diamine;
N-(2-Benzyloxy-ethyl)-N'-(6-phenyl-thieno[3,2-d]pyrimidin-4-yl)-benzene-1,4-diamine;
5-(6-Phenyl-thieno[3,2-d]pyrimidin-4-ylamino)-1H-indole-3-carbaldehyde;
[2-(4-Dimethylamino-phenyl)-thieno[3,2-b]pyridin-7-yl]-(1H-indol-5-yl)-amine;
4-[7-(1H-Indol-5-ylamino)-thieno[3,2-b]pyridin-2-yl]-benzoic acid methyl ester;
(1H-Indol-5-yl)-(2-thiophen-3-yl-thieno[3,2-b]pyridin-7-yl)-amine;
(1H-Indol-5-yl)-(2-{4-[(2-methoxy-ethylamino)-methyl]-phenyl}-thieno[3,2-b]pyridin-7-yl)-amine;
Furan-2-yl-(4-{4-[7-(1H-indol-5-ylamino)-thieno[3,2-b]pyridin-2-yl]-benzyl}-piperazin-1-yl)-methanone;
(3-Bromo-1H-indol-5-yl)-(6-phenyl-thieno[3,2-d]pyrimidin-4-yl)-amine;
N-(1H-Indol-3-ylmethyl)-N'-(6-phenyl-thieno[3,2-d]pyrimidin-4-yl)-benzene-1,4-diamine;
N-(6-Bromo-thieno[3,2-d]pyrimidin-4-yl)-N'-(4-methoxy-phenyl)-benzene-1,4-diamine;
N-(4-Methoxy-phenyl)-N'-[6-(2-nitro-phenyl)-thieno[3,2-d]pyrimidin-4-yl]-benzene-1,4-diamine;
N-(4-Methoxy-phenyl)-N'-[6-(4-methoxy-phenyl)-thieno[3,2-d]pyrimidin-4-yl]-benzene-1,4-diamine;
N-(4-Methoxy-phenyl)-N'-[6-(6-methoxy-pyridin-3-yl 3-thieno[3,2-d]pyrimidin-4-yl]-benzene-1,4-diamine;
N-(4-Methoxy-phenyl)-N'-(6-thiophen-2-yl-thieno[3,2-d]pyrimidin-4-yl)-benzene-1,4-diamine;
(1H-Indol-5-yl)-[6-(4-thiomorpholin-4-ylmethyl-phenyl)-thieno[3,2-d]pyrimidin-4-yl]-amine;
2-(2-{4-[7-(1H-Indol-5-ylamino)-thieno[3,2-b]pyridin-2-yl]-benzylamino}-ethoxy)-ethanol;
2-{4-[7-(1H-Indol-5-ylamino)-thieno[3,2-b]pyridin-2-yl]-benzylamino}-ethanol;
N-{4-[7-(1H-indol-5-ylamino)-thieno[3,2-b]pyridin-2-yl]-benzyl}-N',N'-dimethyl-hexane-1,6-diamine;
2-({4-[7-(1H-indol-5-ylamino)-thieno[3,2-b]pyridin-2-yl]-benzyl}-methyl-amino)-ethanol
(1H-Indol-5-yl)-(2-{4-[(2-piperazin-1-yl-ethylamino)-methyl]-phenyl}-thieno[3,2-b]pyridin-7-yl)-amine;
(2-{4-[(3-Imidazol-1-yl-propylamino)-methyl]-phenyl}-thieno[3,2-b]pyridin-7-yl)-(1H-indol-5-yl)-amine;
2-((2-Hydroxy-ethyl)-{4-[7-(1H-indol-5-ylamino)-thieno[3,2-b]pyridin-2-yl]-benzyl}-amino)-ethanol;
[2-(4-Dimethylaminomethyl-phenyl)-thieno[3,2-b]pyridin-7-yl]-(1H-indol-5-yl)-amine;
N-{4-[7-(1H-Indol-5-ylamino)-thieno[3,2-b]pyridin-2-yl]-benzyl}-N',N'-dimethyl-ethane-1,2-diamine;
(1-{4-[7-(1H-Indol-5-ylamino)-thieno[3,2-b]pyridin-2-yl]-benzyl}-pyrrolidin-2-yl)-methanol;
2-(4-{4-[7-(1H-Indol-5-ylamino)-thieno[3,2-b]pyridin-2-yl]-benzyl}-piperazin-1-yl)-ethanol;
(1H-Indol-5-yl)-{2-[4-(2-morpholin-4-yl-ethoxy)-phenyl]-thieno[3,2-b]pyridin-7-yl}-amine;
1-{4-[7-(1H-indol-5-ylamino)-thieno[3,2-b]pyridin-2-yl]-benzyl}-piperidine-4-carboxylic acid amide;
{4-[7-(1H-Indol-5-ylamino)-thieno[3,2-b]pyridin-2-yl]-phenyl}-methanol;
6-(6-Phenyl-thieno[3,2-d]pyrimidin-4-ylamino)-benzothiazole-2-thiol;
2-{4-[7-(1H-Indol-5-ylamino)-thieno[3,2-b]pyridin-2-yl]-benzylamino}-butan-1-ol;
N-{4-[7-(1H-Indol-5-ylamino)-thieno[3,2-b]pyridin-2-yl]-benzyl}-N'-methyl-ethane-1,2-diamine;
(1H-Indol-5-yl)-[2-(4-morpholin-4-ylmethyl-phenyl)-thieno[3,2-b]pyridin-7-yl]-amine;
3-{4-[7-(1H-Indol-5-ylamino)-thieno[3,2-b]pyridin-2-yl]-benzylamino}-propan-1-ol;
1-(3-{4-[7-(1H-Indol-5-ylamino)-thieno[3,2-b]pyridin-2-yl]-benzylamino}-propyl)-pyrrolidin-2-one;
(3-Methyl-1H-indol-5-yl)-(6-phenyl-thieno[3,2-d]pyrimidin-4-yl)-amine;
(1H-indol-5-yl)-{2-[4-(2-methoxy-ethoxy)-phenyl]-thieno[3,2-b]pyridin-7-yl}-amine;
2-(2-{4-[7-(1H-Indol-5-ylamino)-thieno[3,2-b]pyridin-2-yl]-benzylamino}-ethylamino)-ethanol;
3-{4-[7-(1H-indol-5-ylamino)-thieno[3,2-b]pyridin-2-yl]-benzylamino}-2,2-dimethyl-propan-1-ol;
3-{4-[7-(1H-Indol-5-ylamino)-thieno[3,2-b]pyridin-2-yl]-benzylamino}-propane-1,2-diol;
[2-(4-{[2-(1H-Imidazol-4-yl)-ethylamino]-methyl}-phenyl)-thieno[3,2-b]pyridin-7-yl]-(1H-indol-5-yl)-amine;
N-(2-{4-[7-(1H-indol-5-ylamino)-thieno[3,2-b]pyridin-2-yl]-benzylamino}-ethyl)-acetamide;
2-{4-[7-(1H-indol-5-ylamino)-thieno[3,2-b]pyridin-2-yl]-benzylamino}-acetamide;
2-{4-[7-(1H-Indol-5-ylamino)-thieno[3,2-b]pyridin-2-yl]-benzylamino}-propane-1,3-diol;
N-(4-Methoxy-phenyl)-N'-[2-(3-nitro-phenyl)-thieno[3,2-b]pyridin-7-yl]-benzene-1,4-diamine;
(7-Methoxy-1H-indol-5-yl)-(2-phenyl-thieno[3,2-b]pyridin-7-yl)-amine;
(1H-indol-5-yl)-[2-(4-methylaminomethyl-phenyl)-thieno[3,2-b]pyridin-7-yl]-amine;
N-{4-[7-(1H-Indol-5-ylamino)-thieno[3,2-b]pyridin-2-yl]-benzyl}-ethane-1,2-diamine;
{4-[7-(1H-Indol-5-ylamino)-thieno[3,2-b]pyridin-2-yl]-benzylamino}-acetic acid methyl ester;
N-{4-[7-(1H-Indol-5-ylamino)-thieno[3,2-b]pyridin-2-yl]-benzyl}-N',N'-dimethyl-propane-1,3-diamine;
N-(4-Methoxy-phenyl)-N'-thieno[3,2-d]pyrimidin-4-yl-benzene-1,4-diamine;
(1H-Indol-5-yl)-(2-pyridin-2-yl-thieno[3,2-b]pyridin-7-yl)-amine;
(1H-Indol-5-yl)-(2-{4-[(2-morpholin-4-yl-ethylamino)-methyl]-phenyl}-thieno[3,2-b]pyridin-7-yl)-amine;
(1H-Indol-5-yl)-{2-[4-(pyrrolidin-3-ylaminomethyl)-phenyl]-thieno[3,2-b]pyridin-7-yl}-amine;
1-(4-{4-[7-(1H-Indol-5-ylamino)-thieno[3,2-b]pyridin-2-yl]-benzyl}-piperazin-1-yl)-ethanone;
1-{4-[7-(1H-Indol-5-ylamino)-thieno[3,2-b]pyridin-2-yl]-benzyl}-pyrrolidine-2-carboxylic acid amide;

N-(4-Methoxy-phenyl)-N'-[2-(6-methoxy-pyridin-3-yl)-thieno[3,2-b]pyridin-7-yl]-benzene-1,4-diamine;
(1H-indol-5-yl)-(2-pyridin-3-yl-thieno[3,2-b]pyridin-7-yl)-amine;
N-(2-Methoxy-phenyl)-N'-(6-phenyl-thieno[3,2-d]pyrimidin-4-yl)-benzene-1,4-diamine;
N-(6-Phenyl-thieno[3,2-d]pyrimidin-4-yl)-N'-o-tolyl-benzene-1,4-diamine;
N-(6-Phenyl-thieno[3,2-d]pyrimidin-4-yl)-N'-p-tolyl-benzene-1,4-diamine;
N-(3,4-Dimethoxy-phenyl)-N'-(6-phenyl-thieno[3,2-d]pyrimidin-4-yl)-benzene-1,4-diamine;
N-(6-Phenyl-thieno[3,2-d]pyrimidin-4-yl)-N'-(3,4,5-trimethoxy-phenyl)-benzene-1,4-diamine;
N-(6-Phenyl-thieno[3,2-d]pyrimidin-4-yl)-N'-m-tolyl-benzene-1,4-diamine;
N-(4-Chloro-phenyl)-N'-(6-phenyl-thieno[3,2-d)benzene-1,4diamine;
4-[7-(1H-indol-5-ylamino)-thieno[3,2-b]pyridin-2-yl]-but-3-yn-1-ol;
(1H-indol-5-yl)-[6-(6-methoxy-pyridin-3-yl)-thieno[3,2d]pyrimidin-4-yl]-amine;
N-(4dimethylamino-phenyl)-N'-(6-phenyl-thieno[3,2-d]pyrimidin-4-yl)benzene-1,4-diamine;
N-(3-Methoxy-phenyl)-N'-(6-phenyl-thieno[3,2-d]pyrimidin-4-yl)-benzene-1,4-diamine;
(1,3-Dibromo-1H-indol-5-yl)-(6-phenyl-thieno[3,2-d]pyrimidin-4-yl)-amine;
N-(4-Methoxy-phenyl)-N'-(2-thiophen-2-yl-thieno[3,2-b]pyridin-7-yl)-benzene-1,4-diamine;
(6-Chloro-1H-indol-5-yl)-(6-phenyl-thieno[3,2-d]pyrimidin-4-yl)-amine;
[5-(6-Phenyl-thieno[3,2-d]pyrimidin-4-ylamino)-1H-indol-3-yl]-methanol;
N-(2-Hydroxy-ethyl)-4-[7-(1H-indol-5-ylamino)-thieno[3,2-b]pyridin-2-yl]-benzamide;
N-(3-Imidazol-1-yl-propyl)-4-[7-(1H-indol-5-ylamino)-thieno[3,2-b]pyridin-2-yl]-benzamide;
3-[4-(4-{4-[7-(1H-Indol-5-ylamino)-thieno[3,2-b]pyridin-2-yl]-benzylamino}-butyl)-piperazin-1-yl]-propan-1-ol;
(1H-Indol-5-yl)-[2-(4-{[4-(4-methyl-piperazin-1-yl)-butylamino]-methyl}-phenyl)-thieno[3,2-b]pyridin-7-yl]-amine;
2-[4-(4-{4-[7-(1H-Indol-5-ylamino)-thieno[3,2-b]pyridin-2-yl]-benzylamino}-butyl)-piperazin-1-yl]-ethanol;
1-Imidazol-1-yl-3-{4-[7-(1H-indol-5-ylamino)-thieno[3,2-b]pyridin-2-yl]-benzylamino}-propan-2-ol;
5-{4-[7-(1H-Indol-5-ylamino)-thieno[3,2-b]pyridin-2-yl]-benzylamino}-pentan-1ol;
2-[2-(4-{4-[7-(1H-Indol-5-ylamino)-thieno[3,2-b]pyridin-2-yl]-benzyl}-piperazin-1yl)-ethoxy]-ethanol;
(1H-indol-5-yl)-(2-{4-[(2-methylsulfanyl-ethylamino)-methyl]-phenyl}-thieno[3,2-b]pyridin-7-yl)-amine;
2-[(2-Hydroxy-ethyl)-(3-{4-[7-(1H-indol-5-ylamino)-thieno[3,2-b]pyridin-2yl]-benzylamino}-propyl)-amino]-ethanol;
N-(2-Amino-ethyl)-N'-{4-[7-(1H-indol-5-ylamino)-thieno[3,2-b]pyridin-2-yl]-benzyl}-ethane-1,2-diamine;
2-(3-{4-[7-(1H-Indol-5-ylamino)-thieno[3,2-b]pyridin-2-yl]-benzylamino}-propylamino)-ethanol;
N-{4-[7-(1H-Indol-5-ylamino)-thieno[3,2-b]pyridin-2-yl]-benzyl}-hexane-1,6-diamine
(2-Methyl-1H-indol-5-yl)-[2-(4-morpholin-4-ylmethyl-phenyl)-thieno[3,2-b]pyridin-7-yl]amine;
(6-Phenyl-thieno[3,2-d]pyrimidin-4-yl)-{3-[(3-pyrazol-1-yl-propylamino)-methyl]-1H-indol-5-yl}-amine;
{[5-(6-Phenyl-thieno[3,2-d]pyrimidin-4-ylamino)-1H-indol-3-ylmethyl]-amino}-acetic acid methyl ester;
2-{[5-(6-Phenyl-thieno[3,2-d]pyrimidin-4-ylamino)-1H-indol-3-ylmethyl]-amino}-ethanol;
2-{4-[7-(2-Methyl-1H-indol-5-ylamino)-thieno[3,2-b]pyridin-2-yl]-benzylamino}-ethanol;
(1H-Indol-5-yl)-[2-(6-methoxy-pyridin-3-yl)-thieno[3,2-b]pyridin-7-yl]-amine;
{5-[7-(1H-Indol-5-ylamino)-thieno[3,2-b]pyridin-2-yl]-pyridin-2-yl}-methanol;
N,N-Dimethyl-N'-{4-[7-(2-methyl-1H-indol-5-ylamino)-thieno[3,2-b]pyridin-2-yl]-benzyl}-propane-1,3-diamine;
5-(6-Phenyl-thieno[3,2-d]pyrimidin-4-ylamino)-1H-indole-3-carbaldehyde oxime;
(3-Methyliminomethyl-1H-indol-5-yl)-(6-phenyl-thieno[3,2-d]pyrimidin-4-yl)-amine;
[3-(2-Nitro-vinyl)-1H-indol-5-yl]-(6-phenyl-thieno[3,2-d]pyrimidin-4-yl)-amine;
4-[4-(6-Phenyl-thieno[3,2-d]pyrimidin-4-ylamino)-phenylamino]-phenol;
5-Methyl-1-[4-(6-phenyl-thieno[3,2-d]pyrimidin-4-ylamino)-phenyl]-1,2-dihydro-pyrazol-3-one;
(2-Methyl-benzothiazol-6-yl)-(6-phenyl-thieno[3,2-d]pyrimidin-4-yl)-amine;
2-[(2-Hydroxy-ethyl)-(3-{4-[7-(2-methyl-1H-indol-5-ylamino)-thieno[3,2-b]pyridin-2-yl]-benzylamino}-propyl)-amino]-ethanol;
2-{4-[7-(2-Methyl-1H-indol-5-ylamino)-thieno[3,2-b]pyridin-2-yl]-benzylamino}-propane-1,3-diol;
3-{4-[7-(2-Methyl-1H-indol-5-ylamino)-thieno[3,2-b]pyridin-2-yl]-benzylamino}-propane-1,2-diol;
1-(3-{4-[7-(2-Methyl-1H-indol-5-ylamino)-thieno[3,2-b]pyridin-2-yl]-benzylamino}-propyl)-pyrrolidin-2-one;
N-(2-Amino-ethyl)-N'-{4-[7-(2-methyl-1H-indol-5-ylamino)-thieno[3,2-b]pyridin-2-yl]-benzyl}-ethane-1,2-diamine;
2-(2-{4-[7-(2-Methyl-1H-indol-5-ylamino)-thieno[3,2-b]pyridin-2-yl]-benzylamino}-ethylamino)-ethanol;
3-{4-[7-(2-Methyl-1H-indol-5-ylamino)-thieno[3,2-b]pyridin-2-yl]-benzylamino}-propan-1-ol;
1-{4-[7-(2-Methyl-1H-indol-5-ylamino)-thieno[3,2-b]pyridin-2-yl]-benzyl}-piperidine-4-carboxylic acid amide;
2-(2-{4-[7-(2-Methyl-1H-indol-5-ylamino)-thieno[3,2-b]pyridin-2-yl]-benzylamino}-ethoxy)-ethanol;
2-(Methyl-{4-[7-(2-methyl-1H-indol-5-ylamino)-thieno[3,2-b]pyridin-2-yl]-benzyl}-amino)-ethanol;
N-Methyl-N'-{4-[7-(2-methyl-1H-indol-5-ylamino)-thieno[3,2-b]pyridin-2-yl]-benzyl}-ethane-1,2-diamine;
(1H-Indol-5-yl)-[2-(3-nitro-phenyl)-thieno[3,2-b]pyridin-7-yl]-amine;
N-{4-[7-(2-Methyl-1H-indol-5-ylamino)-thieno[3,2-b]pyridin-2-yl]-benzyl}-ethane-1,2-diamine;
(2-Methyl-1H-indol-5-yl)-(2-{4-[(2-piperazin-1-yl-ethylamino)-methyl]-phenyl}-thieno[3,2-b]pyridin-7-yl)-amine;
N,N-Dimethyl-N'-{4-[7-(2-methyl-1H-indol-5-ylamino)-thieno[3,2-b]pyridin-2-yl]-benzyl}-ethane-1,2-diamine;
2-{4-[7-(2-Methyl-1H-indol-5-ylamino)-thieno[3,2-b]pyridin-2-yl]-benzylamino}-butan-1-ol;
(2-Methyl-1H-indol-5-yl)-(2-{4-[(2-morpholin-4-yl-ethylamino)-methyl]-phenyl}-thieno[3,2-b]pyridin-7-yl)-amine;
(2-Methyl-1H-indol-5-yl)-{2-[4-(pyrrolidin-3-ylaminomethyl)-phenyl]-thieno[3,2-b]pyridin-7-yl}-amine;
{6-[7-(1H-Indol-5-ylamino)-thieno[3,2-b]pyridin-2-yl]-pyridin-3-yl}-methanol;
{6-[7-(2-Methyl-1H-indol-5-ylamino)-thieno[3,2-b]pyridin-2-yl]-pyridin-3-yl}-methanol (3-Methylaminomethyl-1H-indol-5-yl)-(6-phenyl-thieno[3,2-d]pyrimidin-4-yl)-amine;
3-[4-(4-{4-[7-(2-Methyl-1H-indol-5-ylamino)-thieno[3,2-b]pyridin-2-yl]-benzylamino}-butyl)-piperazin-1-yl]-propan-1-ol;
2-[4-(4-{4-[7-(2-Methyl-1H-indol-5-ylamino)-thieno[3,2-b]pyridin-2-yl]-benzylamino}-butyl)-piperazin-1-yl]-ethanol;
(2-{4-[(3-Imidazol-1-yl-propylamino)-methyl]-phenyl}-thieno[3,2-b]pyridin-7-yl)-(2-methyl-1H-indol-5-yl)-amine;
1-Imidazol-1-yl-3-{4-[7-(2-methyl-1H-indol-5-ylamino)-thieno[3,2-b]pyridin-2-yl]-benzylamino}-propan-2-ol;
2-[(2-Hydroxy-ethyl)-(4-{4-[7-(2-methyl-1H-indol-5-ylamino)-thieno[3,2-b]pyridin-2-yl]-benzylamino}-butyl)-amino]-ethanol;
N,N-Diethyl-N'-{4-[7-(2-methyl-1H-indol-5-ylamino)-thieno[3,2-b]pyridin-2-yl]-benzyl}-propane-1,3-diamine;
[2-(3-Amino-phenyl)-thieno[3,2-b]pyridin-7-yl]-(1H-indol-5-yl)-amine;
(2-Methyl-1H-indol-5-yl)-(2-{4-[(3-morpholin-4-yl-propylamino)-methyl]-phenyl}-thieno[3,2-b]pyridin-7-yl)-amine;
[2-(4-Dimethylaminomethyl-phenyl)-thieno[3,2-b]pyridin-7-yl]-(2-methyl-1H-indol-5-yl)-amine;
1-[5-(2-Pyridin-2-yl-thieno[3,2-b]pyridin-7-ylamino)-2,3-dihydro-indol-1-yl]-ethanone;
(2,3-Dihydro-1H-indol-5-yl)-(2-pyridin-2-yl-thieno[3,2-b]pyridin-7-yl)-amine;
(1H-Benzotriazol-5-yl)-(2-pyridin-2-yl-thieno[3,2-b]pyridin-7-yl)-amine;
5-(2-Phenyl-thieno[3,2-b]pyridin-7-ylamino)-1H-indole-3-carbaldehyde;
(1H-Indazol-5-yl)-(2-pyridin-2-yl-thieno[3,2-b]pyridin-7-yl)-amine;
(2-Methyl-1H-indol-5-yl)-(2-pyridin-2-yl-thieno[3,2-b]pyridin-7-yl)-amine;
(1H-Benzoimidazol-5-yl)-(2-phenyl-thieno[3,2-b]pyridin-7-yl)-amine;
5-(2-Pyridin-2-yl-thieno[3,2-b]pyridin-7-ylamino)-1H-indole-2-carboxylic acid dimethylamide;
{5-[7-(2-Methyl-1H-indol-5-ylamino)-thieno[3,2-b]pyridin-2-yl]-pyridin-2-yl}-methanol;
N-(3-Imidazol-1-yl-propyl)-6-[7-(1H-indol-5-ylamino)-thieno[3,2-b]pyridin-2-yl]-nicotinamide;
N-(3-Hydroxy-propyl)-6-[7-(2-methyl-1H-indol-5-ylamino)-thieno[3,2-b]pyridin-2-yl]-nicotinamide;
[2-(5-Amino-pyridin-2-yl)-thieno[3,2-b]pyridin-7-yl]-(2-methyl-1H-indol-5-yl)-amine;
N-[2-(2-Hydroxy-ethoxy)-ethyl]-6-[7-(2-methyl-1H-indol-5-ylamino)-thieno[3,2-b]pyridin-2-yl]-nicotinamide;
(4-Methoxy-2-methyl-phenyl)-(6-phenyl-thieno[3,2-d]pyrimidin-4-yl)-amine;
[4-(4-Chloro-phenoxy)-phenyl]-(6-phenyl-thieno[3,2-d]pyrimidin-4-yl)-amine;
6-(6-Phenyl-thieno[3,2-d]pyrimidin-4-ylamino)-1H-benzo[d][1,3]oxazine-2,4-dione;
2-Diethylaminomethyl-4-(6-phenyl-thieno[3,2-d]pyrimidin-4-ylamino)-phenol;
5-Methyl-1-[4-(6-phenyl-thieno[3,2-d]pyrimidin-4-ylamino)-phenyl]-1,2-dihydro-pyrazol-3-one;
[4-(4,5-Dichloro-imidazol-1-yl)-phenyl]-(6-phenyl-thieno[3,2-d]pyrimidin-4-yl)-amine;
(6-Phenyl-thieno[3,2-d]pyrimidin-4-yl)-[4-(3-trifluoromethyl-pyrazol-1-yl)-phenyl]-amine;
[4-(4-Methyl-piperazin-1-yl)-phenyl]-(6-phenyl-thieno[3,2-d]pyrimidin-4-yl)-amine;
[4-(4-Methyl-piperidin-1-yl)-phenyl]-(6-phenyl-thieno[3,2-d]pyrimidin-4-yl)-amine;
1-[4-(6-Phenyl-thieno[3,2-d]pyrimidin-4-ylamino)-phenyl]-1H-tetrazole-5-thiol;
3-(6-Phenyl-thieno[3,2-d]pyrimidin-4-ylamino)-benzenesulfonamide;
(2-Methyl-benzothiazol-6-yl)-(6-phenyl-thieno[3,2-d]pyrimidin-4-yl)-amine;
[4-(Morpholine-4-sulfonyl)-phenyl]-(6-phenyl-thieno[3,2-d]pyrimidin-4-yl)-amine;
[3,5-Dimethyl-4-(thiophen-3-yl methoxy)-phenyl]-(6-phenyl-thieno[3,2-d]pyrimidin-4-yl)-amine;
[4,5-Dimethoxy-2-(1H-tetrazol-5-yl)-phenyl]-(6-phenyl-thieno[3,2-d]pyrimidin-4-yl)-amine;
5-[4-(6-Phenyl-thieno[3,2-d]pyrimidin-4-ylamino)-phenyl]-oxazolidine-2,4-dione;
1-Ethyl-5-(6-phenyl-thieno[3,2-d]pyrimidin-4-ylamino)-1,3-dihydro-indol-2-one;
6-(6-Phenyl-thieno[3,2-d]pyrimidin-4-ylamino)-3H-benzooxazol-2-one;
Dibenzothiophen-4-yl-(6-phenyl-thieno[3,2-d]pyrimidin-4-yl)-amine;
N-(6-Phenyl-thieno[3,2-d]pyrimidin-4-yl)-N'-p-tolyl-benzene-1,2-diamine;
(2-Furan-2-yl-1-methyl-1H-benzoimidazol-5-yl)-(6-phenyl-thieno[3,2-d]pyrimidin-4-yl)-amine;
5-(6-Phenyl-thieno[3,2-d]pyrimidin-4-ylamino)-benzo[b]thiophene-2-carbonitrile;
(6-Phenyl-thieno[3,2-d]pyrimidin-4-yl)-(2-pyridin-4-yl-1H-benzoimidazol-5-yl)-amine;
[4-(1-Methyl-1H-imidazol-2-ylsulfanyl)-phenyl]-(6-phenyl-thieno[3,2-d]pyrimidin-4-yl)-amine;
(6-Phenyl-thieno[3,2-d]pyrimidin-4-yl)-[4-(pyridin-2-yloxy)-phenyl]-amine;
[4-(5-Methyl-tetrazol-1-yl)-phenyl]-(6-phenyl-thieno[3,2-d]pyrimidin-4-yl)-amine;
1-[3-(6-Phenyl-thieno[3,2-d]pyrimidin-4-ylamino)-phenyl]-1H-tetrazole-5-thiol;
4-[4-(6-Phenyl-thieno[3,2-d]pyrimidin-4-ylamino)-phenylamino]-phenol;
[3-(3-Methyl4,5-dihydro-pyrazol-1-yl)-phenyl]-(6-phenyl-thieno[3,2-d]pyrimidin-4-yl)-amine;
Benzo[1,2,3]thiadiazol-6-yl-(6-phenyl-thieno[3,2-d]pyrimidin-4-yl)-amine;
4-[7-(2-Methyl-1H-indol-5-ylamino)-thieno[3,2-b]pyridin-2-yl]-benzaldehyde
[6-(4-Fluoro-phenyl)-thieno[3,2-d]pyrimidin-4-yl]-(1H-indol-5-yl)-amine;
and the pharmaceutically acceptable salts and hydrates of the foregoing compounds. The present invention also relates to intermediate compounds of the formulas 25 and 26

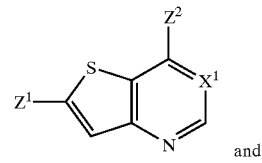
and

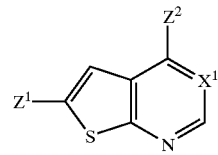

and to pharmaceutically acceptable salts thereof, wherein:

wherein $X^1$ is N or CH;

$Z^1$ is halo and $Z^2$ is —$NR^1R^2$; or $Z^1$ is $R^{11}$ and $Z^2$ is halo; or $Z^1$ and $Z^2$ are each independently halo;

$R^1$ is H, $C_1$–$C_6$ alkyl or —$C(O)(C_1$–$C_6$ alkyl);

$R^2$ is $C_6$–$C_{10}$ aryl or 5–13 membered heterocyclic, wherein said $R^2$ groups are optionally substituted by 1 to 5 $R^5$ substituents, each $R^5$ is independently selected from halo, cyano, nitro, trifluoromethoxy, trifluoromethyl, azido, —$C(O)R^8$, —$C(O)OR^8$, —$OC(O)R^8$, —$OC(O)OR^8$, —$NR^6C(O)R^7$, —$C(O)NR^6R^7$, —$NR^6R^7$, —$OR^9$, —$SO_2NR^6R^7$, $C_1$–$C_6$ alkyl, —$(CH_2)_jO(CH_2)_qNR^6R^7$, —$(CH_2)_tO(CH_2)_qOR^9$, —$(CH_2)_tOR^9$, —$S(O)_j(C_1$–$C_6$ alkyl), —$(CH_2)_t(C_6$–$C_{10}$ aryl), —$(CH_2)_t(5$–$10$ membered heterocyclic), —$C(O)(CH_2)_t(C_6$–$C_{10}$ aryl), —$(CH_2)_tO(CH_2)_j(C_6$–$C_{10}$ aryl), —$(CH_2)_tO(CH_2)_q(5$–$10$ membered heterocyclic —$C(O)(CH_2)_t(5$–$10$ membered heterocyclic), —$(CH_2)_jNR^7(CH_2)_qNR^6R^7$, —$(CH_2)_jNR^7CH_2C(O)NR^6R^7$, —$(CH_2)_jNR^7(CH_2)_qNR^9C(O)R^8$, —$(CH_2)_jNR^7(CH_2)_tO(CH_2)_qOR^9$, —$(CH_2)_jNR^7(CH_2)_qS(O)_j(C_1$–$C_6$ alkyl), —$(CH_2)_jNR^7(CH_2)_tR^6$, —$SO_2(CH_2)_t(C_6$–$C_{10}$ aryl), and —$SO_2(CH_2)_t(5$–$10$ membered heterocyclic), wherein j is an integer ranging from 0 to 2, t is an integer ranging from 0 to 6, q is an integer ranging from 2 to 6, the —$(CH_2)_q$—, and —$(CH_2)_t$— moieties of the foregoing $R^5$ groups optionally include a carbon-carbon double or triple bond where t is an integer between 2 and 6, and the alkyl, aryl and heterocyclic moieties of the foregoing $R^5$ groups are optionally substituted by 1 to 3 substituents independently selected from halo, cyano, nitro, trifluoromethyl, azido, —$C(O)R^8$, —$C(O)OR^8$, —$OC(O)R^8$, —$OC(O)OR^8$, —$NR^6C(O)R^7$, —$C(O)NR^6R^7$, —$(CH_2)_tNR^6R^7$, $C_1$–$C_6$ alkyl, —$(CH_2)_t(C_6$–$C_{10}$ aryl), —$(CH_2)_t(5$–$10$ membered heterocyclic), —$(CH_2)_tO(CH_2)_qOR^9$, and —$(CH_2)_tOR^9$, wherein t is an integer ranging from 0 to 6 and q is an integer ranging from 2 to 6;

each $R^6$ and $R^7$ is independently selected from H, $C_1$–$C_6$ alkyl, —$(CH_2)_t(C_6$–$C_{10}$ aryl), —$(CH_2)_t(5$–$10$ membered heterocyclic), —$(CH_2)_tO(CH_2)_qOR^9$, and —$(CH_2)_tOR^9$, wherein t is an integer ranging from 0 to 6 and q is an integer ranging from 2 to 6, and the alkyl, aryl and heterocyclic moieties of the foregoing $R^6$ and $R^7$ groups are optionally substituted by 1 to 3 substituents independently selected from halo, cyano, nitro, trifluoromethyl, azido, —$C(O)R^8$, —$C(O)OR^8$, —$CO(O)R^8$, —$OC(O)OR^{8,}$ —$NR^9C(O)R^{10}$, —$C(O)NR^9R^{10}$, —$NR^9R^{10}$, $C_1$–$C_6$ alkyl, —$(CH_2)_t(C_6$–$C_{10}$ aryl), —$(CH_2)_t(5$–$10$ membered heterocyclic), —$(CH_2)_tO(CH_2)_qOR^9$, and —$(CH_2)_tOR^9$, wherein t is an integer ranging from 0 to 6 and q is an integer ranging from 2 to 6, with the proviso that where $R^6$ and $R^7$ are both attached to the same nitrogen, then $R^6$ and $R^7$ are not both bonded to the nitrogen directly through an oxygen;

each $R^8$ is independently selected from H, $C_1$–$C_{10}$ alkyl, —$(CH_2)_t(C_6$–$C_{10}$ aryl), and —$(CH_2)_t(5$–$10$ membered heterocyclic), wherein t is an integer ranging from 0 to 6;

each $R^9$ and $R^{10}$ is independently selected from H and $C_1$–$C_6$ alkyl; and, $R^{11}$ is H, $C_1$–$C_6$ alkyl, —$C(O)NR^6R^9$, —$C(O)(C_6$–$C_{10}$ aryl), —$(CH_2)_t(C_6$–$C_{10}$ aryl), or —$(CH_2)_t(5$–$10$ membered heterocyclic), wherein t is an integer ranging from 0 to 6, wherein said $R^{11}$ groups, other than H, are optionally substituted by tert-butyl-dimethyl-silanyl and 1 to 3 $R^5$ groups.

The above intermediates of formulas 25 and 26 may be used to prepare the above compounds of formulas 1 and 2.

The invention also relates to a pharmaceutical composition for the treatment of a hyperproliferative disorder in a mammal which comprises a therapeutically effective amount of a compound of formula 1 or 2, or a pharmaceutically acceptable salt or hydrate thereof, and a pharmaceutically acceptable carrier. In one embodiment, said pharmaceutical composition is for the treatment of cancer such as brain, lung, squamous cell, bladder, gastric, pancreatic, breast, head, neck, renal, kidney, ovarian, prostate, colorectal, oesophageal, gynecological or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertropy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a compound of formula 1 or 2, or a pharmaceutically acceptable salt or hydrate thereof, and a pharmaceutically acceptable carrier.

The invention also relates to a pharmaceutical composition for the prevention of blastocyte implantation in a mammal which comprises a therapeutically effective amount of a compound of formula 1 or 2, or a pharmaceutically acceptable salt or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of formula 1 or 2, or a pharmaceutically acceptable salt or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula 1 or 2, or a pharmaceutically acceptable salt or hydrate thereof. In one embodiment, said method relates to the treatment of cancer such as brain, squamous cell, bladder, gastric, pancreatic, breast, head, neck, oesophageal, prostate, colorectal, lung, renal, kidney, ovarian, gynecological or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a compound of formula 1 or 2, or a pharmaceutically acceptable salt or hydrate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method of treating pancreatitis or kidney disease in a mammal which comprises administering to said mammal a therapeutically effective amount of a compound of formula 1 or 2, or a pharmaceutically acceptable salt or hydrate thereof.

The invention also relates to a method of preventing blastocyte implantation in a mammal which comprises administering to said mammal a therapeutically effective amount of a compound of formula 1 or 2, or a pharmaceutically acceptable salt or hydrate thereof.

The invention also relates to a method of treating diseases related to vasculogenesis or angiogenesis in a mammal which comprises administering to said mammal an effective amount of a compound of formula 1 or 2, or a pharmaceutically acceptable salt or hydrate thereof. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with the compounds of formulas 1 and 2, and the pharmaceutically acceptable salts and hydrates of said compounds, according to the methods of this invention include, for example, patients that have been diagnosed as having psoriasis, BPH, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. Said "alkyl" group may include an optional carbon-carbon double or triple bond where said alkyl group comprises at least two carbon atoms. It is understood that for cyclic moieties at least three carbon atoms are required in said alkyl group.

The term "alkoxy", as used herein, unless otherwise indicated, includes O-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

The term "5–10 membered heterocyclic" or "5–13 membered heterocyclic", as used herein, unless otherwise indicated, includes aromatic and non-aromatic heterocyclic groups containing one to four heteroatoms each selected from O, S and N, wherein each heterocyclic group has from 5–10 or 5–13 atoms in its ring system. The heterocyclic groups include benzo-fused ring systems and ring systems substituted with one or two oxo (=O) moieties such as pyrrolidin-2-one. An example of a 5 membered heterocyclic group is thiazolyl, an example of a 10 membered heterocyclic group is quinolinyl, and an example of a 13 membered heterocyclic group is a carbazole group. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include benzimidazolyl, benzofuranyl, and benzo[1,3]dioxolyl.

The phrase "pharmaceutically acceptable salt(s)", as used herein, unless otherwise indicated, includes salts of acidic or basic groups which may be present in the compounds of formulas 1 and 2. The compounds of formulas 1 and 2 that are basic in nature are capable of forming a wide variety of salts with various inorganic and organic acids. The acids that may be used to prepare pharmaceutically acceptable acid addition salts of such basic compounds of formulas 1 and 2 are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formulas 1 and 2 that are acidic in nature, are capable of forming base salts with various pharmacologically acceptable cations. Examples of such salts include the alkali metal or alkaline earth metal salts and particularly, the sodium and potassium salts.

Certain compounds of formulas 1 and 2 may have asymmetric centers and therefore exist in different enantiomeric forms. This invention relates to the use of all optical isomers and stereoisomers of the compounds of formulas 1 and 2 and mixtures thereof. The compounds of formulas 1 and 2 may also exist as tautomers. This invention relates to the use of all such tautomers and mixtures thereof.

Scheme 1

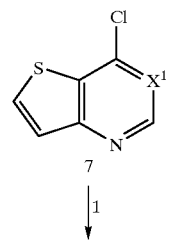

-continued

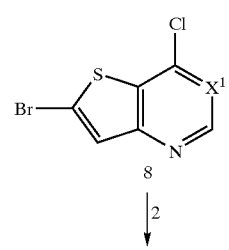

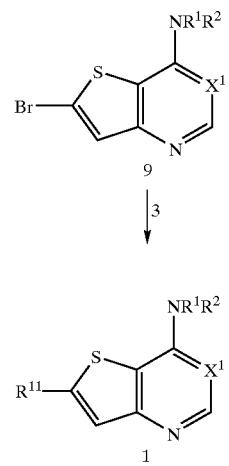

Scheme 2

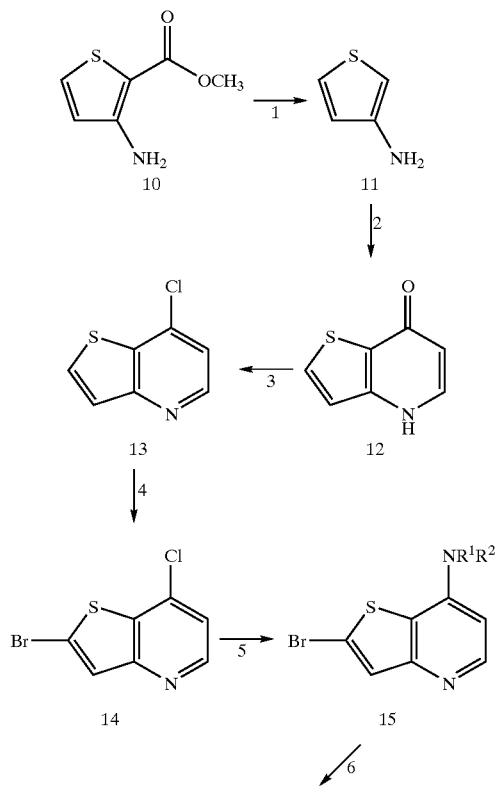

-continued

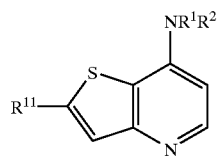

Scheme 3

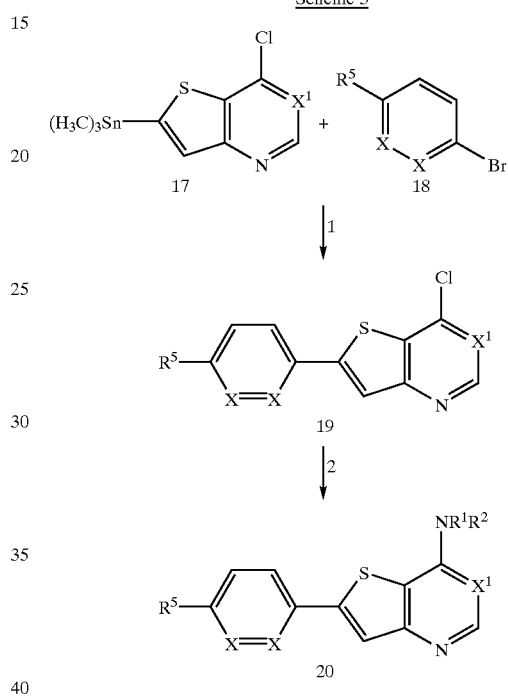

DETAILED DESCRIPTION OF THE INVENTION

The preparation of the compounds of the present invention is illustrated in the following Schemes 1–3.

The compounds of the present invention are readily prepared according to synthetic methods familiar to those skilled in the art. Scheme 1 illustrates a general synthetic procedure for preparing the compounds of the present invention. While Scheme 1 specifically illustrates the preparation of compounds of formula 1, it applies equally to the preparation of compounds of formula 2. The compound of formula 7 (in which $X^1$ is as defined above) may be prepared by one or more procedures described in published PCT international applications numbers WO 95/19774 (published Jul. 27, 1995), WO 95/19970 (published Jul. 27, 1995), and WO 97/13771 (published Apr. 17, 1997). In addition, 4-chlorothieno[3,2-d]pyrimidine is commercially available, such as from Maybridge Chemical Co. Ltd. A preferred method of preparing 4-chlorothieno[3,2-d]pyridine is described below with reference to steps 1–3 of Scheme 2. In step 1 of Scheme 1, the compound of formula 7 may be converted to the corresponding bromo derivative of formula 8 by treating the starting compound with lithium diisopropylamine or n-butyllithium, and then 1,2-dibromo-1,1,2,2-tetrafluoroethane or bromine in a non-polar solvent, such as tetrahydrofuran (THF), at a temperature of about −78° C. for a period of about 15 minutes to one-half hour and then gradually warming the mixture to room temperature (20–25° C.). In step 2 of Scheme 1, the compound of formula 8 may be coupled with a compound of formula $HNR^1R^2$, wherein $R^1$ and $R^2$ are as defined above, optionally in the presence of a base, such as pyridine, triethylamine or sodium hydride, and optionally in the presence of pyridine hydrochloride as a catalyst, under an inert atmosphere, such as dry nitrogen gas, in a solvent, such as a $C_1$–$C_6$ alcohol, dimethylformamide (DMF), 1,2-dichloroethane (DCE), N-methylpyrrolidin-2-one (NMP), chloroform, acetonitrile, THF, dimethylsulfoxide (DMSO), 1,4-dioxane or pyridine, or a mixture of two or more of the foregoing solvents, preferably a mixture of t-butyl alcohol and DCE, at a temperature of from ambient to reflux temperature, preferably 80–125° C., for a period of about 2 hours to 72 hours to provide the compound of formula 9. The foregoing reaction is preferably done in a sealed tube.

Where the compound of formula $HNR^1R^2$ is an optionally substituted indole or indoline moiety, such compounds can be prepared according to one or more methods known to those skilled in the art. Such methods are described in PCT international patent application publication number WO 95/23141, referred to above, and in W. C. Sumpter and F. M. Miller, "Heterocyclic Compounds with Indole and Carbazole Systems," in volume 8 of "The Chemistry of Heterocyclic Compounds", Interscience Publishers Inc., New York (1954). Optional substituents can be included as appropriate before or after the coupling step illustrated in Scheme 1. Prior to the coupling step, primary and secondary amino moieties (other than said amine of formula $HNR^1R^2$) are preferably protected using a nitrogen protecting group known to those skilled in the art. Such protecting groups and their use are described in T. W. Greene and P. G. M. Wuts, "Protective Groups in Organic Synthesis," Second Edition, John Wiley & Sons, New York, 1991.

In step 3 of Scheme 1, the compound of formula 9 may be converted to the compound of formula 1 by coupling the starting compound with a compound of the formula $R^{11}$—$B(OH)_2$ (wherein $R^{11}$ is as defined above) in the presence of 1,4-bis(diphenylphosphino)butane and a palladium catalyst, such as bis(benzonitrile)-palladium(II) chloride, a base, such as sodium or potassium carbonate, and a solvent, such as toluene, ethanol, THF, DMF, or dimethoxyethane (DME), preferably a mixture of toluene, ethanol and THF, at a temperature within the range of about 50–110° C. for a period of about 1 to 24 hours. This step is analogous to the Suzuki coupling procedure described in N. Miyaura, A. Suzuki, *Chem. Rev.* 1995, 95, 2457. In the alternative, steps 2 and 3 of Scheme 1 may be reversed. That is, the $R^{11}$ group may be introduced into the compound of formula 7 followed by the coupling of the resulting compound with the compound of formula $HNR^1R^2$ as described above. In another procedure, step 3 of Scheme 1 may be achieved by reacting the compound of formula 9 with a compound of the formula (trialkylstannyl)-$R^{11}$ (wherein $R^{11}$ is as defined above), such as (tributylstannyl)-$R^{11}$, in the presence of copper iodide and trans-benzyl(chloro)bis(triphenylphosphine)palladium(II) in DMF at a temperature of about 90° C. for a period of about 14 hours. The starting compound for this procedure, specifically (tributylstannyl)-$R^{11}$, may be prepared from $R^{11}$—Br by at least three separate procedures. In a first procedure, $R^{11}$—Br may be treated with (tributylstannyl)-chloride and n-butyllithium in THF or DMF to provide (tributylstannyl)-$R^{11}$. In a second procedure, $R^{11}$—Br may be treated with $Bu_3Sn$—$SnBu_3$, wherein Bu represents butyl, and sodium metal to provide (tributylstannyl)-$R^{11}$. And in a third procedure, $R^{11}$—Br may be treated with $Bu_3Sn$—$SnBu_3$, wherein Bu represents butyl, and $Pd(PPh_3)_4$, wherein Ph represents phenyl, in toluene to provide (tributylstannyl)-$R^{11}$.

Following or before step 3 of Scheme 1, the $R^{11}$ group may be modified to introduce one or more $R^5$ groups (wherein $R^5$ is as defined above). In a one preferred method, where $R^{11}$ is a phenyl group that includes an aldehyde group, the aldehyde may be converted to a preferred aminomethyl group. In this process, the starting compound that includes an aldehyde on the $R^{11}$ group is reacted with an amine of the formula $HNR^6R^7$ (wherein $R^6$ and $R^7$ are as defined above) in the presence of a reducing agent, such as sodium cyanoborohydride or sodium borohydride, in a solvent comprising acetic acid and ethanol or methanol at a temperature in the range of 0–100° C., preferably room temperature. This process converts the aldehyde to a moiety of the formula $R^6R^7NCH_2$—. Other methods of modifying the compounds of formula 1 will be obvious to those skilled in the art. The compounds of formula 2 are prepared in an analogous manner.

Scheme 2 illustrates a procedure for preparing the compounds of formula 1 wherein $X^1$ is CH. In step 1 of Scheme 2, the compound of formula 10 (3-amino-thiophene-2-carboxylic acid methyl ester) is dissolved in sodium hydroxide and refluxed for about 2 hours. The solution is then cooled to 0° C. and acidified to pH 5 with concentrated HCl at which time a precipitate will form. The precipitate is separated and treated with propanol and oxalic acid, and the solution is stirred at about 38° C. for approximately 45 minutes to provide the compound of formula 11 (thiophen-3-ylamine). In step 2 of Scheme 2, the compound of formula 11 is dissolved in triethyl orthoformate and stirred at room temperature until dissolution is complete. 2,2-Dimethyl-[1,3]dioxane-4,6-dione is then added portionwise at room temperature, with a precipitate forming upon completion of the addition. The mixture is then heated at 85° C. overnight. The resulting precipitate, which is an intermediate (2,2-dimethyl-5-(thiophen-3-ylaminomethylene)-[1,3]dioxane-4,6-dione), is then separated and washed. The intermediate is added to dowtherm A (heated to 260° C.), and the resulting mixture is heated for 30 minutes and then cooled to room temperature to provide the compound of formula 12. In step 3 of Scheme 2, the compound of formula 12 is added to oxalyl chloride in a mixture of methylene chloride and DMF and heated to reflux for approximately two hours to provide the compound of formula 13. The compound of formula 13 may be converted to the compound of formula 14 as described above with respect to step 1 of Scheme 1. The compound of formula 14 may be converted to the compound of formula 15 as described above with respect to step 2 of Scheme 1. The compound of formula 15 may be converted to the compound of formula 16 as described above with respect to step 3 of Scheme 1.

Scheme 3 illustrates an alternative method of coupling the $R^{11}$ group represented by the compound of formula 18, wherein each X moiety is CH or N and $R^5$ is as defined above, with the remainder the compound of formula 1 or 2, which remainder is illustrated as the compound of formula 17. While the compound of formula 17 corresponds in structure to the compound of formula 1, the procedure described with respect to Scheme 3 may be followed to prepare corresponding compounds of formula 2. In step 1 of Scheme 3, the compound of formula 17 is coupled with the compound of formula 18 in DMF in the presence of copper iodide and trans-benzyl(chloro)bis-(triphenylphosphine) palladium(II) at a temperature of about 90° C. for about 14 hours to provide the compound of formula 19. The compound of formula 19 may then be coupled with the compound of formula $HNR^1R^2$, wherein $R^1$ and $R^2$ are as defined above, as described above with respect to step 2 of Scheme 1 to provide the compound of formula 20.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formulas 1 and 2 that are basic in nature are capable of forming a wide variety of different salts with various inorganic and organic acids. Although such salts must be pharmaceutically acceptable for administration to animals, it is often desirable in practice to initially isolate the compound of formula 1 or 2 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formulas 1 and 2 that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formulas 1 and 2. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention are potent inhibitors of the erbB family of oncogenic and protooncogenic protein tyrosine kinases such as epidermal growth factor receptor (EGFR), erbB2, HER3, or HER4 and thus are all adapted to therapeutic use as antiproliferative agents (e.g., anticancer) in mammals, particularly in humans. The compounds of the present invention are also inhibitors of angiogenesis and/or vasculogenesis. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

The compounds of the present invention may also be useful in the treatment of additional disorders in which aberrant expression ligand/receptor interactions or activation or signalling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

The in vitro activity of the compounds of formulas 1 and 2 in inhibiting the receptor tyrosine kinase (and thus subsequent proliferative response, e.g., cancer) may be determined by the following procedure.

The activity of the compounds of formulas 1 and 2, in vitro, can be determined by the amount of inhibition of the phosphorylation of an exogenous substrate (e.g., $LyS_3$-Gastrin or polyGluTyr (4:1) random copolymer (I. Posner et al., *J. Biol. Chem.* 267 (29), 20638–47 (1992)) on tyrosine by epidermal growth factor receptor kinase by a test compound relative to a control. Affinity purified, soluble human EGF receptor (96 ng) is obtained according to the procedure in G. N. Gill, W. Weber, *Methods in Enzymology* 146, 82–88 (1987) from A431 cells (American Type Culture Collection, Rockville, Md.) and preincubated in a microfuge tube with EGF (2 $\mu$g/ml) in phosphorylation buffer+vanadate (PBV: 50 mM HEPES, pH 7.4; 125 mM NaCl; 24 mM $MgCl_2$; 100 $\mu$M sodium orthovanadate), in a total volume of 10 $\mu$l, for 20–30 minutes at room temperature. The test compound, dissolved in dimethylsulfoxide (DMSO), is diluted in PBV, and 10 $\mu$l is mixed with the EGF receptor/EGF mix, and incubated for 10–30 minutes at 30° C. The phosphorylation reaction is initiated by addition of 20 $\mu$l $^{33}$P-ATP/substrate mix (120 $\mu$M $Lys_3$-Gastrin (sequence in single letter code for amino acids, KKKGPWLEEEEEAYGWLDF), 50 mM Hepes pH 7.4, 40 $\mu$M ATP, 2 $\mu$Ci $\gamma$-[$^{33}$P]-ATP) to the EGFr/EGF mix and incubated for 20 minutes at room temperature. The reaction is stopped by addition of 10 $\mu$l stop solution (0.5 M EDTA, pH 8; 2 mM ATP) and 6 $\mu$l 2N HCl. The tubes are centrifuged at 14,000 RPM, 4° C., for 10 minutes. 35 $\mu$l of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$P] incorporated is measured by liquid scintillation counting. Incorporation in the absence of substrate (e.g., $lys_3$-gastrin) is subtracted from all values as a background and percent inhibition is calculated relative to controls without test compound present. Such assays, carried out with a range of doses of test compounds, allow the determination of an approximate $IC_{50}$ value for the in vitro inhibition of EGFR kinase activity.

The activity of the compounds of formulas 1 and 2, in vivo, can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", *Cancer Res.*, 35, 2434–2439 (1975) and Corbett, T. H., et al., "A Mouse Colon-tumor Model for Experimental Therapy", *Cancer Chemother. Rep.* (Part 2)", 5, 169–186 (1975), with slight modifications. Tumors are induced in the left flank by s.c. injection of $1 \times 10^6$ log phase cultured tumor cells (human MDA-MB-468 breast or human HN5 head and neck carcinoma cells) suspended in 0.10 ml RPMI 1640. After sufficient time has elapsed for the tumors to become palpable (2–3 mm in diameter) the test animals (athymic mice) are treated with active compound (formulated by dissolution in DMSO typically at a concentration of 50 to 100 mg/mL followed by 1:9 dilution into saline or, alternatively, 1:9 dilution into 0.1% Pluronic™ P105 in 0.9% saline) by the intraperitoneal (ip) or oral (po) routes of administration twice daily (i.e., every 12 hours) for 5 consecutive days. In order to determine an anti-tumor effect, the tumor is measured in millimeters with Vernier calipers across two diameters and the tumor size (mg) is calculated using the formula: Tumor weight=(length×[width]$^2$)/2, according to the methods of Geran, R. I., et al. "Protocols for Screening Chemical Agents and Natural Products Against Animal Tumors and Other Biological Systems", Third Edition, *Cancer Chemother. Rep.*, 3, 1–104 (1972). Results are expressed as percent inhibition, according to the formula: Inhibition (%)=(TuW$_{control}$–TuW$_{test}$)/TuW$_{control}$×100%. The flank site of tumor implantation provides reproducible dose/response effects for a variety of chemotherapeutic agents, and the method of measurement (tumor diameter) is a reliable method for assessing tumor growth rates.

Other methods of assessing the activity of the compounds of the present invention are referred to in PCT international application publication number WO 95/21613 (published Aug. 17, 1995) which incorporated herein by reference.

The in vitro activity of the compounds of formulas 1 and 2 in inhibiting the KDR/VEGF receptor may be determined by the following procedure.

The ability of the compounds of the present invention to inhibit tyrosine kinase activity may be measured using a recombinant enzyme in an assay that measures the ability of compounds to inhibit the phosphorylation of the exogenous substrate, polyGluTyr (PGT, Sigma™, 4:1). The kinase domain of the human KDR/VEGF receptor (amino acids 805–1350) is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (0.625 $\mu$g PGT per well). Test compounds are diluted in dimethylsulfoxide (DMSO), and then added to the PGT plates so that the final concentration of DMSO in the assay is 1.6% (v/v). The recombinant enzyme is diluted in phosphorylation buffer (50 mM Hepes, pH 7.3, 125 mM NaCl, 24 mM MgCl$_2$). The reaction is initiated by the addition of ATP to a final concentration of 10 $\mu$M. After a 30 minute incubation at room temperature with shaking, the reaction is aspirated, and the plates are washed with wash buffer (PBS-containing 0.1% Tween-20). The amount of phosphorylated PGT is quantitated by incubation with a HRP-conjugated (HRP is horseradish peroxidase) PY-54 antibody (Transduction Labs), developed with TMB peroxidase (TMB is 3,3',5,5'-tetramethylbenzene), and the reaction is quantitated on a BioRad™ Microplate reader at 450 nM. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit KDR tyrosine kinase activity for the full length protein that exists in a cellular context, the porcine aortic endothelial (PAE) cells transfected with the human KDR (Waltenberger et al., J. Biol. Chem. 269:26988, 1994) may be used. Cells are plated and allowed to attach to 96-well dishes in the same media (Ham's F12) with 10% FBS (fetal bovine serum). The cells are then washed, re-fed with serum depleted media that contains 0.1% (v/v) bovine serum albumin (BSA), and allowed to incubate for 24 hours. Immediately prior to dosing with compound, the cells are re-fed with the serum depleted media (without BSA). Test compounds, dissolved in DMSO, are diluted into the media (final DMSO concentration 0.5% (v/v)). At the end of a 2 hour incubation, VEGF$_{165}$ (50 ng/ml final) is added to the media for an 8 minute incubation. The cells are washed and lysed in HNTG buffer (20 mM Hepes, pH 7.5, 150 mM NaCl, 0.2% Triton™ X-100, 10% glycerol, 0.2 mM PMSF (phenymethylsulfonyl fluoride), 1 $\mu$g/ml pepstatin, 1 $\mu$g/ml leupeptin, 1 $\mu$g/ml aprotonin, 2 mM sodium pyrophosphate, 2 mM sodium orthovanadate). The extent of phosphorylation of KDR is measured using an ELISA assay. The 96-well plates are coated with 1 $\mu$g per well of goat anti-rabbit antibody. Unbound antibody is washed off the plate and remaining sites are blocked with Superblock buffer (Pierce) prior to addition of the anti-flk-1 C-20 antibody (0.5 $\mu$g per plate, Santa Cruz). Any unbound antibody is washed off the plates prior to addition of the cell lysate. After a 2 hour incubation of the lysates with the flk-1 antibody, the KDR associated phosphotyrosine is quantitated by development with the HRP-conjugated PY-54 antibody and TMB, as described above. The ability of the compounds to inhibit the VEGF-stimulated autophosphorylation reaction by 50%, relative to VEGF-stimulated controls is reported as the $IC_{50}$ value for the test compound.

The ability of the compounds to inhibit mitogenesis in human endothelial cells is measured by their ability to inhibit $^3$H-thymidine incorporation into HUVE cells (human umbilical vein endothelial cells, Clonetics™). This assay has been well described in the literature (Waltenberger J et al. J. Biol. Chem. 269: 26988, 1994; Cao Y et al. J. Biol. Chem. 271: 3154, 1996). Briefly, 10$^4$ cells are plated in collagen-coated 24-well plates and allowed to attach. Cells are re-fed in serum-free media, and 24 hours later are treated with various concentrations of compound (prepared in DMSO, final concentration of DMSO in the assay is 0.2% v/v), and 2–30 ng/ml VEGF$_{165}$. During the last 3 hours of the 24 hour compound treatment, the cells are pulsed with $^3$H thymidine (NEN, 1 $\mu$Ci per well). The media are then removed, and the cells washed extensively with ice-cold Hank's balanced salt solution, and then 2 times with ice cold trichloroacetic acid (10% v/v). The cells are lysed by the addition of 0.2 ml of 0.1 N NaOH, and the lysates transferred into scintillation vials. The wells are then washed with 0.2 ml of 0.1 N HCl, and this wash is then transferred to the vials. The extent of $^3$H thymidine incorporation is measured by scintillation counting. The ability of the compounds to inhibit incorporation by 50%, relative to control (VEGF treatment with DMSO vehicle only) is reported as the IC$_{50}$ value for the test compound.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; antimetabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences,* Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations.

EXAMPLE 1

A. 3-Formylamino-thiophene-2-carboxylic Acid Methyl Ester

To a solution of 3-amino-thiophene-2-carboxylic acid methyl ester (25 g, 159 mmol) in 125 mL of formic acid was added ammonium acetate (15.9 g, 207 mmol). The reaction mixture was heated to reflux for 3 hours after which time the solution was cooled to room temperature (20–25° C.). The solid that formed was filtered, washed with water, and dried in vacuo to afford 25.4 g (86%) of 3-formylamino-thiophene-2-carboxylic acid methyl ester. $^1$H NMR (400 MHz, DMSO) d 10.2 (s, 1H), 8.35 (s, 3H), 7.92 (d, 1H), 7.91 (d, 1H), 3.76 (s, 3H). LC-MS: 186 (MH$^+$); HPLC RT: 2.81 minutes.

B. 3H-Thieno[3,2-d]pyrimidin-4-one

In a 125 mL round-bottomed flask 3-formylamino-thiophene-2-carboxylic acid methyl ester (5 g, 27.0 mmol), ammonium formate (5.11 9, 81.0 mmol), and formamide (6.40 mL, 162 mmol) were combined and heated at 140° C. After 10 hours the reaction mixture was cooled to room temperature and filtered. The crystalline solid was washed with water and dried in vacuo to afford 2.96 g (72%) of 3H-thieno[3,2-d]pyrimidin-4-one. $^1$H NMR (400 MHz, DMSO) d 8.10 (m, 2H), 7.34 (m, 1H). LC-MS: 153 (MH'); HPLC RT: 1.21 minutes.

C. 4-Chloro-thieno[3,2-d]pyrimidine

Dimethyl formamide (6.6 mL, 85.4 mmol) in 50 mL of dichloroethane was cooled to 0° C. and oxalyl chloride (62 mL, 124 mmol, 2M in dichloromethane) was added slowly over several minutes forming a white gel. 3H-thieno[3,2-d] pyrimidin-4-one (5.90 g, 38.8 mmol) was added and the reaction mixture was heated to reflux. After 2.5 hours the mixture was cooled to room temperature and poured into water. The product was extracted into dichloromethane (3×100 mL), dried over sodium sulfate, and concentrated in vacuo to afford 5.01 g (76%) of 4-chloro-thieno[3,2-d]pyrimidine. $^1$H NMR (400 MHz, DMSO) d 8.99 (s, 1H), 8.55 (d, 1H), 7.71 (d, 1H). LC-MS: 171 (MH$^+$); HPLC RT: 2.85 minutes.

D. 6-Bromo-4-chloro-thieno[3,2-d]pyrimidine

In a 250 mL round-bottomed flask 65 mL of tetrahydrofuran and lithium diisopropylamine (18.5 mL, 37 mmol, 2M in tetrahydrofuran) were cooled to −78° C. 4-chloro-thieno[3,2-d]pyrimidine (5.26 g, 31 mmol) was dissolved in 37 mL of tetrahydrofuran and slowly added to the reaction mixture over 5 minutes, After 20 minutes 1,2-dibromo-1,1,2,2-tetrafluoroethane (4.05 mL, 34 mmol) was added slowly to the solution of the anion. The temperature was maintained at −78° C. for 20 minutes then warmed to room temperature for 2 hours. The reaction mixture was poured into water and extracted with chloroform (3×100 mL), dried over sodium sulfate, and dried in vacuo to afford 7.70 g (99%) of 6-bromo-4-chloro-thieno[3,2-d]pyrimidine. $^1$H NMR (400 MHz, DMSO) d 8.97 (s, 1H), 8.01 (s, 1H). LC-MS: 249, 251 (MH$^+$); HPLC RT: 4.04 minutes.

E. (6-Bromo-thieno[3,2-d]pyrimidin-4-yl)-(1H-indol-5-yl)-amine

6-Bromo-4-chloro-thieno[3,2-d]pyrimidine (7.73 g, 31 mmol) was dissolved in 50 mL of dichloroethane and 50 mL of t-butyl alcohol, and 5-aminoindole (4.09 g, 31 mmol) were added. The reaction mixture was refluxed for 14 hours, cooled to room temperature, and concentrated in vacuo to afford 13.02 g of (6-bromo-thieno[3,2-d]pyrimidin-4-yl)-(1H-indol-5-yl)-amine. The crude material was used without further purification (83% purity). $^1$H NMR (400 MHz, DMSO) d 11.1 (s, 1H), 9.62 (s, 1H), 8.38 (s, 1H), 7.63 (s, 1H), 7.49 (s, 1H), 7.35 (m, 2H), 7.10 (d, 1H), 6.40 (s, 1H); LC-MS: 345, 347 (MH$^+$); HPLC RT: 3.77 minutes.

EXAMPLE 2

(1H-indol-5-yl)-(6-phenyl-thieno[3,2-d]pyrimidin-4-yl)-amine

A mixture of 1,4-bis(diphenylphosphino)butane (50 mg, 0.12 mmol) and bis(benzonitrile)-palladium(ii) chloride (45 mg, 0.12 mmol) were suspended in 12 mL of toluene and nitrogen was bubbled through the solution for 30 seconds. The solution was stirred for 20 minutes and (6-bromo-thieno[3,2-d]pyrimidin-4-yl)-(1H-indol-5-yl)-amine (400 mg, 1.16 mmol), phenylboronic acid (283 mg, 2.32 mmol), sodium carbonate (2.32 mL, 2.32 mmol, 1M aqueous), 16 mL tetrahydrofuran, and 6 mL of ethanol were added. Nitrogen was bubbled through the solution for 60 seconds and the mixture was heated to 85° C. After 14 hours the reaction mixture was cooled to room temperature and the pH was adjusted to 7 by addition of aqueous 1N hydrochloric acid. The material was then concentrated to dryness and chromatographed through silica gel eluting with 1–5% methanol:dichlormethane to afford 194 mg (49%) of (1H-indol-5-yl)-(6-phenyl-thieno[3,2-d]pyrimidin-4-yl)-amine. $^1$H NMR (400 MHz, DMSO) d 11.1 (s, 1H), 9.73 (s, 1H), 8.49 (s, 1H), 7.79 (m, 4H), 7.46 (m, 4H), 7.25 (d, 1H), 6.43 (s, 1H); LC-MS: 343 (MH+); HPLC RT: 4.71 minutes.

EXAMPLE 3

[6-(4-Chloro-phenyl)-thieno[3,2-d]pyrimidin-4-yl]-(1H-indol-5-yl)-amine

The title compound was prepared from p-chlorobenzeneboronic acid and (6-bromo-thieno[3,2-d]pyrimidin-4-yl)-(1H-indol-5-yl)-amine by a procedure analogous to example 2. $^1$H NMR (400 MHz, DMSO) d 11.4 (s, 1H), 8.86 (s, 1H), 7.58 (m, 9H), 7.21 (d, 1H), 6.50 (s, 1H). M.P. 190–210° C.; LC-MS: 377 (MH$^+$); HPLC RT: 5.32 minutes.

EXAMPLE 4

[6-(4-Fluoro-phenyl)-thieno[3,2-d]pyrimidin-4-yl]-(1H-indol-5-yl)-amine

The title compound was prepared from p-fluorobenzeneboronic acid and (6-bromo-thieno[3,2-d]pyrimidin-4-yl)-(1H-indol-5-yl)-amine by a procedure analogous to example 2. $^1$H NMR (400 MHz, DMSO) d 11.4 (s, 1H), 8.82 (s, 1H), 7.79 (m, 4H), 7.41 (m, 5H), 7.21 (d, 1H). 6.50 (s, 1H), M.P. 193–205° C.; LC-MS: 361 (MH+); HPLC RT: 4.88 minutes.

EXAMPLE 5

(1H-Indol-5-yl)-[6-(4-methoxy-phenyl)-thieno[3,2-d]pyrimidin-4-yl]-amine

The title compound was prepared from p-methoxybenzeneboronic acid and (6-bromo-thieno[3,2-d]pyrimidin-4-yl)-(1H-indol-5-yl)-amine by a procedure analogous to example 2. $^1$H NMR (400 MHz, DMSO) d 11.4 (s, 1H),11.2 (s, 1H), 8.81 (s, 1H), 7.55 (m, 6H), 7.20 (d, 1H). 7.05 (m, 2H), 6.50 (s, 1H), 3.79 (s, 3H). M.P. 150–180° C.; LC-MS: 373 (MH$^+$); HPLC RT: 4.45 minutes.

EXAMPLE 6

(1H-Indol-5-yl)-(6-p-tolyl-thieno[3,2-d]pyrimidin-4-yl)-amine

The title compound was prepared from p-methylbenzeneboronic acid and (6-bromo-thieno[3,2-d]pyrimidin-4-yl)-(1H-indol-5-yl)-amine by a procedure analogous to example 2. $^1$H NMR (400 MHz, DMSO) d 11.1 (s, 1H), 9.50 (s, 1H), 8.41 (s, 1H), 7.71 (d, 2H), 7.59 (s, 2H), 7.24 (m, 5H), 6.38 (s, 1H), 2.28 (s, 3H). M.P. 200–220° C.; LC-MS: 357 (MH$^+$); HPLC RT: 4.57 minutes.

EXAMPLE 7

4-[4-(1H-Indol-5-ylamino)-thieno[3,2-d]pyrimidin-6-yl]-benzaldehyde

The title compound was prepared from p-formylbenzeneboronic acid and (6-bromo-thieno[3,2-d]pyrimidin-4-yl)-(1H-indol-5-yl)-amine by a procedure analogous to example 2. $^1$H NMR (400 MHz, DMSO) d 11.2 (s, 1H), 9.95 (s, 1H), 8.85 (s, 1H), 7.90 (m, 6H), 7.75 (s, 1H), 7.46 (m, 3H), 7.20 (d, 1H), 6.49 (s, 1H), 2.28 (s, 3H), LC-MS: 371 (MH$^+$); HPLC RT: 4.10 minutes.

EXAMPLE 8

(1H-indol-5-yl)-(6-thiophen-3-yl-thieno[3,2-d]pyrimidin-4-yl)-amine

The title compound was prepared from thiophene-3-boronic acid and (6-bromo-thieno[3,2-d]pyrimidin-4-yl)-(1H-indol-5-yl)-amine by a procedure analogous to example 2. $^1$H NMR (400 MHz, DMSO) d 11.4 (s, 1H), 11.2 (s, 1H), 8.86 (s, 1H), 8.10 (s, 1H), 7.70 (m, 3H), 7.46 (m, 3H), 7.21 (d, 1H), 6.49 (s, 1H), M.P. 178–189° C.; LC-MS: 349 (MH$^+$) HPLC RT 4.05 minutes.

EXAMPLE 9

(1H-Indol-5-yl)-[6-(4-methylsulfanyl-phenyl)-thieno[3,2-d]pyrimidin-4-yl]-amine

The title compound was prepared from 4-(methylthio)benzeneboronic acid and (6-bromo-thieno[3,2-d]pyrimidin-4-yl)-(1H-indol-5-yl)-amine by a procedure analogous to example 2. $^1$H NMR (400 MHz, DMSO) d 11.4 (s, 1H), 11.2 (s, 1H), 8.82 (s, 1H), 7.76 (d, 2H), 7.76 (d, 2H), 7.61 (s, 2H), 7.51 (m, 2H), 7.35 d, 2H), 7.22 (d, 1H), 6.50 (s, 1H), 2.49 (s, 3H), M.P. 163–178° C.; LC-MS 389 (MH$^+$); HPLC RT: 4.73 minutes.

EXAMPLE 10

(1H-Indol-5-yl)-[6-(3-nitro-phenyl)-thieno[3,2-d]pyrimidin-4-yl]-amine

The title compound was prepared from 3-nitrobenzeneboronic acid and (6-bromo-thieno[3,2-d]pyrimidin-4-yl)-(1H-indol-5-yl)-amine by a procedure analogous to example 2. $^1$H NMR (400 MHz, DMSO) d 11.3 (s, 2H), 8.83 (s, 1H), 8.47 (s, 1H), 8.31 (m, 1H), 8.05 (m, 2H), 7.77 (m, 2H), 7.47 (m, 2H), 7.25 (m, 1H), 6.50 (s, 1H). M.P. 175–183° C.; LC-MS: 388 (MH$^+$); HPLC RT: 4.80 minutes.

EXAMPLE 11

(1H-Indol-5-yl)-[6-(4-trifluoromethyl-phenyl)-thieno[3,2-d]pyrimidin-4-yl-amine

The title compound was prepared from 3-trifluoromethylbenzeneboronic acid and (6-bromo-thieno[3,2-d]pyrimidin-4-yl)-(1H-indol-5-yl)-amine by a procedure analogous to example 2. M.P. 181–194° C.; LC-MS: 411 (MH$^+$); HPLC RT: 4.88 minutes.

EXAMPLE 12

[6-(3-Chloro-4-fluoro-phenyl)-thieno[3,2-d]pyrimidin-4-yl]-(1H-indol-5-yl)-amine The title compound was prepared from 3-chloro-4-fluoromethylbenzeneboronic acid and (6-bromo-thieno[3,2-d]pyrimidin-4-yl)-(1H-indol-5-yl)-amine by a procedure analogous to example 2. M.P. 175–183° C.; LC-MS: 395 (MH$^+$); HPLC RT: 5.33 minutes.

EXAMPLE 13

[6-(4-Ethyl-phenyl)-thieno[3,2-d]pyrimidin-4-yl]-(1H-indol-5-yl)-amine

The title compound was prepared from 4-ethylbenzeneboronic acid and (6-bromo-thieno[3,2-d]pyrimidin-4-yl)-(1H-indol-5-yl)-amine by a procedure analogous to example 2. M.P. 171–182° C.; LC-MS: 371 (MH$^+$); HPLC RT: 5.13 minutes.

EXAMPLE 14

(1H-Indol-5-yl)-[6-(4-thiophen-2-yl-phenyl)-thieno[3,2-d5pyrimidin-4-yl]-amine

The title compound was prepared from thiophene-2-boronic acid and (6-bromo-thieno[3,2-d]pyrimidin-4-yl)-(1H-indol-5-yl)-amine by a procedure analogous to example 2. M.P. 165–178° C.; LC-MS: 349 (MH$^+$); HPLC RT: 4.55 minutes.

EXAMPLE 15

(1H-Indol-5-yl)-[6-(3-methoxy-phenyl)-thieno[3,2-d]pyrimidin-4-yl]-amine

The title compound was prepared from 3-methoxybenzeneboronic acid and (6-bromo-thieno[3,2-d]pyrimidin-4-yl)-(1H-indol-5-yl)-amine by a procedure analogous to example 2. M.P. 60–168° C.; LC-MS: 373 (MH$^+$); HPLC RT: 4.75 minutes.

EXAMPLE 16

[6-(3,4-Dimethoxy-phenyl)-thieno[3,2-d]pyrimidin-4-yl]-(1H-indol-5-yl)-amine

The title compound was prepared from 3,4-dimethoxybenzeneboronic acid and (6-bromo-thieno[3,2-d]pyrimidin-4-yl)-(1H-indol-5-yl)-amine by a procedure analogous to example 2. M.P. 171–178° C.; LC-MS: 403 (MH$^+$); HPLC RT: 4.11 minutes.

EXAMPLE 17

3-{4-[4-(1H-Indol-5-ylamino)-thieno[3,2-d]pyrimidin-6-yl]-benzylamino}-propionic Acid Methyl Ester 3-Amino-propionic acid methyl ester (261 mg, 1.7 mmol) was dissolved in 3 mL of methyl alcohol and the pH was adjusted to 6 with concentrated acetic acid. 4-[4-(1H-Indol-5-ylamino)-thieno[3,2-d]pyrimidin-6-yl]-benzaldehyde (100 mg, 0.28 mmol) was added to the solution followed by sodium cyanoborohydride (11 mg, 0.17 mmol). After 14 hours the reaction mixture was poured into water and diluted with chloroform. The aqueous layer was separated and the pH was adjusted to 8.5 with 1N sodium hydroxide. The desired product was extracted from the aqueous layer with chloroform (3×20 mL), the combined organic extracts were dried over sodium sulfate, filtered, and dried in vacuo to afford 85 mg (41%) of 3-{4-[4-(1H-indol-5-ylamino)-thieno[3,2-d]pyrimidin-6-yl]-benzylamino}-propionic acid methyl ester. The product was converted to the HCl salt by stirring with 1 equivalent of 1N HCl in ether and the resulting yellow solid was dried in vacuo. M.P. 105–118° C.; LC-MS: 458 (MH$^+$); HPLC RT: 3.86 minutes.

EXAMPLE 18

N-{4-[4-(1H-Indol-5-ylamino)-thieno[3,2-d]pyrimidin-6-yl]-benzyl}-N',N'-dimethyl-ethane-1,2-diamine The title compound was prepared from N,N-dimethylethylenediamine and 4-[4-(1H-Indol-5-ylamino)-thieno[3,2-d]pyrimidin-6-yl]-benzaldehyde by a procedure analogous to example 17. M.P. 170–183° C.; LC-MS: 443 (MH$^+$); HPLC RT: 3.02 minutes.

EXAMPLE 19

N-(4-[4-(1H-Indol-5-ylamino)-thienol3,2-d]pyrimidin-6-yl]-benzyl)-N'-methyl-ethane-1,2-diamine The title compound was prepared from N-methylethylenediamine and 4-[4-(1H-Indol-5-ylamino)-thieno[3,2-d]pyrimidin-6-yl]-benzaldehyde by a procedure analogous to example 17.

The product was converted to the mesylate salt analogous to example 17 being converted to the HCl salt. M.P. 93–105° C.; LC-MS: 429 (MH$^+$); HPLC RT: 3.46 minutes.

EXAMPLE 20

(1H-Indol-5-yl)-(6-{4-[(2-methoxy-ethylamino)-methyl]-phenyl}-thieno[3,2-d]pyrimidin-4-yl)-amine The title compound was prepared from 2-aminoethanol and 4-[4-(1H-indol-5-ylamino)-thieno[3,2-d]pyrimidin-6-yl]-benzaldehyde by a procedure analogous to example 17. M.P. 170–190° C.; LC-MS: 416 (MH$^+$); HPLC RT: 2.91 minutes.

EXAMPLE 21

(1H-Indol-5-yl)-[6-(4-propylaminomethyl-phenyl)-thieno[3,2-d]pyrimidin-4-yl]-amine The title compound was prepared from propylamine and 4-(4-(1H-indol-5-ylamino)-thieno[3,2-d]pyrimidin-6-yl]-benzaldehyde by a procedure analogous to example 17. M.P. 190–205° C.; LC-MS: 414 (MH$^+$); HPLC RT: 4.15 minutes.

EXAMPLE 22

(1H-Indol-5-yl)-(6-{4-[(3-methoxy-propylamino)-methyl]-phenyl}-thieno[3,2-d]pyrimidin-4-yl)-amine The title compound was prepared from 3-methoxypropylamine and 4-[4-(1H-indol-5-ylamino)-thieno[3,2-d]pyrimidin-6-yl]-benzaldehyde by a procedure analogous to example 17. M.P. 160–175° C.; LC-MS: 444 (MH+); HPLC RT: 3.92 minutes.

EXAMPLE 23

(1H-Indol-5-yl)-(6-{4-[(2-piperazin-1-yl-ethylamino)-methyl]-phenyl}-thieno[3,2-d]pyrimidin-4-yl)-amine The title compound was prepared from N-(2-aminoethyl)-piperazine and 4-[4-(1H-indol-5-ylamino)-thieno[3,2-d]pyrimidin-6-yl]-benzaldehyde by the procedure analogous to example 17. M.P. 178–191° C.; LC-MS: 484 (MH$^+$); HPLC RT: 3.41 minutes.

EXAMPLE 24

(1H-Indol-5-yl)-(6-{4-[(2-morpholin-4-yl-ethylamino)-methyl]-phenyl}-thieno[3,2-d]pyrimidin-4-yl)-amine The title compound was prepared from N-(2-aminoethyl) morpholine and 4-[4-(1H-indol-5-ylamino)-thieno[3,2-d]pyrimidin-6-yl]-benzaldehyde by a procedure analogous to example 17. M.P. 100–111° C.; LC-MS: 485 (MH$^+$); HPLC RT: 4.23 minutes.

EXAMPLE 25

(1H-Indol-5-yl)-[6-(4-methylaminomethyl-phenyl)-thieno[3,2-d]pyrimidin-4-yl]-amine The title compound was prepared from methylamine and 4-[4-(1H-indol-5-ylamino)-thieno[3,2-d]pyrimidin-6-yl]-benzaldehyde by a procedure analogous to example 17. The product was converted to the mesylate salt analogous to example 17 being converted to the HCl salt. M.P. 140–147° C.; LC-MS: 386 (MH$^-$); HPLC RT: 3.54 minutes.

EXAMPLE 26

(1H-Indol-5-yl)-{6-[4-(4-methyl-piperazin-1-ylmethyl)-phenyl]-thieno[3,2-d]pyrimidin-4-yl}-amine The title compound was prepared from N-methylpiperazine and 4-[4-(1H-indol-5-ylamino)-thieno[3,2-d]pyrimidin-6-yl]-benzaldehyde by the procedure analogous to example 17.

The product was converted to the mesylate salt analogous to example 17 being converted to the HCl salt. M.P. 143–150° C.; LC-MS: 455 (MH$^+$); HPLC RT: 4.23 minutes.

EXAMPLE 27

2-{4-[4-(1H-indol-5-ylamino)-thieno[3,2-d]pyrimidin-6-yl]-benzylamino)-propane-1,3-diol The title compound was prepared from serinol and 4-[4-(1H-indol-5-ylamino)-thieno[3,2-d]pyrimidin-6-yl]-benzaldehyde by a procedure analogous to example 17. The product was converted to the mesylate salt analogous to example 17 being converted to the HCl salt. $^1$H NMR (400 MHz, MeOH) d 8.37 (s, 1H), 7.67 (s, 1H), 7.59 (d, 2H), 7.49 (s, 1H), 7.41 (m, 5H), 7.30 (d, 1H)7.19 (dd, 1H), 6.48 (d, 1H), 3.85s, 2H), 3.59 (m, 4H), 2.72 (m, 1H); LC-MS: 446 (MH$^+$); HPLC RT: 3.2 minutes.

EXAMPLE 28

3-{4-[4-(1H-Indol-5-ylamino)-thieno[3,2-d]pyrimidin-6-yl]-benzylamino}-propan-1-ol The title compound was prepared from 3-aminopropanol and 4-[4-(1H-indol-5-ylamino)-thieno[3,2-d]pyrimidin-6-yl]-benzaldehyde by a procedure analogous to example 17. The product was converted to the mesylate salt analogous to example 17 being converted to the HCl salt. $^1$H NMR (400 MHz, DMSO) d 11.1 (s, 1H), 9.54 (s, 1H), 8.44 (s, 1), 7.75 (dd, 4H), 7.42 (m, 4H), 7.23 (m, 1H), 6.41 (s, 1H), 3.67 (s, 2H), 3.43 (s, 2H), 3.30 (s, 2H), 1.54 (m, 2H); LC-MS: 430 (MH$^+$); HPLC RT: 3.34 minutes.

EXAMPLE 29

2-((2-Hydroxy-ethyl)-{4-[4-(1H-indol-5-ylamino)-thieno[3,2-d]pyrimidin-6-yl]-benzyl}-amino)-ethanol The title compound was prepared from 2-(2-hydroxy-ethylamino)-ethanol and 4-[4-(1H-indol-5-ylamino)-thieno[3,2-d]pyrimidin-6-yl]-benzaldehyde by a procedure analogous to example 17. The product was converted to the mesylate salt analogous to example 17 being converted to the HCl salt. M.P. 110–127° C.; LC-MS: 460 (MH$^+$); HPLC RT: 3.50 minutes.

EXAMPLE 30

2-(2-(4-[4-(1H-Indol-5-ylamino)-thieno[3,2-d]pyrimidin-6-yl]-benzylamino}-ethoxy)-ethanol The title compound was prepared from 2-(2-amino-ethoxy)-ethanol and 4-[4-(1H-indol-5-ylamino)-thieno[3,2-d]pyrimidin-6-yl]-benzaldehyde by a procedure analogous to example 17. The product was converted to the mesylate salt analogous to example 17 being converted to the HCl salt. M.P. 111–119° C.; LC-MS: 460 (MH$^+$); HPLC RT: 3.40 minutes.

EXAMPLE 31

2-(2-{4-[4-(1H-indol-5-ylamino)-thieno[3,2-d]pyrimidin-6-yl]-benzylamino}-ethylamino)-ethanol The title compound was prepared from 2-(2-amino-ethylamino)-ethanol and 4-[4-(1H-indol-5-ylamino)-thieno

[3,2-dipyrimidin-6-yl]-benzaldehyde by a procedure analogous to example 17. The product was converted to the mesylate salt analogous to example 17 being converted to the HCl salt. M.P. 78–95° C.; LC-MS: 459 (MH+); HPLC RT: 3.74 minutes.

EXAMPLE 32

[6-(4-{[2-(4H-Imidazol-4-yl)-ethylamino]-methyl}-phenyl)-thieno[3,2-d]pyrimidin-4-yl]-(1H-indol-5-yl)-amine The title compound was prepared from histamine and 4-[4-(1H-indol-5-ylamino)-thieno[3,2-d]pyrimidin-6-yl]-benzaldehyde by a procedure analogous to example 17. The product was converted to the mesylate salt analogous to example 17 being converted to the HCl salt. $^1$H NMR (400 MHz, DMSO) d 11.1 (s, 1H), 9.61 (s, 1H), 8.47 (s, 1H), 7.83 (m, 3H), 7.66 (s, 1H), 7.57 (m, 2H), 7.38 (m, 2H), 7.24 (m, 1H), 6.95 (s, 1H), 6.42 (s, 1H), 4.22 (s, 2H), 3.15 (m, 2H)2.82 (m, 2H); LC-MS: 466 (MH+); HPLC RT: 3.76 minutes.

EXAMPLE 33

(1H-Indol-5-yl)-[6-(4-{[(thiophen-2-ylmethyl)-amino]-methyl}-phenyl)-thieno[3,2-d]pyrimidin-4-yl]-amine The title compound was prepared from C-thiophen-2-yl-methylamine and 4-[4-(1H-indol-5-ylamino)-thieno[3,2-d]pyrimidin-6-yl]-benzaldehyde by a procedure analogous to example 17. The product was converted to the mesylate salt analogous to example 17 being converted to the HCl salt. M.P.111–121° C.; LC-MS: 468 (MH+); HPLC RT: 4.44 minutes.

EXAMPLE 34

[6-(4-{[(Furan-2-ylmethyl)-amino]-methyl}-phenyl)-thieno[3,2-d]pyrimidin-4-yl]-(1H-indol-5-yl)-amine The title compound was prepared from C-furan-2-yl-methylamine and 4-[4-(1H-indol-5-ylamino)-thieno[3,2-d]pyrimidin-6-yl]-benzaldehyde by a procedure analogous to example 17. M.P. 125–134° C.; LC-MS: 452 (MH+); HPLC RT: 4.51 minutes.

EXAMPLE 35

1-(3-{4-[4-(1H-Indol-5-ylamino)-thieno[3,2-d]pyrimidin-6-yl]-benzylamino}-propyl)-pyrrolidin-2-one The title compound was prepared from 1-(3-amino-propyl)-pyrrolidin-2-one and 4-[4-(1H-indol-5-ylamino)-thieno[3,2-d)pyrimidin-6-yl]-benzaldehyde by a procedure analogous to example 17. M.P. 139–146° C.; LC-MS: 497 (MH+); HPLC RT: 4.01 minutes.

EXAMPLE 36

N-{4-[4-(1H-Indol-5-ylamino)-thieno[3,2-d]pyrimidin-6-yl]-benzyl}-N',N'-dimethyl-propane-1,3-diamine The title compound was prepared from N,N-dimethylproplenediamine and 4-[4-(1H-indol-5-ylamino)-thieno[3,2-d]pyrimidin-6-yl]-benzaldehyde by a procedure analogous to example 17. M.P. 148–160° C.; LC-MS: 457 (MH+); HPLC RT: 3.84 minutes.

EXAMPLE 37

(1H-Indol-5yl)-[6-(4-morpholin4-ylmethyl-phenyl)-thieno[3,2-d]pyrimidin-4-yl]-amine The title compound was prepared from morpholine and 4-[4-(1H-indol-5-ylamino)-thieno[3,2-d]pyrimidin-6-yl]-benzaldehyde by a procedure analogous to example 17. M.P. 141–152° C.; LC-MS: 442 (MH+); HPLC RT: 4.10 minutes.

EXAMPLE 38

(2-{4-[4-(1H-indol-5-ylamino)-thieno[3,2-d]pyrimidin-6-yl]-benzylamino}-acetylamino)-acetic acid ethyl ester The title compound was prepared from (2-amino-acetylamino)-acetic acid ethyl ester and 4-[4-(1H-indol-5-ylamino)-thieno[3,2-d]pyrimidin-6-yl]-benzaldehyde by a procedure analogous to example 17. M.P. 98–115° C.; LC-MS: 515 (MH+); HPLC RT: 3.88 minutes.

EXAMPLE 39

1-(4-{4-[4-(1H-Indol-5-ylamino)-thieno(3,2-d]pyrimidin-6-yl]-benzyl}-piperazin-1-yl-ethanone The title compound was prepared from 1-piperazin-1-yl-ethanone and 4-[4-(1H-indol-5-ylamino)-thieno[3,2-d]pyrimidin-6-yl]-benzaldehyde by a procedure analogous to example 17. M.P. 163–180° C.; LC-MS: 483 (MH+); HPLC RT: 4.24 minutes.

EXAMPLE 40

[6-(4-Cyclopropylaminomethyl-phenyl)-thieno[3,2-d]pyrimidin-4-yl]-(1H-indol-5-yl)-amine The title compound was prepared from cyclopropylamine and 4-[4-(1H-indol-5-ylamino)-thieno[3,2-d]pyrimidin-6-yl]-benzaldehyde by a procedure analogous to example 17. M.P. 176–180° C.; LC-MS: 412 (MH+); HPLC RT: 4.10 minutes.

EXAMPLE 41

2-{4-[4-(1H-indol-5-ylamino)-thieno[3,2-d]pyrimidin-6-yl]-benzylamino}-propan-1-ol The title compound was prepared from 2-amino-propan-1-ol and 4-[4-(1H-indol-5-ylamino)-thieno[3,2-d]pyrimidin-6-yl]-benzaldehyde by a procedure analogous to example 17. M.P. 160–175° C.; LC-MS: 444 (MH+); HPLC RT: 3.90 minutes.

EXAMPLE 42

(1H-Indol-5-yl)-{6-[4-(2-methoxymethyl-pyrrolidin-1-ylmethyl)-phenyl]-thieno[3,2-d]pyrimidin-4-yl}-amine The title compound was prepared from 2-methoxymethyl-pyrrolidine and 4-[4-(1H-indol-5-ylamino)-thieno[3,2-d]pyrimidin-6-yl]-benzaldehyde by a procedure analogous to example 17. M.P. 161–177° C.; LC-MS: 470 (MH+); HPLC RT: 4.55 minutes.

EXAMPLE 43

N-(2-{4-[4-(1H-Indol-5-ylamino)-thieno[3,2-d]pyrimidin-6-yl]-benzylamino}-ethyl)-acetamide The title compound was prepared from N-(2-amino-ethyl)-acetamide and 4-[4-(1H-indol-5-ylamino)-thieno[3,

EXAMPLE 44

1-{4-[4-(1H-Indol-5-ylamino)-thieno[3,2-d]
pyrimidin-6-yl]-benzyl}-piperidine-4-carboxylic
acid amide The title compound was prepared from piperidine-4-carboxylic acid amide and 4-[4-(1H-indol-5-ylamino)-thieno[3,2-d]pyrimidin-6-yl]-benzaldehyde by a procedure analogous to example 17. M.P. 198–205° C.; LC-MS: 483 (MH+); HPLC RT: 3.56 minutes.

EXAMPLE 45

N-{4-[4-(1H-Indol-5-ylamino)-thieno[3,2-d]
pyrimidin-6-yl]-benzyl}-N',N4-dimethyl-hexane-1,
6-diamine The title compound was prepared from N',N'-dimethyl-hexane-1,6-diamine amide and 4-[4-(1H-indol-5-ylamino)-thieno[3,2-d]pyrimidin-6-yl]-benzaldehyde by the procedure analogous to example 17. $^1$H NMR (400 MHz, DMSO) d; M.P. 134–148° C.; LC-MS: 499 (MH+); HPLC RT: 4.12 minutes.

EXAMPLE 46

Furan-2-yl-(4-{4-[4-(1H-indol-5-ylamino)-thieno[3,
2-d]pyrimidin-6-yl]-benzyl}-piperazin-1-yl)-
methanone The title compound was prepared furan-2-yl-piperazin-1-yl-methanone and 4-[4-(1H-indol-5-ylamino)-thieno[3,2-d]pyrimidin-6-yl]-benzaldehyde by a procedure analogous to example 17. $^1$H NMR (400 MHz, DMSO) d; M. P. 167–174° C.; LC-MS: 535 (MH+); HPLC RT: 5.24 minutes.

EXAMPLE 47

A. Thiophen-3-ylamine

3-Amino-thiophene-2-carboxylic acid methyl ester (25 g, 159 mmol) was dissolved in 160 mL of 2N sodium hydroxide and refluxed for 2 hours. The solution was cooled to 0° C. and acidified to pH 5 with concentrated HCl at which time a precipitate formed. The precipitate was washed with water and then dissolved in acetone, dried over magnesium sulfate, and concentrated to near dryness at room temperature. To the residue 50 mL of propanol and oxalic acid (15.8 g, 175 mmol) were added and the solution was stirred at 38° C. for 45 minutes. The mixture was cooled and ether was added. The precipitate that was formed was filtered, washed with ether, and dried to afford 16.7 g of crude material. The solid was suspended in 300 mL of water and the pH was adjusted to 9 with saturated aqueous ammonium hydroxide. The solution was extracted with methylene chloride (4×100 mL), dried over sodium sulfate, filtered, and concentrated in vacuo to afford 6.37 g (40%) of thiophen-3-ylamine.

B. 4H-Thieno[3,2-b]pyridin-7-one

Dimethyl-[1,3]dioxane-4,6-dione (5.0 g, 34.6 mmol) was combined with triethyl orthoformate (205 mL, 138 mmol) and stirred at 30° C. for 1 hour. Thiophen-3-ylamine (2.81 g, 28.3 mmol) was added in small portions at room temperature, at which time a white percipitate. The mixture was heated at 85° C. overnight. The reaction mixture was cooled to room temperature and isopropyl ether was added and the suspension was stirred for one hour. The precipitate was filtered off and washed with isopropyl ether and dried in vacuo. The intermediate was dissolved in methylene chloride and potassium carbonate was added and the suspension was stirred for 30 minutes. The solid was filtered off and the solution was concentrated to give 2,2-dimethyl-5-(thiophen-3-ylaminomethylene)-[1,3]dioxane-4,6-dione as the free base. In a single neck round bottom flask, dowtherm A (15 mL) was heated to 260° C. and 2,2-dimethyl-5-(thiophen-3-ylaminomethylene)-11,3]dioxane-4,6-dione was added in small portions. The mixture heated for 30 minutes and then was cooled to room temperature and isopropyl ether was added and the suspension was stirred for one hour. The precipitate was filtered off and washed with isopropyl ether and dried in vacuo to provide 3.43g (79%) of 4H-thieno[3,2-b]pyridin-7-one. $^1$H NMR (400 MHz, DMSO) d 7.93 (d, 1H), 7.79 (d, 1H), 7.21 (d, 1H), 5.99 (d, 1H); LC-MS: 152 (MH+); HPLC RT: 1.21.

D. 7-Chloro-thieno[3,2-b]pyridine

In a 250 mL round-bottomed flask 100 mL of methylene chloride and dimethylformamide (6.1 mL, 78.6 mmol) were combined and cooled to 0° C. Oxalyl chloride (57 mL, 114 mmol) was added dropwise over several minutes. 4H-Thieno[3,2-b]pyridin-7-one (5.4 g, 35.7 mmol) was added and the solution was heated to reflux. After 2 hours the flask was cooled to room temperature and the resulting solid was filtered and dried in vacuo to afford 6.29 g (100%) of 7-chloro-thieno[3,2-b]pyridine as a yellow solid. $^1$H NMR (400 MHz, DMSO) d 8.67 (d, 1H), 8.29 (d, 1H), 7.66 (d, 1H), 7.61 (d, 1H); LC-MS: 171 (MH+); HPLC RT: 4.19.

E. 2-Bromo-7-chloro-thieno[3,2-b]pyridine

A solution of 90 mL of tetrahydrofuran and diisopropylamine (4.6 mL, 32.9 mmol) were cooled to −78° C. and n-butyllithium (12.2 mL, 30.3 mmol) in hexane was added dropwise. The solution was heated to 0 ° C. for 10 minutes, recooled to −78° C., and 7-chloro-thieno[3,2-b]pyridine (4.29 g, 25.2 mmol) was added. The anion was stirred 10 minutes and 1,2-dibromo-1,1,2,2-tetrafluoroethane (3.3 mL, 27.8 mmol) was added. The solution was stirred an additional 20 minutes then allowed to warm to room temperature. After 1 hour the reaction mixture was poured into water and extracted with chloroform (3×100 mL). The combined organic portions were dried over magnesium sulfate, filtered, and dried to afford 4.65 g (74%) of 2-bromo-7-chloro-thieno[3,2-b]pyridine. $^1$H NMR (400 MHz, DMSO) d 8.64 (d, 1H), 7.91 (s, 1H), 7.65 (d, 1H); LC-MS: 250 (MH+); HPLC RT: 5.49.

F. (1H-Indol-5-yl)-(2-phenyl-thieno[3,2-b]pyridin-7-
yl)-amine

In a sealed tube 2-bromo-7-chloro-thieno[3,2-b]pyridine (1.01 g, 4.08 mmol) was dissolved in 15 mL of dichloroethane and 15 mL of t-butylalcohol. 5-Amino-indole (540 mg, 4.08 mmol) was added, the tube was sealed, and the contents were heated at 85° C. for 36 hours. The solution was cooled and filtered, the solid washed with methylene chloride, and dried in vacuo to afford 1.96 g of crude product. A portion of the material (100 mg, 0.29 mmol) was coupled with benzeneboronic acid in a procedure analogous to example 2 to afford 37.1 mg (38%) of (1H-indol-5-yl)-(2-phenyl-thieno[3,2-b]pyridin-7-yl)-amine. $^1$H NMR (400 MHz, DMSO) d 11.1 (s, 1H), 8.69 (s, 1H), 8.15 (d, 1H), 7.78 (m, 3H), 7.41

2-d]pyrimidin-6-yl]-benzaldehyde by a procedure analogous to example 17. M.P. 142–155° C.; LC-MS: 457 (MH+); HPLC RT: 3.35 minutes.

(m, 6H), 6.98 (d, 1H), 6.53 (d, 1H), 6.41 (s, 1H); LC-MS: 342 (MH⁺); HPLC RT: 4.81.

EXAMPLE 48

4-[7-(1H-Indol-5-ylamino)-thieno[3,2-b]pyridin-2-yl]-benzaldehyde

The title compound was prepared from 4-formylbenzeneboronic acid and (2-bromo-thieno[3,2-b]pyridin-7-yl)-(1H-indol-5-yl)-amine by a procedure analogous to example 17. ¹H NMR (400 MHz, DMSO) d 11.1 (s, 1H), 9.98 (s, 1H), 8.21 (d, 1H), 8.05 (s, 1H), 7.95 (s, 3H), 7.82 (d, 1H), 7.60 (m, 3H), 7.00 (d, 1H), 6.58 (s, 1H), 6.40 (s, 1H), LC-MS: 370 (MH⁺); HPLC RT: 4.83 minutes.

EXAMPLE 49

(1H-Indol-5-yl)-(2-thiophen-2-yl-thieno[3,2-b]pyridin-7-yl)-amine

The title compound was prepared from thiophene-2-boronic acid and (2-bromo-thieno[3,2-b]pyridin-7-yl)-(1H-indol-5-yl)-amine by a procedure analogous to example 17. ¹H NMR (400 MHz, DMSO) d 11.1 (s, 2H), 8.27 (d, 1H), 7.73 (s, 1H), 7.48 (m, 5H), 7.19 (m, 1), 7.03 (d, 1H), 6.50 (s, 1H); LC-MS: 348 (MH⁺); HPLC RT: 5.11 minutes.

EXAMPLE 50

(1H-Indol-5-yl)-[2-(4-methoxy-phenyl)-thieno[3,2-b]pyridin-7-yl]-amine

The title compound was prepared from 4-methoxybenzeneboronic acid and (2-bromo-thieno[3,2-b]pyridin-7-yl)-(1H-indol-5-yl)-amine by a procedure analogous to example 17. ¹H NMR (400 MHz, DMSO) d 11.3 (s, 1H), 10.6 (s, 1H), 8.21 (d, 1H), 7.65 (m, 5H), 7.00 (m, 5H), 6.43 (d, 1H), 3.80 (s, 3H); LC-MS: 372 (MH⁺); HPLC RT: 5.45 minutes.

EXAMPLE 51

(1H-Indol-5-yl)-[2-(4-methylsulfanyl-phenyl)-thieno[3,2-b]pyridin-7-yl]-amine

The title compound was prepared from 4-(methylthio)benzeneboronic acid and (2-bromo-thieno[3,2-b]pyridin-7-yl)-(1H-indol-5-yl)-amine by a procedure analogous to example 17. ¹H NMR (400 MHz, DMSO) d 11.4 (s, 1H), 10.6 (s, 1H), 8.30 (d, 1H), 7.53 (m, 9H), 7.05 (d, 1H), 6.43 (s, 1H), 2.48 (s, 3H); LC-MS: 388 (MH⁺); HPLC RT: 6.07 minutes.

EXAMPLE 52

[2-(4-Fluoro-phenyl)-thieno[3,2-b]pyridin-7-yl]-(1H-indol-5-yl)-amine

The title compound was prepared from 4-fluorobenzeneboronic acid and (2-bromo-thieno[3,2-b]pyridin-7-yl)-(1H-indol-5-yl)-amine by a procedure analogous to example 17. ¹H NMR (400 MHz, DMSO) d 11.4 (s, 1H), 10.7 (s, 1H), 8.28 (d, 1H), 7.50 (m, 9H), 7.05 (d, 1H), 6.49 (s, 1H); LC-MS: 360 (MH⁺); HPLC RT: 5.40 minutes.

EXAMPLE 53

2-{4-[7-(1H-Indol-5-ylamino)-thieno[3,2-b]pyridin-2-yl]-phenoxy}-ethanol

The title compound was prepared 4-[2-(tert-Butyl-dimethyl-silanyloxy)-ethoxy]-benzoic boronic acid and (2-bromo-thieno[3,2-b]pyridin-7-yl)-(1H-indol-5-yl)-amine by a procedure analogous to example 17. ¹H NMR (400 MHz, DMSO) d 11.4(s, 1H), 10.7 (s, 1H), 8.24 (d, 1H), 7.53 (m, 9H), 7.08 (m, 1H), 6.49 (s, 1H), 4.02 (t, 2H), 3.70 (t, 2H); LC-MS: 402 (MH⁺); HPLC RT: 3.95 minutes.

EXAMPLE 54

2-(2-{4-[7-(1H-Indol-5-ylamino)-thieno[3,2-b]pyridin-2-yl]-benzylamino}-ethoxy)-ethanol The title compound was prepared from 2-(2-aminoethoxy)-ethanol and 4-[7-(1H-indol-5-ylamino)-thieno[3,2-b]pyridin-2-yl]-benzaldehyde by a procedure analogous to example 17. LC-MS: 459 (MH⁺); HPLC RT: 3.48 minutes.

EXAMPLE 55

2-{4-[7-(1H-Indol-5-ylamino)-thieno[3,2-b]pyridin-2-yl]-benzylamino}-ethanol

The title compound was prepared from 2-aminoethanol and 4-[7-(1H-indol-5-ylamino)-thieno[3,2-b]pyridin-2-yl]-benzaldehyde by a procedure analogous to example 17. LC-MS: 415 (MH⁺); HPLC RT: 3.40 minutes.

EXAMPLE 56

1-{4-[7-(1H-Indol-5-ylamino)-thieno[3,2-b]pyridin-2-yl]-benzyl}-piperidine-4-carboxylic acid amide The title compound was prepared from piperidine-4-carboxylic acid amide and 4-[7-(1H-indol-5-ylamino)-thieno[3,2-b]pyridin-2-yl]-benzaldehyde by a procedure analogous to example 17. LC-MS: 482 (MH⁺); HPLC RT: 3.56 minutes.

EXAMPLE 57

N-{4-[7-(1H-indol-5-ylamino)-thieno[3,2-b]pyridin-2-yl]-benzyl}-N',N'-dimethyl-hexane-1,6-diamine The title compound was prepared from N,N-dimethyl-hexane-1,6-diamine and 4-[7-(1H-indol-5-ylamino)-thieno[3,2-b]pyridin-2-yl]-benzaldehyde by a procedure analogous to example 17. LC-MS: 498 (MH⁺); HPLC RT: 3.93 minutes.

EXAMPLE 58

2-({4-[7-(1H-Indol-5-ylamino)-thieno[3,2-b]pyridin-2-yl]-benzyl}-methyl-amino)-ethanol The title compound was prepared from methylaminoethanol and 4-[7-(1H-indol-5-ylamino)-thieno[3,2-b]pyridin-2-yl]-benzaldehyde by a procedure analogous to example 17. LC-MS: 429 (MH⁺); HPLC RT: 3.53 minutes.

EXAMPLE 59

(1H-Indol-5-yl)-(2-{4-[(2-piperazin-1-yl-ethylamino)-methyl]-phenyl}-thieno[3,2-b]pyridine-7-yl)-amine The title compound was prepared from 2-piperazin-1-yl-ethylamine and 4-[7-(1H-indol-5-ylamino)-thieno(3,2-b]pyridin-2-yl]-benzaldehyde by a procedure analogous to example 17. LC-MS: 483 (MH⁺); HPLC RT: 3.41 minutes.

EXAMPLE 60

(1H-Indol-5-yl)-(2-pyridin-2-yl-thieno[3,2-b]pyridin-7-yl)-amine

In a sealed tube (2-bromo-thieno[3,2-b]pyridin-7-yl)-(1H-indol-5-yl)-amine (150 mg, 0.29 mmol) and 2-(tributylstannyl)pyridine (118 mg, 1.1 mmol) were combined in 3 mL of dimethylformamide along with copper iodide (3 mg, 0.015 mmol). Nitrogen was bubbled through the solution and trans-benzyl(chloro)bis-(triphenylphosphine)palladium(II) (33 mg, 0.044 mmol) was added, the tube was sealed and heated to 90° C. After 14 hours the solution was cooled and concentrated to dryness. Chromatography on 15 g of silica gel with $CH_2Cl_2$/ MeOH (5–20%) afforded 30.3 mg (28%) of,the title compound. LC-MS: 343 (MH$^+$); HPLC RT: 3.94 minutes.

EXAMPLE 61

2-Methoxy-N-(4-phenyl)-N'-(6-phenyl-thieno[3,2-d] pyrimidin-4-yl)-benzene-1,4-diamine To 4-Chloro-6-phenyl-thieno[3,2-d]pyrimidine (150 mg, 0.608 mmol) in t-butanol(2.5 mL) and dichloroethane (2.5 mL) was added 2-Methoxy-N-(4-phenyl)-benzene-1,4-diamine (130 mg, 0.608 mmol), and the mixture was heated in an 80° C. oil bath overnight. The reaction was cooled to ambient temperature and isopropyl ether was added. The product was filtered of to provide a tan solid (200 mg, 78% yield). RP18-HPLC RT: 6.261 minutes; API MS: 424.52 (M+1); MP: 201–203° C.

EXAMPLE 62

N-(4-Methoxy-phenyl)-N'-(6-phenyl-thieno[3,2-d] pyrimidin-4-yl)-benzene-1,4-diamine To 4-Chloro-6-phenyl-thieno[3,2-d]pyrimidine (150 mg, 0.608 mmol) in t-butanol(2.5 mL) and dichloroethane (2.5 mL) was added N-(4-methoxyo-phenyl)-benzene-1,4-diamine (152 mg, 0.608 mmol), and the mixture was heated in an 80° C. oil bath overnight. The reaction was cooled to ambient temperature and isopropyl ether was added. The product was filtered of to provide a tan solid (248 mg, 96 % yield). RP18-HPLC RT: 6.228 minutes; API MS: 424.52 (M+1); MP: 210–211 C.

EXAMPLE 63

A. Preparation of N-m-Tolyl-benzene-1,4-diamine

To a mixture of 4-nitro-fluorobenzene (250 mg, 1.77mmol) and 3-methyl aniline (190 mg, 1.77mmol) in 4 mL of water in a sealed tube was added magnesium oxide (86 mg, 2.126 mmol). The suspension was stirred at 200° C. for 2 days. The reaction was cooled to ambient temperature and the suspension was diluted with water and filtered to remove insoluble material. The aqueous layer was extracted 3 times with ethyl acetate (50 mL) and the combined organic layers were washed with boronic acid (5%, 50 mL) and water, dried over magnesium sulfate and concentrated in vacuo to provide (4-Nitro-phenyl)-m-tolyl-amine (190 mg, 47% yield). ). RP18-HPLC RT: 7.020 minutes; API MS: 229.20 (M+1).

To a solution of (4-Nitro-phenyl)-m-tolyl-amine (180 mg, 0.788 mmol) in toluene (10 mL) was added 18 mg of palladium on carbon (10%) in a Parr flask. The mixture was hydrogenated at 35 psi with shaking for 12 hours and then filtered and concentrated in vacuo to provide N-(6-phenyl-thieno[3,2-d]pyrimidin-4-yl)-N'-m-tolyl-benzene-1,4-diamine in quantitative yield as a yellow solid. API MS: 199.20 (M+1).

B. N-(6-Phenyl-thieno[3,2-d]pyrimidin-4-yl)-N'-m-tolyl-benzene-1,4-diamine

Utilizing a procedure analogous to that described in Example 61, the title compound was prepared in 21% yield from N-m-Tolyl-benzene-1,4-diamine (230 mg, 1.16 mmol) and 4-chloro-6-phenyl-thieno[3,2-d]pyrimidine 250 mg, 1.16 mmol). RP18-HPLC RT: 7.432 minutes; API MS: 409.1 (M+1); MP: 170–171° C.

EXAMPLE 64

A. Preparation of N'-p-tolyl-benzene-1,4-diamine

To a mixture of 4-nitro-fluorobenzene (250 mg, 1.77 mmol) and 4-amino-toluene (195 mL, 1.77 mmol) in 4 mL of water in a sealed tube was added magnesium oxide (86 mg, 2.126mmol). The suspension was stirred at 200° C. for 2 days. The reaction was cooled to ambient temperature and the suspension was diluted with water and filtered to remove insoluble material. The aqueous layer was extracted 3 times with ethyl acetate (50 mL) and the combined organic layers were washed with boronic acid (5%, 50 mL) and water, dried over magnesium sulfate and concentrated in vacuo to provide (4-nitro-phenyl)-p-tolyl-amine (190 mg, 47% yield). ). API MS: 229.20 (M+1).

To a solution of (4-Nitro-phenyl)-p-tolyl-amine (180 mg, 0.788 mmol) in toluene (10 mL) was added 18 mg of palladium on carbon (10%) in a Parr flask. The mixture was hydrogenated at 35 psi with shaking for 12 hours and then filtered and concentrated in vacuo to provide N-(6-phenyl-thieno[3,2-d]pyrimidin-4-yl)-N'-p-tolyl-benzene-1,4-diamine in quantitative yield as a yellow solid. API MS: 199.20(M+1).

B. N-(6-Phenyl-thieno[3,2-d]pyrimidin-4-yl)-N'-p-tolyl-benzene-1,4-diamine

Utilizing a procedure analogous to that described in Example 61, the title compound was prepared in 27% yield from N-m-Tolyl-benzene-1,4-diamine (100 mg, 0.45 mmol) and 4-chloro-6-phenyl-thieno[3,2-d]pyrimidine 80 mg, 0.45 mmol). RP18-HPLC RT: 7.468 minutes; API MS: 409.1 (M+1); MP: 221–222 C.

EXAMPLE 65

A. Preparation of 2,3-Dimethoxy-N-(4-phenyl)-benzene-1,4-diamine

Following the procedure described in Example 63, this intermediate was prepared in 40% overall yield from 4-nitro-fluorobenzene (376 mg, 3.54mmol) and 4-amino-1, 2-dimethoxy-benzene (542 mg, 3.54mmol) followed by hydrogenation in ethanol. RP18-HPLC RT: 6.10 minutes; API MS: 245.10 (M+1).

B. N-(3,4-Dimethoxy-phenyl)-N'-(6-phenyl-thieno [3,2-d]pyrimidin-4-yl)-benzene-1,4-diamine Utilizing a procedure analogous to that described in Example 61, the title compound was prepared in 21% yield from added 2,3-dimethoxy-N-(4-phenyl)-benzene-1,4-diamine (191 mg, 0.696 mmol) and 4-chloro-6-phenyl-thieno[3,2-d]pyrimidine (172 mg, 0.696 mmol). RP18-HPLC RT: 6.512 minutes; API MS: 454.55 (M+1); MP: 160–161° C.

EXAMPLE 66

A. Preparation of N-(3-Methoxy-phenyl)-benzene-1, 4-diamine

Following the procedure described in Example 63, this intermediate was prepared in 53% overall yield from 4-nitro-fluorobenzene (199mg, 1.77 mmol) and 3-methoxyaniline (250 mg, 1.77 mmol) followed by hydrogenation in ethanol. API MS: 215.28 (M+1).

B. N-(3-Methoxy-phenyl )-N'-(6-phenyl-thieno[3,2-d]pyrimidin-4-yl)-benzene-1,4-diamine Utilizing a procedure analogous to that described in Example 61, the title compound was prepared in 17% yield from added N-(3-methoxy-phenyl)-benzene-1,4-diamine (100 mg, 0.405 mmol) and 4-chloro-6-phenyl-thieno[3,2-d]pyrimidine (100 mg, 0.405 mmol). RP18-HPLC RT: 6.833 minutes; API MS: 425.53 (M+1); MP: 189–191° C.

EXAMPLE 67

A. Preparation of N-(4-(N,N-dimethyl)-amine-phenyl)-benzene-1,4-diamine

Following the procedure described in Example 63, the title intermediate was prepared in 44% overall yield from 4-nitro-fluorobenzene (250mg, 1.77 mmol) and 4-(N,N-dimethyl)-amine-aniline (228 mg, 1.77 mmol) followed by hydrogenation in ethanol. RP18-HPLC RT: 5.25 minutes; API MS: 215.28 (M+1).

B. 4-(N,N-dimethylamine)-N-(4-phenyl)-N'-(6-phenyl-thieno[3,2-d]pyrimidin-4-yl)-benzene-1,4-diamine Utilizing a procedure analogous to that described in Example 61, the title compound was prepared in 31% yield from added N-(4-(N,N-dimethyl)-amine-phenyl)-benzene-1,4-diamine (100 mg, 0.405 mmol) and 4-chloro-6-phenyl-thieno[3,2-d]pyrimidine (93 mg, 0.405 mmol). RP18-HPLC RT: 7.056 minutes; API MS: 438.45 (M+1); MP: 198–199° C.

EXAMPLE 68

A. Preparation of 2-Methyl-5-aminoindole

To a mixture of 2-methyl-5-nitroindole (200 mg, 1.13 mmol) and palladium on carbon (20 mg, 10%) in 10 mL of ethanol was added hydrazine (100 mg, 3.4 mmol) and heated at 80° C. for 16 hours. The reaction mixture was filtered through celite and concentrated in vacuo to provide a red-brown solid which was used without further purification. RP18-HPLC RT: 1.278 minutes; API MS: 147.1 (M+1).

B. (2-Methyl-1H-indol-5-yl)-(6-phenyl-thieno[3,2-d]pyrimidin-4-yl)-amine

In a sealed tube 2-phenyl-7-chloro-thieno[3,2-b]pyrimidine (150 mg, 0.608 mmol) was dissolved in 15 mL of dichloroethane and 15 mL of t-butyl alcohol. 2-Methyl-5-aminoindole (89 mg, 0.608 mmol) was added, the tube was sealed, and the contents were heated at 85° C. for 36 hours. The solution was cooled and filtered, the solid washed with methylene chloride, and dried in vacuo to afford 123 mg (61% yield) of the title compound. RP18-HPLC RT: 5.407 minutes; API MS: 357.1 (M+1) MP: 218–220° C.

EXAMPLE 69

A. Preparation of 1-Benzenesulfonyl-1H-indol-5-yl amine

To a mixture of 5-nitroindole (30 g, 185 mmol) in dry THF (300 mL) was added potassium t-butoxide (24.26 g, 204 mmol). The reaction was stirred at room temperature for 30 minutes. Benzenesulfonyl chloride (28.33 g, 222 mmol) was added in one portion and the reaction changed color from clear black to an orange slurry. The reaction was stirred at room temperature for 24 hours. The reaction mixture was partitioned between water and ethyl acetate and the water layer was extracted 3 time with ethyl acetate. The organic extracts were combined and dried over magnesium sulfate and concentrated in vacuo. The crude residue was recrystallized from hexane to provide 50 g (91%) of the nitro intermediate. RP18-HPLC RT: 5.13 minutes.

The nitro intermediate was dissolved in 90 mL of THF and palladium on carbon (500 mg, 10%) was added. The mixture was hydrogenated at room temperature under 1.2 atmospheres of pressure. The reaction was filtered and concentrated in vacuo to provide the title compound as a yellow residue which was used without further purification. RP18-HPLC RT: 4.251 minutes.

B. Preparation of [1-benzenesulfonyl-1H-indol-5-yl]-(6-phenyl-thieno[3,2-d]pyrimidin-4-yl)-amine In a sealed tube 2-phenyl-7-chloro-thieno[3,2-b]pyrimidine (1000 mg, 4.05 mmol) was dissolved in 15 mL of dichloroethane and 15 mL of t-butylalcohol. 1-Benzenesulfonyl-1H-indol-5-yl amine (1100 mg, 4.05 mmol) was added, the tube was sealed, and the contents were heated at 85° C. for 36 hours. The solution was cooled and filtered, the solid washed with methylene chloride, and dried in vacuo to afford 1723 mg (89% yield) of the title compound. RP18-HPLC RT: 6.629 minutes; API MS: 483.45 (M+1).

C. [1-(2-Morpholin-4-yl-ethyl)-1H-indol-5-yl]-(6-phenyl-thieno[3,2-d]pyrimidin-4-yl-amine To a suspension of NaH (486 mg, 0.642 mmol) in dioxane was added [1-benzenesulfonyl-1H-indol-5-yl]-(6-phenyl-thieno[3,2-d]pyrimidin-4-yl)-amine (246 mg, 1.00 mmol) and the reaction was stirred for 30 minutes at room temperature. Hydroxyethyl morpholine (46 mg, 1.0 mmol) was added and the reaction was refluxed overnight. The reaction mixture was partitioned between water and ethyl acetate and the water layer was extracted 3 time with ethyl acetate. The organic extracts were combined and dried over magnesium sulfate and concentrated in vacuo. The crude residue was chromatographed on silica gel 1% methanol/methylene chloride to provide 26 mg (16%) of the title compound. RP18-HPLC RT: 5.586 minutes; API MS: 342.43 (M+1)) MP: 225–226 C.

EXAMPLE 70

[1-(3-Diethylamino-propyl)-1H-indol-5-yl]-(6-phenyl-thieno[3,2-d]pyrimidin-4-yl) -amine The title compound was prepared from [1-benzenesulfonyl-1H-indol-5-yl]-(6-phenyl-thieno[3,2-d]pyrimidin-4-yl )-amine (246 mg, 1.00 mmol) and diethylamino-propanol (120 mg, 0.939 mmol) by a procedure analogous to example 69. RP18-HPLC RT: 4.55 minutes; API MS: 455.63 (M+1) MP: 178–180° C.

EXAMPLE 71

A. Preparation of 2-phenyl-5-methyl-7-chloro-thieno[3,2-b]pyrimidine

To a solution of methyl 3-amino-5-phenylthiophene-2-carboxylate (1.0 g, 4.28 mmol) in 6 mL of acetonitrile was bubbled a dry stream of HCl gas for 30 minutes. The reaction was poured onto ice water and the pH was adjusted to 9 with ammonium hydroxide. The product was filtered and recrystallized from dioxane to provide product as a white solid.

In a 250 mL round-bottomed flask 100 mL of methylene chloride and dimethylformamide (0.247 mL, 3.19 mmol) were combined and cooled to 0° C. Oxalyl chloride (2.33 mL, 4.66 mmol) was added dropwise over several minutes. 2-Methyl-6-phenyl-4H-thieno[3,2-b]pyrimidin-7-one (353 mg, 1.45 mmol) was added and the solution was heated to reflux. After 2 hours the flask was cooled to room temperature and the resulting solid was filtered and dried in vacuo to afford 400 mg (100%) of 7-chloro-thieno[3,2-b]pyridine as a green solid. LC-MS: 261 (MH$^+$).

B. (1H-Indol-5-yl)-(2-methyl-6-phenyl-thieno[3,2-d] pyrimidin-4-yl)-amine

In a sealed tube 2-phenyl-5-methyl-7-chloro-thieno[3,2-b]pyrimidine (200 mg, 0.767 mmol) was dissolved in 15 mL of dichloroethane and 15 mL of t-butylalcohol. 1H-indol-5-yl amine (843 mg, 0.767 mmol) was added, the tube was sealed, and the contents were heated at 85° C. for 36 hours. The solution was cooled and filtered, the solid washed with methylene chloride, and dried in vacuo to afford 190 mg (52% yield) of the title compound. RP18-HPLC RT: 5.46 minutes; API MS: 356.47 (M+1) MP: 205–210° C.

EXAMPLE 72

N-(4-Methoxy-phenyl)-N'-(2-methyl-6-phenyl-thieno[3,2-d]pyrimidin-4-yl)-benzene-1,4-diamine The title compound was prepared from 2-phenyl-5-methyl-7-chloro-thieno[3,2-b]pyrimidine (200 mg, 0.767 mmol) and N-(4-methoxyo-phenyl)-benzene-1,4-diamine (843 mg, 0.767 mmol) by a procedure analogous to example 71. RP18-HPLC RT: 6.75 minutes; API MS: 438.58 (M+1) MP: 181–185 C.

EXAMPLE 73

A. Preparation of N-(6-Phenyl-thieno[3,2-d] pyrimidin-4-yl)-benzene-1,4-diamine

In a sealed tube 2-phenyl-7-chloro-thieno[3,2-b] pyrimidine(500 mg, 2.026 mmol) was dissolved in 15 mL of dichloroethane and 15 mL of t-butylalcohol. 4-nitroaniline (279 mg, 2.026 mmol) was added, the tube was sealed, and the contents were heated at 85° C. for 36 hours. The solution was cooled and filtered, the solid washed with methylene chloride, and dried in vacuo to afford 400 mg (57% yield) of the title compound. RP18-HPLC RT: 5.46.47607 minutes; API MS: 357.1348.38 (M+1) MP: 210–211° C.

To a mixture of (4-Nitro-phenyl)-(6-phenyl-thieno[3,2-d]pyrimidin-4-yl)-amine(400 mg, 1.48 mmol) and palladium on carbon (40 mg, 10%) in 10 mL of ethanol was added hydrazine (200 mg, 3.4 mmol) and heated at 80° C. for 16 hours. The reaction mixture was filtered through celite and concentrated in vacuo to provide a red-brown solid which was used without further purification. RP18-HPLC RT: 4.815 minutes; API MS: 319.38 (M+1).

B. N-(2-Benzyloxy-ethyl)-N'-(6-phenyl-thieno[3,2-d]pyrimidin-4-yl)-benzene-1,4-diamine The title compound was prepared from benzyloxy-acetaldehyde (12 mg, 0.079 mmol) and N-(6-Phenyl-thieno [3,2-d]pyrimidin-4-yl)-benzene-1,4-diamine (150 mg, 0.471 mmol) by a procedure analogous to example 17. RP18-HPLC RT: 7.062 minutes; API MS: 452.58 (M+1) MP: 201–203° C.

EXAMPLE 74

5-(6-Phenyl-thieno[3,2-d]pyrimidin-4-ylamino)-1H-indole-3-carbaldehyde

To a solution of (1H-Indol-5-yl)-(6-phenyl-thieno[3,2-d] pyrimidin-4-yl)-amine (481 mg, 1.4 mmol) in 3 mL of methylene chloride in a 3-neck flask with dropping funnel under nitrogen at 0° C. was added titanium tetrachloride (461 mL, 4.2 mmol) dropwise. The mixture was stirred for 30 minutes and then dichloromethoxy methane (380 mL, 4.2 mmol) was added dropwise. The reaction was warmed to room temperature and concentrated in vacuo. The resulting residue was pre-absorbed onto silica gel (10 gm) and purified by flash chromatography using a 5% methanol/methylene chloride to afford the title compound in 92% yield. RP18-HPLC RT: 4.80 minutes; API MS: 371.20 (M+1); MP: 174–175° C.

EXAMPLE 75

(3-Bromo-1H-indol-5-yl)-(6-phenyl-thieno[3,2-d]pyrimidin-4-yl)-amine

To a solution of (1H-Indol-5-yl)-(6-phenyl-thieno[3,2-d] pyrimidin-4-yl)-amine (150 mg, 0.438 mmol) in methylene chloride was added N-bromosuccinimide (86 mg, 0.482 mmol). The reaction mixture was stirred for 2 days at room temperature and then concentrated in vacuo. The orange residue was chromatographed by preparative reverse-phase HPLC using a 200 nM acetate buffer and acetonitrile gradient to afford pure product (17% yield). RP18-HPLC RT: 6.377 minutes; API MS: 371.2 (M+1); MP: 201–203° C.

EXAMPLE 76

N-(1H-Indol-3-ylmethyl)-N'-(6-phenyl-thieno[3,2-d]pyrimidin-4-yl)-benzene-1,4-diamine The title compound was prepared from 1H-indole-3-carbaldehyde(12 mg, 0.079 mmol) and N-(6-Phenyl-thieno [3,2-d]pyrimidin-4-yl)-benzene-1,4-diamine (150 mg, 0.471 mmol) by a procedure analogous to example 73. RP18-HPLC RT: 6.932 minutes; API MS: 448.20 (M+1) MP: 259–261° C.

EXAMPLE 77

N-(6-Bromo-thieno[3,2-d]pyrimidin-4-yl)-N'-(4-methoxy-phenyl)-benzene-1,4-diamine The title compound was from 2-bromo-7-chloro-thieno [3,2-b]pyridine (1.8 g, 7.25 mmol) and N-(4-methoxy-phenyl)-benzene-1,4-diamine (1.7 mg, 0.767 mmol) by a procedure analogous to example 1. RP18-HPLC RT: 5.75 minutes; API MS: 426.26 (M+1).

EXAMPLE 78

N-(4-Methoxy-phenyl)-N'-[6-(2-nitro-phenyl)-thieno [3,2-d]pyrimidin-4-yl]-benzene -1,4-diamine The title compound was prepared from 2-nitrobenzeneboronic acid and N-(6-Bromo-thieno[3,2-d] pyrimidin-4-yl)-N'-(4-methoxy-phenyl)-benzene-1,4- diamine by a procedure analogous to example 2. M.P. 228–237° C. ; LC-MS: 383.56 (MH⁺); HPLC RT: 6.885 minutes.

EXAMPLE 79

N-(4-Methoxy-phenyl )-N'-[6-(4-methoxy-phenyl )-thieno[3,2-d]pyrimid in-4-yl]-benzene-1,4-diamine The title compound was prepared from 2-methoxybenzeneboronic acid and N-(6-bromo-thieno[3,2-d]pyrimidin-4-yl)-N'-(4-methoxy-phenyl)-benzene-1,4-diamine by a procedure analogous to example 2. M.P. 159–169° C.; LC-MS: 454.31 (MH⁺); HPLC RT: 7.003 minutes.

EXAMPLE 80

N-(4-Methoxy-phenyl)-N'-[6-(6-methoxy-pyridin-3-yl)-thieno[3,2-d]pyrimidin-4-yl]-benzene-1,4-diamine The title compound was prepared from 2-methoxy-pyridyl-5-boronic acid and N-(6-bromo-thieno[3,2-d]pyrimidin-4-yl)-N'-(4-methoxy-phenyl)-benzene-1,4-diamine by a procedure analogous to example 2. M.P. 149–159° C.; LC-MS: 455.29 (MH⁺); HPLC RT: 6.747 minutes.

EXAMPLE 81

N-(4-Methoxy-phenyl)-N'-(6-thiophen-2-yl-thieno[3,2-d]pyrimidin-4-yl)-benzene-1,4-diamine The title compound was prepared from 2-thiophene boronic acid and N-(6-bromo-thieno[3,2-d]pyrimidin-4-yl)-N'-(4-methoxy-phenyl)-benzene-1,4-diamine by a procedure analogous to example 2. M.P. 231–40° C. ; LC-MS: 431 (MH⁺); HPLC RT: 6.740 minutes.

EXAMPLE 82

(3-Methyl-1H-indol-5-yl)-(6-phenyl-thieno[3,2-d]pyrimidin-4-yl)-amine

To a suspension of 5-(6-phenyl-thieno[3,2-d]pyrimidin-4-ylamino)-1H-indole-3-carbaldehyde (75 mg, 0.203 mmol) in 5 mL of methylene chloride was added zinc iodide (97 mg, 0.303) and sodium cyanoborohydride (97 mg, 1.522 mmol). The reaction mixture was refluxed for 24 hours and then cooled to ambient temperature and poured into an ice-cooled mixture of saturated ammonium chloride. The solution was then neutralized with 6N HCl and extracted with ethyl acetate (3×, 50 mL). The organic extracts were dried over magnesium sulfate and concentrated in vacuo. The residue was chromatographed using a Biotage Autoflash 40 system and 1% MeOH/CH₂Cl₂ to produce the title compound (22 mg, 31% yield). RP18-HPLC RT: 6.071 minutes; API MS: 357.10 (M+1); MP: 221–223° C.

EXAMPLE 83

N-(4-Methoxy-phenyl)-N'-[2-(3- nitro-phenyl)-thien[3,2-b]pyridin-7-yl]benzene-1,4-diamine The title compound was prepared from 2-nitrobenzene boronic acid and N-(6-bromo-thieno[3,2-d]pyrimidin-4-yl)-N'-(4-methoxy-phenyl)-benzene-1,4-diamine by a procedure analogous to example 2. M.P. 175–184° C.; LC-MS: 455.29 (MH⁺); HPLC RT: 6.646 minutes.

EXAMPLE 84

(7-Methoxy-1H-indol-5-yl)-(2-phenyl-thieno[3,2-b]pyridin-7-yl)-amine

The title compound was prepared according to a procedure that is analogous to the procedures described in the above examples.

EXAMPLE 85

N-(4-Methoxy-phenyl)-N'-thieno[3,2-d]pyrimidin-4-yl-benzene-1,4-diamine

The title compound was from 7-chloro-thieno[3,2-b]pyridine (3.65 g, 14.64 mmol) and N-(4-methoxy-phenyl)-benzene-1,4-diamine (3.13 g, 14.64 mmol) by a procedure analogous to example 1. RP18-HPLC RT: 6.070 minutes; MP: 181–186° C. ; API MS: 428 (M+1).

EXAMPLE 86

(1H-Indol-5-yl)-[6-(6-methoxy-pyridin-3-yl)-thieno[3,2-d]pyrimidin-4-yl]-amine

In a sealed tube (2-bromo-thieno[3,2-b]pyrimidin-7-yl)-(1H-indol-5-yl)-amine (150 mg, 0.29 mmol) and 3-pyridyl-diethyborane (133 mg, 0.869 mmol) were combined in 3 mL of dimethylformamide along with copper iodide (3 mg, 0.015 mmol). Nitrogen was bubbled through the solution and trans-benzyl(chloro)bis-triphenylphosphine)palladium (II) (33 mg, 0.044 mmol) was added, the tube was sealed and heated to 90° C. After 14 hours the solution was cooled and concentrated to dryness. Chromatography on 15 g of silica gel with CH₂Cl₂/MeOH (5–20%) afforded 71 mg (44%) of the title compound. LC-MS: 374(MH⁺); MP:243–249° C.; HPLC RT: 5.396 minutes.

EXAMPLE 87

N-(4-Methoxy-phenyl)-N'-[2-(6-methoxy-pyridin-3-yl)-thieno[3,2-b]pyridin-7-yl]-benzene-1,4-diamine The title compound was prepared from 2-methoxy-pyridyl-5-boronic acid and N-(6-bromo-thieno[3,2-d]pyrimidin-4-yl)-N'-(4-methoxy-phenyl)-benzene-1,4-diamine by a procedure analogous to example 2. M.P. 175–184° C.; LC-MS: 455.29 (MH⁺); HPLC RT: 6.646 minutes.

EXAMPLE 88

(6-Chloro-1H-indol-5-yl)-(6-phenyl-thieno[3,2-d]pyrimidin-4-yl)-amine

The title compound was prepared according to a procedure that is analogous to the procedures described in the above examples.

EXAMPLE 89

A. Preparation of 4-[7-(2-methyl-1H-Indol-5-ylamino)-thieno[3,2-b]pyridin-2-yl]-benzaldehyde The title compound was prepared from 4-formylbenzeneboronic acid and (2-bromo-thieno[3,2-b]pyridin-7-yl)-(2-methyl-1H-indol-5-yl)-amine by a procedure analogous to example 17. RP18-HPLC RT: 5.391 minutes; API MS: 384.29 (M⁺1).

A. Preparation of 4-[7-(2-methyl-1H-Indol-5-ylamino)-thieno[3,2-b]pyridin-2-yl]-benzaldehyde In a sealed tube 2-bromo-7-chloro-thieno[3,2-b]pyrimidine (735 mg, 2.96 mmol) was dissolved in 15 mL of dichloroethane and 15 mL of t-butylalcohol. 2-Methyl-5-aminoindole (480 mg, 3.26 mmol) was added, the tube was sealed, and the contents were heated at 85° C. for 36 hours. The solution was cooled and filtered, the solid washed with methanol, and dried in vacuo to afford 1.96 mg (quanitative yield) of the title compound which was used without further purification. RP18-HPLC RT: 5.827 minutes; API MS: 359.08 (M+1).

C. 2-{4-[7-(2-Methyl-1H-indol-5-ylamino)-thieno[3,2-b]pyridin-2-yl]-benzylamino}ethanol The title compound was prepared from 4-[7-(2-methyl-1H-Indol-5-ylamino)-thieno[3,2-b]pyridin-2-yl]-benzaldehyde (60 mg, 0.156 mmol) and 2-hydroxyethylamine (57 mg, 0.939 mmol) by a procedure analogous to example 82. RP18-HPLC RT: 4.078 minutes; API MS: 465.0 (M$^+$1).

EXAMPLE 90

(2-Methyl-1H-indol-5-yl)-[2-(4-morpholin-4-ylmethyl-phenyl)-thieno[3,2-b]pyridin-7-yl]amine The title compound was prepared from 4-[7-(2-methyl-1H-Indol-5-ylamino)-thieno[3,2-b]pyridin-2-yl]-benzaldehyde(60 mg, 0.156 mmol) and morpholine (82 mg, 0.939 mmol) by a procedure analogous to example 89. RP18-HPLC RT: 4.652 minutes; API MS: 454.59 (M+1).

EXAMPLE 91

(1H-Indol-5-yl)-(6-phenyl-thieno[3,2-d]pyrimidin-4-yl)-amine

In a 125 mL single neck round bottom flask with reflux condenser, 4-hydroxy-(6-phenyl)-thieno[3,2-d]pyrimidine was combined with thiphenylphosphine polymers (900 mg, 2.7 mmole), carbon tetrachloride (1.1 mL, 11 mmole) and dichloroethane (15 mL). Boiling chips were added and the mixture was refluxed for 18 hours. The mixture was cooled to ambient temperature and filtered into a second single neck round bottom flask. The polymer was washed with 25 mL 10% dichloroethane/tert-butanol. The organic layers were combined and 5-amino-indole (212 mg, 1.6 mmole) was added and the resulting solution was refluxed for 18 hours. The reaction mixture was cooled to ambient temperature and concentrated to a green-brownish residue. The residue was partitioned between 1 N NaOH and 15% 2-propanol/chloroform. The aqueous layer is extracted 2 times with 15 mL 15% isopropanol/CHCl$_3$. The organic layers were combined and dried over sodium sulfate and concentrated to a black residue. The residue was triturated with methanol to give 57 mg of product: MP: 255–258° C. (dec); anal. RP18-HPLC RT: 4.38 minutes; TS-MS: 343 (M+1).

EXAMPLE 92

(6-Phenyl-thieno[3,2-d]pyrimidin-4-yl)-m-tolyl-amine

Following the procedure of Example 91, the title product was prepared in 61% yield from 4-hydroxy-6-phenyl-thieno[3,2-d]pyrimidine (1.0 eg) and m-toluidine (1.5 eg) in butanol. The HCl salt was prepared from the purified free base by dissolving the free base in minimal methanol and a solution of Hcl in (Hcl(g) bubbled into 2 ml Et$_2$O) was added dropwise until the mixture remained cloudy. The precipitated Hcl salt was dried in vacuo, washed once with Et$_2$O, and dried in vacuo to constant mass: MP: 238–241° C.; TS-MS: 318 (MH$^+$); anal. RP18-HPLC RT: 4.96 minutes.

EXAMPLES 93–97

Examples 93–97 were prepared according to the method of Example 91 from 4-hydroxy-6-phenyl-thieno[3,2-d]pyrimidine and appropriate amine starting materials.

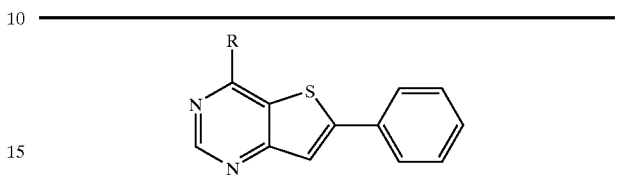

| Example no. | R | Yield (%) | LC/MS (M+) |
|---|---|---|---|
| 93 | 6-chloro-2,3-dihydro-indol-1-yl | 78 | 364 |
| 94 | 1,2,3,5-tetrahydro-pyrrolo[2,3-f]indol-1-yl |  | 369 |
| 95 | 3-methyl-4-hydroxy-phenylamino | 92 | 334 |
| 96 | benzo[b]thiophen-5-ylamino | 87 | 360 |
| 97 | 6-bromo-7-methyl-2,3-dihydro-indol-1-yl | 14 | 423 |

EXAMPLES 98–105

The compounds of Examples 98–105 were prepared according to the method of example 91 from 4-hydroxy-6-(4-methoxy-phenyl)-thieno[3,2-d]pyrimidine and appropriate amine starting material.

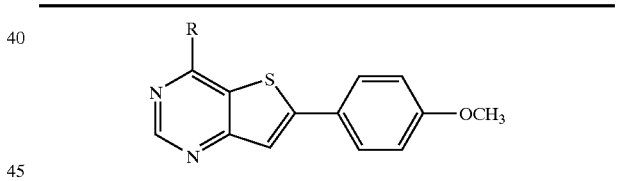

| Example no. | R | Yield (%) | LC/MS (M+) |
|---|---|---|---|
| 98 | 3-methyl-phenylamino | 93 | 347 |
| 99 | 3-bromo-phenylamino | 96 | 412 |
| 100 | 1H-indazol-5-ylamino | 84 | 373 |
| 101 | 1H-indol-5-ylamino | 76 | 372 |
| 102 | 3-chloro-4-fluoro-phenylamino | 96 | 385 |
| 103 | 3-methyl-4-hydroxy-phenylamino | 94 | 363 |
| 104 | 6-bromo-7-methyl-2,3-dihydro-indol-1-ylamino | 93 | 452 |
| 105 | 3-ethynyl-phenylamino |  | 357 |

Examples 106–113

The compounds of Examples 106–113 were prepared according to the method of Example 91 from 4-hydroxy-5-(2,4-dimethoxy-phenyl)-thieno[2,3-d]pyrimidine and appropriate amine starting materials.

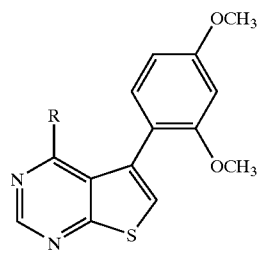

| Example no. | R | Yield (%) | LC/MS (M+) |
|---|---|---|---|
| 106 | 3-methyl-phenylamino | 51 | 377 |
| 107 | 3-bromo-phenylamino | 29 | 442 |
| 108 | 1H-indazol-5-ylamino | 27 | 403 |
| 109 | 1H-indol-5-ylamino | 40 | 402 |
| 110 | 3-chloro-4-fluoro-phenylamino | 40 | 415 |
| 111 | 3-methyl-4-hydroxy-phenylamino | | 393 |
| 112 | benzo[b]thiophen-5-ylamino | 32 | 419 |
| 113 | 3-ethynyl-phenylamino | 49 | 387 |

EXAMPLE 114

N,N-Dimethyl-N'-{4-[7-(2-methyl-1H-indol-5-ylamino)-thieno[3,2-b]pyridin-2-yl]-benzyl}-propane-1,3-diamine The title compound was prepared from 4-[7-(2-methyl-1H-Indol-5-ylamino)-thieno[3,2-b]-benzaldehyde (63 mg, 0.166 mmol) and 3-(dimethylamine)-propylamine (102 mg, 0.994 mmol) by a procedure analogous to example 89. RP18-HPLC RT: 4.35 min.; API MS: 69.66 (M1) MP: 167° C. (soften, 275° C. 9 dec.).

EXAMPLES 115–146

Compounds from example 115–146 synthesized is a method analogous to Example 61 starting with 4-Chloro-6-phenyl-thieno[3,2-d]pyrimidine (1.49 mL, 66.9 mM solution in DCE:tBuOH) and 110 mmol of the corresponding amines.

| Example No. | Compound Name | Mass Spec | HPLC (% purity) | HPLC retention times |
|---|---|---|---|---|
| 115 | (4-Methoxy-2-methyl-phenyl)-(6-phenyl-thieno[3,2-d]pyrimidin-4-yl)-amine | 347.2 | 80 | 5.747 |
| 116 | ([4-(4-Chloro-phenoxy)-phenyl]-(6-phenyl-thieno[3,2-d]pyrimidin-4-yl)-amine | 429.68 | 90 | 6.653 |
| 117 | 6-(6-Phenyl-thieno[3,2-d]pyrimidin-4-ylamino)-1H-benzo[d][1,3]oxazine-2,4-dione | 388.408 | unknown | 5.355 |
| 118 | 2-Diethylaminomethyl-4-(6-phenyl-thieno[3,2-d]pyrimidin-4-ylamino)-phenol | 404.538 | 95 | 5.007 |
| 119 | 5-Methyl-1-[4-(6-phenyl-thieno[3,2-d]pyrimidin-4-ylamino)-phenyl]-1,2-dihydro-pyrazol-3-one | 399.478 | 90 | 5.362 |
| 120 | [4-(4,5-Dichloro-imidazol-1-yl)-phenyl]-(6-phenyl-thieno[3,2-d]pyrimidin-4-yl)-amine | 438.341 | 90 | 5.920 |
| 121 | (6-Phenyl-thieno[3,2-d]pyrimidin-4-yl)-[4-(3-trifluoromethyl-pyrazol-1-yl)-phenyl]-amine | 437.449 | 90 | 6.130 |
| 122 | [4-(4-Methyl-piperazin-1-yl)-phenyl]-(6-phenyl-thieno[3,2-d]pyrimidin-4-yl)-amine | 401.537 | 30 | 4.940 |
| 123 | [4-(4-Methyl-piperidin-1-yl)-phenyl]-(6-phenyl-thieno[3,2-d]pyrimidin-4-yl)-amine | 400.55 | 70 | 5.210 |
| 124 | 1-[4-(6-Phenyl-thieno[3,2-d]pyrimidin-4-ylamino)-phenyl]-1H-tetrazole-5-thiol | 403.49 | unknown | 5.477 |
| 125 | 3-(6-Phenyl-thieno[3,2-d]pyrimidin-4-ylamino)-benzenesulfonamide | 382.466 | 40 | 5.160 |
| 126 | (2-Methyl-benzothiazol-6-yl)-(6-phenyl-thieno[3,2-d]pyrimidin-4-yl)-amine | 374.489 | 75 | 5.603 |
| 127 | [4-(Morpholine-4-sulfonyl)-phenyl]-(6-phenyl-thieno[3,2-d]pyrimidin-4-yl)-amine | 452.558 | 50 | 5.625 |
| 128 | [3,5-Dimethyl-4-(thiophen-3-ylmethoxy)-phenyl]-(6-phenyl-thieno[3,2-d]pyrimidin-4-yl)-amine | 443.594 | 95 | 6.515 |
| 129 | (6-Phenyl-thieno[3,2-d]pyrimidin-4-yl)-(2-pyrrol-1-yl-phenyl)-amine | 368.464 | 10 | 5.920 |
| 130 | [4,5-Dimethoxy-2-(1H-tetrazol-5-yl)-phenyl]-(6-phenyl-thieno[3,2-d]pyrimidin-4-yl)-amine | 431.479 | 70 | 5.428 |
| 131 | 5-[4-(6-Phenyl-thieno[3,2-d]pyrimidin-4-ylamino)-phenyl]-oxazolidine-2,4-dione | 402.435 | 90 | 5.270 |
| 132 | 1-Ethyl-5-(6-phenyl-thieno[3,2-d]pyrimidin-4-ylamino)-1,3-dihydro-indol-2-one | 386.479 | 90 | 5.343 |
| 133 | 6-(6-Phenyl-thieno[3,2-d]pyrimidin-4-ylamino)-3H-benzooxazol-2-one | 360.397 | 90 | 5.150 |
| 134 | Dibenzothiophen-4-yl-(6-phenyl-thieno[3,2-d]pyrimidin-4-yl)-amine | 409.535 | 80 | 6.318 |
| 135 | N-(6-Phenyl-thieno[3,2-d]pyrimidin-4-yl)-N'-p-tolyl-benzene-1,2-diamine | 408.529 | unknown | 5.305 |
| 136 | (2-Furan-2-yl-1-methyl-1H-benzoimidazol-5-yl)-(6-phenyl-thieno[3,2-d]pyrimidin-4-yl)-amine | 423.5 | 65 | 5.085 |

-continued

| Example No. | Compound Name | Mass Spec | HPLC (% purity) | HPLC retention times |
|---|---|---|---|---|
| 137 | 5-(6-Phenyl-thieno[3,2-d]pyrimidin-4-ylamino)-benzo[b]thiophene-2-carbonitrile | 384.485 | 90 | 5.935 |
| 138 | (6-Phenyl-thieno[3,2-d]pyrimidin-4-yl)-(2-pyridin-4-yl-1H-benzoimidazol-5-yl)-amine | 420.499 | 80 | 4.857 |
| 139 | [4-(1-Methyl-1H-imidazol-2-ylsulfanyl)-phenyl]-(6-phenyl-thieno[3,2-d]pyrimidin-4-yl)-amine | 415.542 | 60 | 4.993 |
| 140 | (6-Phenyl-thieno[3,2-d]pyrimidin-4-yl)-[4-(pyridin-2-yloxy)-phenyl]-amine | 396.474 | 90 | 5.715 |
| 141 | [4-(5-Methyl-tetrazol-1-yl)-phenyl]-(6-phenyl-thieno[3,2-d]pyrimidin-4-yl)-amine | 385.453 | 90 | 5.392 |
| 142 | 1-[3-(6-phenyl-thieno[3,2-d]pyrimidin-4-ylamino)-phenyl]-1H-tetrazole-5-thiol | 403.49 | unknown | 5.670 |
| 143 | N-(4-Chloro-phenyl)-N'-(6-phenyl-thieno[3,2-d]pyrimidin-4-yl)-benzene-1,4-diamine | 465.397 | 90 | 6.733 |
| 144 | 4-[4-(6-Phenyl-thieno[3,2-d]pyrimidin-4-ylamino)-phenylamino]-phenol | 410.501 | 72 | 5.643 |
| 145 | 6-(6-Phenyl-thieno[3,2-d]pyrimidin-4-ylamino)-benzothiazole-2-thiol | 392.27 | 85 | 5.720 |
| 146 | Benzo[1,2,3]thiadiazol-6-yl-(6-phenyl-thieno[3,2-d]pyrimidin-4-yl)-amine | 361.45 | 75 | 6.048 |

EXAMPLE 147

6-Iodo-4-chloro-thieno[3,2-d]pyridine

In a 500 mL round-bottomed flask 120 mL of tetrahydrofuran and with 13 grams of 4-chloro-thieno[3,2-d]pyridine (76.6 mmol) were cooled to −78° C. To the stirring solution was added n-butyllithium (191.6 mmol, 2.5M in hexane) was added dropwise over a 20 minute period. After stirring an additional 20 minutes iodine (48.3 g, 191.6 mmol) in 80 mL of THF was added dropwise such that the internal temperature did not exceed −78° C. After the addition was complete the reaction was allowed to slowly warm to room temperature. The reaction mixture was quenched by diluting with chloroform and extracting with $H_2O$ (2×250 mL), followed by extraction of the combined aqueous material with $CHCl_3$ (1×100 mL). The organic portions were then washed with $Na_2S_2O_3$ (2×200 mL), $H_2O$ (2×200 mL), dried over $MgSO_4$, filtered and dried. The resulting residue was suspended in a minimal amount of chloroform and an excess of ether was added. The solid obtained was filtered and washed with ether. The mother liquor was concentrated and another crop of material was isolated in the same fashion. The two crops of crystals were combined to afford 11.8 g (52%) of 6-iodo-4-chloro-thieno[3,2-d]pyridine that was greater than 90% pure. $^1H$ NMR (400 MHz, $CDCl_3$) δ8.51 (d, 1H), 7.83 (s, 1H), 7.24 (d, 1H). LC-MS: 295.9, 297.9 ($MH^+$); HPLC RT: 6.45 min.

EXAMPLE 148

A. 2-[2-(tert-Butyl-dimethyl-silanyl)-3-methyl-3H-imidazol-4-yl]-7-chloro-thieno[3,2-b]pyridine 2-(tert-Butyl-dimethyl-silanyl)-1-methyl-1H-imidazole (1.3 g, 6.74 mmol) was dissolved in 15 mL of tetrahydrofuran and cooled to −78° C. and n-butyllithiuim (2.8 mL, 2.5M in hexane) was added dropwise. The cooling bath was removed and the mixture was stirred at room temperature for 3 hours. The solution was recooled to −78° C. and zinc chloride (14.9 mL, 0.5M in THF) was added and the reaction mixture was warmed to room temperature. After 1 hour, 6-iodo-4-chloro-thieno[3,2-d]pyridine (1.0 g, 3.37 mmol) in 7 mL of THF was added followed by tetrakis (390 mg, 0.337 mmol), and the solution was heated to reflux for 3 hours. The mixture was cooled to room temperature, diluted with water, and extracted with chloroform (3×50 mL). The organic extracts were dried over $Na_2SO_4$, filtered, and concentrated. Chromatography on 50 g of silica gel with 2% methanol-:methylene chloride afforded 912 mg (74%) of 2-[2-(tert-Butyl-dimethyl-silanyl)-3-methyl-3H-imidazol-4-yl]-7-chloro-thieno[3,2-b]pyridine. $^1H$ NMR (400 MHz, $CD_3OD$) δ8.58 (d, 1H), 7.69 (s, 1H), 7.51 (s, 1H), 7.47 (d, 1H), 3.97 (s, 3H), 0.98 (s, 9H), 0.47 (s, 6H). LC-MS: 364, 366 ($MH^+$); HPLC RT: 6.65 min.

B. 7-Chloro-2-(3-methyl-3H-imidazol-4-yl)-thieno[3,2-b]pyridine

2-[2-(tert-Butyl-dimethyl-silanyl)-3-methyl-3H-imidazol-4-yl]-7-chloro-thieno[3,2-b]pyridine (912 mg, 2.50 mmol) was dissolved in 15 mL of methanol and 10 mL of 1N aqueous hydrochloric acid and heated to 35° C. overnight. The solution was cooled, diluted with water, and extracted with ethyl acetate (3×30 mL). The aqueous layer was made basic (pH 9) with 1N aqueous sodium hydroxide and extracted with chloroform (3×30 mL). The combined extracts were dried over $Na_2SO_4$, filtered, and concentrated to afford 528 mg (84%) of 7-chloro-2-(3-methyl-3H-imidazol-4-yl)-thieno[3,2-b]pyridine. $^1H$ NMR (400 MHz, $CD_3OD$) δ8.58 (d, 1H), 7.84 (s, 1H), 7.68 (s, 1H), 7.47 (d, 1H), 7.42 (s, 1H), 3.93 (s, 3H). LC-MS: 250.1, 252 ($MH^+$); HPLC RT: 4.40 min.

C. [2-(3-Methyl-3H-imidazol-4-yl)-thieno[3,2-b]pyridin-7-yl]-(2-methyl-1H-indol-5-yl)-amine 7-Chloro-2-(3-methyl-3H-imidazol-4-yl)-thieno[3,2-b]pyridine (600 mg, 2.40 mmol) and 2-methyl-5-aminoindole (422 mg, 2.89 mmol) were dissolved in 20 mL of tert-butanol and 20 mL of dichloroethane and heated to 85° C. The solvent was allowed to evaporate overnight and was replaced the following day with the same amounts as in the initial reaction mixture along with an additional 90 mg of the indole. The solution was heated an additional 24 hours and allowed to go dry as before. Chromatography of the residue with 30–5-% methanol:ethyl acetate afforded 142 mg (16%) of [2-(3-methyl-3H-imidazol-4-yl)-thieno[3,2-b]pyridin-7- yl]-(2-methyl-1H-indol-5-yl)-amine. $^1$H NMR (400 MHz, CD$_3$OD) δ8.14 (d, 1H), 7.79 (s, 1H), 7.75 (s, 1H), 7.40 (s, 1H), 7.34 (d, 1H), 7.29 (s, 1H), 6.99 (d, 1H), 6.72 (d, 1H), 6.17 (s, 1H), 3.84 (s, 3H), 2.44 (s, 3H). LC-MS: 360, 361 (MH$^+$); HPLC RT: 3.96 min.

EXAMPLE 149

A. 2-[5-(7-Chloro-thieno[3,2-b]pyridin-2-yl)-1-methyl-1H-imidazol-2-yl]-propan-2-ol In a 50 mL round-bottomed flask 7 mL of tetrahydrofuran and n-butyllithium (0.88 mL, 2.5M in hexane) were cooled to −40° C. A suspension of 7-chloro-2-(3-methyl-3H-imidazol-4-yl)-thieno[3,2-b]pyridine (500 mg, 2.00 mmol) in 9 mL of tetrahydrofuran was added dropwise to the solution and stirred for 40 minutes. Acetone (0.79 mL, 3.00 mmol) was added to the anion and the reaction mixture was allowed to warm to room temperature overnight. The mixture was diluted with water and extracted with chloroform (3×50 mL). The combined extracts were dried over NaSO$_4$, filtered, and concentrated. Chromatography on 50 g of silica gel with 5% methanol:methylene chloride afforded 191 mg (31%) of 2-[5-(7-chloro-thieno[3,2-b]pyridin-2-yl)-1-methyl-1H-imidazol-2-yl]-propan-2-ol. $^1$H NMR (400 MHz, CDCl$_3$) δ8.58 (d, 1H), 7.51 (s, 1H), 7.28 (d, 1H), 7.24 (s, 1H), 4.02 (s, 3H), 1.77 (s, 6H). LC-MS: 308.1, 310.1 (MH$^+$); HPLC RT: 4.18 min.

B. 2-{1-Methyl-5-[7-(2-methyl-1H-indol-5-ylamino)-thieno[3,2-b]pyridin-2-yl]-1H-imidazol-2-yl}-propan-2-ol 2-[5-(7-Chloro-thieno[3,2-b]pyridin-2-yl)-1-methyl-1H-imidazol-2-yl]-propan-2-ol (190 mg, 0.62 mmol) and 2-methyl-5-aminoindole (108 mg, 0.714 mmol) were dissolved in 3 mL of t-butyl alcohol and 3 mL of dichloroethane and the solution was heated to 85° C. After allowing the reaction to go dry overnight solvent was added along with an additional 45 mg of the indole an the solution was heated an additional 18 hours. Chromatography of the residue with 20% methanol:methylene chloride afforded 166 mg (66%) of 2-{1-methyl-5-[7-(2-methyl-1H-indol-5-ylamino)-thieno[3,2-b]pyridin-2-yl]-1H-imidazol-2-yl}-propan-2-ol. $^1$H NMR (400 MHz, CD$_3$OD) δ8.17 (d, 1H), 7.51 (s, 1H), 7.44 (s, 1H), 7.40 (d, 1H), 7.02 (d, 1H), 6.84 (s, 1H), 6.20 (s, 1H), 3.33 (s, 3H), 2.44 (s, 3H), 1.64 (s, 6H). LC-MS: 418, 419 (MH$^+$); HPLC RT: 3.98 min.

EXAMPLE 150

A. 7-Chloro-2-(1-methyl-1H-imidazol-2-yl)-thieno[3,2-b]pyridine

1-Methylimidazole (0.54 mL, 6.74 mmol) was dissolved in 15 mL of tetrahydrofuran and cooled to −78° C. and n-butyllithiuim (2.8 mL, 2.5M in hexane) was added dropwise. After stirring 30 minutes at −78° C. zinc chloride (14.9 mL, 7.42 mmol) was added and the solution was allowed to warm to room temperature. After 1 hour, 6-iodo-4-chloro-thieno[3,2-d]pyridine (1.0 g, 3.37 mmol) in 7 mL of THF was added followed by tetrakis (390 mg, 0.337 mmol) and the solution was heated to reflux for 3 hours. The mixture was cooled to room temperature, diluted with water, and extracted with chloroform (3×50 mL). The organic extracts were dried over Na$_2$SO$_4$, filtered, and concentrated. Chromatography on 50 g of silica gel with 2% methanol:methylene chloride afforded 458 mg (55%) of 7-Chloro-2-(1-methyl-1H-imidazol-2-yl)-thieno[3,2-b]pyridine. $^1$H NMR (400 MHz, CD$_3$OD) δ8.58 (d, 1H), 7.69 (s, 1H), 7.51 (s, 1H), 7.47 (d, 1H), 3.97 (s, 3H), 0.98 (s, 9H), 0.47 (s, 6H). LC-MS: 364, 366 (MH$^+$); HPLC RT: 6.65 min.

B. [2-(1-Methyl-1H-imidazol-2-yl)-thieno[3,2-b]pyridin-7-yl]-(2-methyl-1H-indol-5-yl)-amine 7-Chloro-2-(1-methyl-1H-imidazol-2-yl)-thieno[3,2-b]pyridine (1.0 g, 4.0 mmol) and 2-methyl-5-aminoindole (732 mg, 5.0 mmol) were dissolved in 7 mL of t-butyl alcohol and 7 mL of dichloroethane and the solution was heated to 85° C. After allowing the reaction to go dry overnight the reaction mixture was cooled and absorbed onto silica gel. Chromatography of the residue with 20% methanol:methylene chloride afforded 991 mg (69%) of [2-(1-methyl-1H-imidazol-2-yl)-thieno[3,2-b]pyridin-7-yl]-(2-methyl-1H-indol-5-yl)-amine. $^1$H NMR (400 MHz, CD$_3$OD) δ8.26 (d, 1H), 7.95 (s, 1H), 7.62 (s, 1H), 7.48 (m, 2H), 7.39 (d, 1H), 7.04 (m, 2H), 6.20 (s, 1H), 3.33 (s, 3H), 2.43 (s, 3H). LC-MS: 360 (MH$^+$); HPLC RT: 4.15 min.

EXAMPLE 151

A. 7-Chloro-2-thiazol-2-yl-thieno[3,2-b]pyridine

6-Bromo-4-chloro-thieno[3,2-d]pyridine (3.72 g, 15 mmol) and 2-tributylstannanyl-thiazole (14 g, 37.4 mmol) were combined with copper (I) iodide (285 mg, 1.5 mmol), trans-benzyl(chloro)bis(tripehnylphosphine)palladium(II) (3.4 g, 4.5 mmol) in 22 mL of dimethylformamide. The reaction mixture was heated to 90° C. and stirred 1 hour. The mixture was cooled, concentrated, and absorbed onto silica gel. Chromatography with 10% ethyl acetate:methylene chloride afforded 1.6 g (42%) of 7-chloro-2-thiazol-2-yl-thieno[3,2-b]pyridine. $^1$H NMR (400 MHz, CDCl$_3$) δ8.59 (d, 1H), 7.93 (s, 1H), 7.89 (d, 1H), 7.45 (d, 1H), 7.30 (d, 1H). LC-MS: 253 (MH$^+$); HPLC RT: 5.75 min.

B. (2-Methyl-1H-indol-5-yl)-(2-thiazol-2-yl-thieno[3,2-b]pyridin-7-yl)-amine 7-Chloro-2-thiazol-2-yl-thieno[3,2-b]pyridine (400 mg, 1.58 mmol) and 2-methyl-5-aminoindole (231 mg, 1.58 mmol) were dissolved in 6 mL of t-butyl alcohol and 6 mL of dichloroethane and the solution was heated to 85° C. After allowing the reaction to go dry overnight the reaction mixture was cooled and absorbed onto silica gel. Chromatography of the residue with 5% methanol:methylene chloride afforded 374 mg (68%) (2-methyl-1H-indol-5-yl)-(2-thiazol-2-yl-thieno[3,2-b]pyridin-7-yl)-amine. $^1$H NMR (400 MHz, DMSO) δ8.78 (s, 1H), 8.18 (d, 1H), 7.84 (m, 2H), 7.27 (m, 2H), 6.90 (d, 1H), 7.39 (d, 1H), 6.59 (d, 1H), 6.10 (s, 1H), 2.36 (s, 3H). LC-MS: 363 (MH$^+$); HPLC RT: 5.01 min.

EXAMPLE 152

A. 2-[2-(7-Chloro-thieno[3,2-b]pyridin-2-yl)-thiazol-5-yl]-propan-2-ol

In a 25 mL round-bottomed flask 2 mL of tetrahydrofuran and diisopropyl amine (0.14 mL, 1.0 mmol) were cooled to −78° C. and n-butyllithium (0.38 mL, 0.95 mmol) was added. The solution was warmed to 0° C. for 10 minutes then recooled to −78° C. A solution of 7-chloro-2-thiazol-2-yl-thieno[3,2-b]pyridine (200 mg, 0.79 mmol) in 2 mL of tetrahydrofuran was added dropwise and the resulting solution was stirred 30 minutes. Acetone (0.88 mL, 1.19 mmol) was added to the anion and the reaction mixture was allowed to warm to room temperature overnight. The mixture was diluted with water and extracted with chloroform (3×50 mL). The combined extracts were dried over NaSO$_4$, filtered, and concentrated. Chromatography on 50 g of silica gel with 30% ethyl acetate:methylene chloride afforded 129 mg (52%) 2-[2-(7-Chloro-thieno[3,2-b]pyridin-2-yl)-thiazol-5-yl]-propan-2-ol. $^1$H NMR (400 MHz, CD$_3$OD) δ8.56 (d, 1H), 7.95 (s, 1H), 7.71 (s, 1H), 7.50 (d, 1H), 1.66 (s, 6H). LC-MS: 308.1, 311 (MH$^+$); HPLC RT: 5.32 min.

B. 2-{2-[7-(2-Methyl-1H-indol-5-ylamino)-thieno[3,2-b]pyridin-2-yl]-thiazol-5-yl}-propan-2-ol 2-[2-(7-Chloro-thieno[3,2-b]pyridin-2-yl)-thiazol-5-yl]-propan-2-ol (129 mg, 0.42 mmol), 2-methyl-5-aminoindole (72 mg, 0.50 mmol), potassium carbonate (138 mg. 8.84 mmol), and triethylamine (0.12 mL, 0.84 mmol) were dissolved in 2 mL of t-butyl alcohol and 2 mL of dichloroethane and the solution was heated to 85° C. After allowing the reaction to go dry overnight solvent was added along with an additional 36 mg of the indole an the solution was heated an additional 18 hours. Chromatography of the residue with 20% methanol:methylene chloride afforded 166 mg (40%) of 2-{2-[7-(2-methyl-1H-indol-5-ylamino)-thieno[3,2-b]pyridin-2-yl]-thiazol-5-yl}-propan-2-ol. $^1$H NMR (400 MHz, CD$_3$OD) δ8.13 (d, 1H), 7.71 (s, 1H), 7.62 (s, 1H), 7.35 (d, 1H), 7.30 (d, 1H), 6.99 (d, 1H), 6.64 (d, 1H), 6.13 (s, 1H), 2.43 (s, 3H), 1.65 (s, 6H). LC-MS: 421 (MH$^+$); HPLC RT: 4.75 min.

EXAMPLE 153

[6-(4-Fluoro-phenyl)-thieno[3,2-d]pyrimidin-4-yl]-(1H-indol-5-yl)-amine

The title compound was prepared from 4-pyridylboronic acid and (6-bromo-thieno[3,2-d]pyrimidin-4-yl)-(1H-indol-5-yl)-amine by the procedure analogous to Example 2 above. M.P. 208–213° C.; LC-MS: 343 (MH$^+$); HPLC RT: 4.967 minutes.

EXAMPLE 154

4-[7-(2-Methyl-1H-indol-5-ylamino)-thieno[3,2-b]pyridin-2-yl]-benzaldehyde

The title compound was prepared from 4-pyridylboronic acid and (2-bromo-thieno[3,2-b]pyridin-7-yl)-(2-methyl-1H-indol-5-yl)-amine by the procedure analogous to Example 17 above. RP18-HPLC RT: 4.36 minutes; API MS: 357 (M+1); M.P.: 223–240° C.

EXAMPLE 155

(2-Furan-3-yl-thieno[3,2-b]pyridin-7-yl)-(2-methyl-1H-indol-5-yl)-amine

The title compound was prepared from 3-furanboronic acid and (2-bromo-thieno[3,2-b]pyridin-7-yl)-(2-methyl-1H-indol-5-yl)-amine by the procedure analogous to Example 2 above. $^1$H NMR (400 MHz, CD$_3$OD) δ8.02 (d, 1H), 7.91 (s, 1H), 7.53 (m, 1H), 7.35 (s, 1H), 7.31 (d, 1H), 7.27 (d, 1H), 6.94 (dd, 1H), 6.77 (m, 1H), 6.54 (d, 1H), 6.10 (s, 1H), 2.40 (s, 3H), RP18-HPLC RT: 5.39 minutes; API MS: 346 (M+1).

EXAMPLE 156

[2-(2-Ethoxy-thiazol-5-yl)-thieno[3,2-b]pyridin-7-yl]-(2-methyl-1H-indol-5-yl)-amine The title compound was prepared from 2-methyl-5-aminoindole and 7-chloro-2-(2-ethoxy-thiazol-5-yl)-thieno[3,2-b]pyridine by the procedure analogous to example 148(c) above. $^1$H NMR (400 MHz, CD$_3$OD) δ10.95 (s, 1H), 8.62 (s, 1H), 8.23 (d, 1H), 7.52 (s, 1H), 7.45 (s, 1H), 7.33 (m, 2H), 6.88 (d, 1H), 6.52 (d, 1H), 6.08 (s, 1H), 4.44 (q, 2H), 2.46 (s, 3H), 1.35 (t, 3H); RP18-HPLC RT: 5.83 minutes; API MS: 407 (M+1).

EXAMPLE 157

(2-Methyl-1H-indol-5-yl)-[2-(4-methyl-thiazol-2-yl)-thieno[3,2-b]pyridin-7-yl]-amine The title compound was prepared from 2-methyl-5-aminoindole and 7-chloro-2-(4-methyl-thiazol-2-yl)-thieno[3,2-b]pyridine by the procedure analogous to example 148(c) above. $^1$H NMR (400 MHz, CD$_3$OD) δ8.11 (d, 1H), 7.73 (s, 1H), 7.34 (s, 1H), 7.25 (d, 1H), 7.20 (s, 1H), 6.97 (d, 1H), 6.62 (d, 1H), 6.12 (s, 1H), 2.43 (s, 3H), 2.42 (s, 3H), RP18-HPLC RT: 5.41 minutes; API MS: 377 (M+1).

EXAMPLE 158

[2-3-Metoxymethyl-3H-imidazol-4-yl)-thieno[3,2-b]pyridin-7-yl]-(2-methyl-1H-indol-5-y)-amine The title compound was prepared from 2-methyl-5-aminoindole and 7-chloro-2-(3-methoxymethyl-3H-imidazol-4-y)-thieno[3,2-b]pyridine by the procedure analogous to example 148(c) above. $^1$H NMR (400 MHz, CD$_3$OD) δ8.03 (d, 1H), 7.91 (s, 1H), 7.54 (s, 1H), 7.25 (m, 2H), 6.90 (d, 1H), 6.53 (d, 1H), 6.06 (s, 1H), 4.89 (s, 2H), 3.28 (s, 3H), 2.37 (s, 3H); RP18-HPLC RT: 4.17 minutes; API MS: 390 (M+1).

EXAMPLE 159

(2-Benzooxazol-2-yl-thieno[3,2-b]pyridin-7-yl)-(2-methyl-1H-indol-5-yl)-amine

The title compound was prepared from 2-methyl-5-aminoindole and 2-(7-chloro-thieno[3,2-b]pyridin-2-yl)-benzooxazole by the procedure analogous to example 148(c) above. $^1$H NMR (400 MHz, CD$_3$OD) δ8.18 (d, 1H), 8.10 (s, 1H), 7.70 (m, 2H), 7.40 (m, 4H), 6.98 (d, 1H), 6.68 (d, 1H), 6.14 (s, 1H), 2.43 (s, 3H); RP18-HPLC RT: 6.13 minutes; API MS 397 (M+1).

EXAMPLE 160

(2-Methyl-1H-indol-5yl)-[2-(4-Methyl-thiophen-2-yl)-thieno[3,2-b]pyridin-7-yl-]-amine The title compound was prepared from 4-methyl-2-thiopheneboronic acid and (2-bromothieno[3,2-b]pyridin-7-yl)-(2-methyl-1H-indol-5-yl)-amine by the procedure analogous to example 2 above. $^1$H NMR (400 MHz, CD$_3$OD) δ8.00 (d, 1H), 7.25 (m, 3H), 7.10 (s, 1H), 6.95 (s, 1H), 6.94 (dd, 1H), 6.52 (d, 1H), 6.08 (s, 1H), 2.39 (s, 3H), 2.18 (s, 3H); RP18-HPLC RT: 6.41 minutes; API MS: 376 (M+1).

EXAMPLE 161

(2-Benzo[1,3]dioxol-5-yl-thieno[3,2-b]pyridin-7-yl)-(2-methyl-1H-indol-5-yl)-amine The title compound was prepared from 1,3-benzodioxole-5-boronic acid and (2-bromothieno[3,2-b]pyridin-7-yl)-(2-methyl-1H-indol-5-yl)-amine by the procedure analogous to example 2 above. $^1$H NMR (400 MHz, CD$_3$OD) δ8.00 (d, 1H), 7.38 (s, 1H), 7.26 (m, 2H), 7.13 (m, 2H), 6.93 (d, 1H), 6.77 (d, 1H), 6.52 (d, 1H), 6.08 (s, 1h), 5.92 (s, 2H), 2.39 (s, 3H); RP18-HPLC RT: 6.09 minutes; API MS: 400 (M+1).

EXAMPLE 162

(2-Methyl-1H-indol-5-yl)-(2-thiophen-2-yl-thieno[3,2-b]pyridin-7-yl)-amine

The title compound was prepared from 2-thiopheneboronic acid and (2-bromothieno[3,2-b]pyridin-7-yl)-(2-methyl-1H-indol-5-yl)-amine by the procedure analogous to example 2 above. $^1$H NMR (400 MHz, CD$_3$OD) δ8.01 (d, 1H), 7.39 (d, 1H), 7.36 (s, 1H), 7.30 (s, 1H), 7.26 (d, 1H), 7.01 (dd, 1H), 6.94 (dd, 1H), 6.53 (d, 1H), 6.09 (s, 1H), 2.39 (s, 3H); RP18-HPLC RT: 5.78 minutes; API MS: 362 (M+1).

EXAMPLE 163

2-[7-(2-Methyl-1H-indol-5-ylamino)-thieno[3,2-b]pyridin-2-yl]-pyrrole-1-carboxylic Acid tert-butyl Ester The title compound was prepared from N-tert-butoxycarbonylpyrrole-2-boronic acid and (2-bromothieno[3,2-b]pyridin-7-yl)-(2-methyl-1H-indol-5-yl)-amine by the procedure analogous to example 2 above. $^1$H NMR (400 MHz, CD$_3$OD) δ8.08 (d, 1H), 7.36 (m, 2H), 7.28, s, 1H), 7.27 (d, 1H), 6.94 (dd, 1H), 6.60 (d, 1H), 6.40 (m, 1H), 6.22 (dd, 1H), 6.10 (s, 1H), 2.40 (s, 3H), 1.90 (s, 9H); RP18-HPLC RT: 6.73 minutes; API MS: 445 (M+1).

EXAMPLE 164

(2-Methyl-1H-indol-5-yl)-[2-(5-methyl-thiophen-2-yl)-thieno[3,2-b]pyridin-7-yl]-amine The title compound was prepared from 5-methylthiophene-2-boronic acid and (2-bromothieno[3,2-b]pyridin-7-yl)-(2-methyl-1H-indol-5-yl)-amine by the procedure analogous to example 2 above. $^1$H NMR (400 MHz, CD$_3$OD) δ8.03 (d, 1H), 7.29 (m, 3H), 7.15 (s, 1H), 6.99 (m, 1H), 6.83 (d, 1H), 6.54 (d, 1H), 6.10 (s, 1H), 2.41 (s, 3H), 2.22 (s, 3H); RP18-HPLC RT: 6.08 minutes; API MS: 376 (M+1).

EXAMPLE 165

{2-[5-(4-Methoxy-phenyl)-oxazol-2-yl]-thieno[3,2-b]pyridin-7-yl}-(2-methyl-1H-indol-5-yl)-amine The title compound was prepared from 2-methyl-5-aminoindole and 7-chloro-2-[5-(4-methoxy-phenyl)-oxazol-2-yl]-thieno[3,2-b]pyridine by the procedure analogous to example 148(c) above. $^1$H NMR (400 MHz, CD$_3$OD) δ11.00 (s, 1H), 8.79 (s, 1H), 8.21 (d, 1H), 7.98 (s, 1H), 7.79 (m, 2H), 7.76 (s, 1H), 7.24 (m, 2H), 7.08 (s, 1H), 7.06 (s, 1H), 6.85 (d, 1H), 6.60 (d, 1H), 6.10 (s, 1H), 3.79 (s, 3H), 2.42 (s, 3H); RP18-HPLC RT: 6.55 minutes; API MS: 453 (M+1).

EXAMPLE 166

(2-Methyl-1H-indol-5-yl)-[2-(6-methyl-pyridin-2-yl)-thieno[3,2-b]pyridin-7-yl]-amine The title compound was prepared from 2-methyl-5-aminoindole and 7-chloro-2-(6-methyl-pyridin-2-yl)-thieno[3,2-b]pyridine by the procedure analogous to example 148(c) above. $^1$H NMR (400 MHz, CD$_3$OD) δ8.51 (d, 1H), 7.83 (s, 1H), 7.68 (m, 2H), 7.34 (m, 1H), 7.27 (d, 1H), 7.16 (d, 1H), 6.97 (dd, 1H), 6.57 (d, 1H), 6.10 (s, 1H), 2.52 (s, 3H), 2.40 (s, 3H); RP18-HPLC RT: 5.70 minutes; API MS: 371 (M+1).

EXAMPLE 167

{2-[2-(2,5-Dimethyl-pyrrol-1-yl)-pyrimidin-5-yl]-thieno[3,2-b]pyridin-7-yl}-(2-methyl-1H-indol-5-yl)-amine The title compound was prepared from 2-methyl-5-aminoindole and 7-chloro-2-[2-(2,5-dimethyl-pyrrol-1-yl)-pyrimidin-5-yl]-thieno[3,2-b]pyridine by the procedure analogous to example 148(c) above. $^1$H NMR (400 MHz, CD$_3$OD) δ9.18 (s, 2H), 8.17 (d, 1h), 7.80 (s, 1H), 7.37 (s, 1H), 7.34 (d, 1H), 6.98 (d, 1H), 6.62 (d, 1H), 6.17 (s, 1H), 5.83 (s, 1H), 2.47 (s, 3H), 2.33 (s, 6H); RP18-HPLC RT: 6.81 minutes; API MS: 451 (M+1).

EXAMPLE 168

(2-Methyl-1H-indol-5-yl)-[2-(1H-pyrrol-2-yl)-thieno[3,2-b]pyridin-7-yl]-amine A mixture of 2-[7-(2-methyl-1H-indol-5-ylamino)-thieno[3,2-b]pyridin-2-yl]-pyrrole-1-carboxylic acid tert-butyl ester (131 mg, 0.29 mmol) and trifluoroacetic acid (0.1 mL) in dichloromethane (1 mL) was stirred overnight. The solution was diluted with dichloromethane and water, and the pH was adjusted to 8.0 with a saturated aqueous sodium carbonate solution. The organic layer was dried over Na$_2$SO$_4$ and concentrated to afford (2-methyl-1H-indol-5-yl)-[2-(1H-pyrrol-2-yl)-thieno[3,2-b]pyridin-7-yl]-amine (62 mg, 56%). $^1$H NMR (400 MHz, CD$_3$OD) δ7.93 (d, 1H), 7.25 (m, 3H), 6.93 (dd, 1H), 6.83 (s, 1H, 6.44 (dd, 1H), 6.13 (dd, 1H), 6.07 (s, 1H), 2.37 (s, 3H); RP18-HPLC RT: 5.45 minutes; API MS: 345 (M+1).

EXAMPLE 169

{2-[6-(2,5-Dimethyl-pyrrol-1-yl)-2-methyl-pyridin-3-yl]-thieno[3,2-b]pyridin-7-yl}-(2-methyl-1H-indol-5-yl)-amine The title compound was prepared from 2-methyl-5-aminoindole and 7-chloro-2-[6-(2,5-dimethyl-pyrrol-1-yl)-2-methyl-pyridin-3-yl]-thieno[3,2-b]pyridine by the procedure analogous to example 148(c) above. $^1$H NMR (400 MHz, CD$_3$OD) δ8.08 (s, 1H), 7.82 (d, 1H), 7.40 (s, 1H), 7.30 (s, 1H), 7.25 (d, 1H), 7.07 (d, 1H), 6.92 (dd, 1H), 6.58 (d, 1H), 6.07 (s, 1H), 5.80 (s, 2H), 2.60 (s, 3H), 2.36 (s, 3H), 2.05 (s, 6H); RP18-HPLC RT: 6.55 minutes; API MS: 464 (M+1).

EXAMPLE 170

{2-[6-(2,5-Dimethyl-pyrrol-1-yl)-5-methyl-pyridin-3-yl]-thieno[3,2-b]pyridin-7-yl}-(2-methyl-1H-indol-5-yl)-amine The title compound was prepared from 2-methyl-5-aminoindole and 7-chloro-2-[6-(2,5-dimethyl-pyrrol-1-yl)-5-methyl-pyridin-3-yl]-thieno[3,2-b]pyridine by the procedure analogous to example 148(c) above. $^1$H NMR (400 MHz, CD$_3$OD) δ8.71 (s, 1H), 8.17 (s, 1H), 8.08 (d, 1H), 7.77 (s, 1H), 7.30 (m, 2H), 6.95 (d, 1H), 6.58 (d, 1H), 6.11 (s, 1H), 5.84 (s, 2H), 2.40 (s, 3H), 1.99 (s, 3H), 1.91 (s, 6H); RP18-HPLC RT: 6.67 minutes.

EXAMPLE 171

2-{4-Methyl-2-[7-(2-methyl-1H-indol-5-ylamino)-thieno[3,2-b]pyridin-2-yl]-thiazol-5-yl}-propan-2-ol The title compound was prepared from 2-methyl-5-aminoindole and 2-[2-(7-chloro-thieno[3,2-b]pyridin-2-yl)-

4-methyl-thiazol-5-yl]-propan-2-ol by the procedure analogous to example 148(c) above. $^1$H NMR (400 MHz, CD$_3$OD) δ8.07 (t, 1H), 7.62 (d, 1H), 7.27 (m, 2H), 6.95 (m, 1H), 6.58 (t, 1H), 6.10 (d, 1H), 5.46 (d, 1H), 2.46 (s, 3H), 2.40 (s, 3H), 1.60 (s, 6H); RP18-HPLC RT: 5.17 minutes; API MS: 435 (M+1).

EXAMPLE 172

(2-Methyl-1H-indol-5-yl)-(2-phenyl-thieno[3,2-b]pyridin-7-yl)-amine

The title compound was prepared from phenyl boronic acid and (2-bromothieno[3,2-b]pyridin-7-yl)-(2-methyl-1H-indol-5-yl)-amine by the procedure analogous to example 2 above. $^1$H NMR (400 MHz, CD$_3$OD) δ8.02 (d, 1H), 7.67 (d, 2H), 7.54 (s, 1H), 7.30 (m, 5H), 6.94 (d, 1H), 6.54 (d, 1H), 6.09 (s, 1H), 2.39 (s, 3H); RP18-HPLC RT: 6.21 minutes; API MS 356 (M+1).

EXAMPLE 173

[2-(3-Methyl-3H-imidazol-4-yl)-thieno[3,2-b]pyridin-7-yl]-phenyl-amine

The title compound was prepared from 7-Chloro-2-(3-methyl-3H-imidazol-4-yl)-thieno[3,2-b]pyridine and aniline by the procedure analogous to example 148(c) above. $^1$H NMR (400 MHz, CD$_3$OD) δ8.18 (d, 1H), 7.77 (s, 1H), 7.39 (s, 1H), 7.37 (m, 3H), 7.28 (m, 2H), 7.18 (t, 1H), 6.80 (d, 1H), 3.86 (s, 3H); RP18-HPLC RT: 3.93 minutes; API MS: 307 (M+1).

EXAMPLE 174

6-[7-(2-Methyl-1H-indol-5-ylamino)-thieno[3,2-b]pyridin-2-yl]-pyridine-2-carboxylic Acid Methyl Ester The title compound was prepared from 6-(7-chloro-thieno[3,2-b]pyridin-2-yl)-pyridine-2-carboxylic acid methyl ester and 2-methyl-5-aminoindole by the procedure analogous to example 148(c) above. $^1$H NMR (400 MHz, CD$_3$OD) δ8.43 (d, 1H), 8.22 (s, 1H), 8.18 (d, 1H), 8.11 (t, 1H), 8.02 (d, 1H), 7.26 (m, 2H), 6.92 (d, 1H), 6.59 (d, 1H), 6.10 (s, 1H), 3.89 (s, 3H), 2.36 (s, 3H); RP18-HPLC RT: 5.34 minutes; API MS: 415 (M+1).

EXAMPLE 175

2-{6-[7-(2-Methyl-1H-indol-5-ylamino)-thieno[3,2-b]pyridin-2-yl]pyridin-2-yl}-propan-2-ol The title compound was prepared from 2-[6-(7-chloro-thieno[3,2-b]pyridin-2-yl)-pyridin-2-yl]-propan-2-ol and 2-methyl-5-aminoindole by the procedure analogous to example 148(c) above. $^1$H NMR (400 MHz, CD$_3$OD) δ8.05 (d, 1H), 7.83 (s, 1H), 7.75 (m, 2H), 7.53 (d, 1H), 7.33 (s, 1H), 7.27 (d, 1H), 6.95 (d, 1H), 6.56 (d, 1H), 6.10 (s, 1H), 2.40 (s, 3H), 1.54 (s, 6H); RP18-HPLC RT: 5.05 minutes; API MS: 415 (M+1).

EXAMPLE 176

{6-[7-(2-Methyl-1H-indol-5-ylamino)-thieno[3,2-b]pyridin-2-yl]-pyridin-2-yl}-methanol)

The title compound was prepared from [6-(7-chloro-thieno[3,2-b]pyridin-2-yl)-pyridin-2-yl]-methanol and 2-methyl-5-aminoindole by the procedure analogous to example 148(c) above. $^1$H NMR (400 MHz, CD$_3$OD) δ8.10 (d, 1H), 7.90 (s, 1H), 7.83 (m, 2H), 7.44 (m, 1H), 7.36 (s, 1H), 7.30 (d, 1H), 6.90 (d, 1H), 6.60 (d, 1H), 6.12 (s, 1H), 3.57 (s, 2H), 2.42 (s, 3H); RP18-HPLC RT: 4.59 minutes; API MS: 387 (M+1).

EXAMPLE 177

{6-[7-(2-Methyl-1H-indol-5-ylamino)-thieno[3,2-b]pyridin-2-yl]-pyridin-2-yl}-(4-methyl-piperazin-1-yl)-methanone The title compound was prepared from [6-(7-chloro-thieno[3,2-b]pyridin-2-yl)-pyridin-2-yl]-(4-methyl-piperazin-1-yl)-methanone and 2-methyl-5-aminoindole by the procedure analogous to example 148(c) above. $^1$H NMR (400 MHz, CD$_3$OD) δ8.06 (d, 1H), 7.90 (m, 3H), 7.58 (d, 1H), 7.30 (m, 2H), 6.93 (d, 1H), 6.62 (d, 1H), 6.10 (s, 1H), 3.77 (m, 2H), 3.59 (m, 2H), 2.55 (m, 2H), 2.40 (m, 2H), 2.40 (s, 3H), 2.31 (s, 3H); RP18-HPLC RT: 3.92 minutes; API MS: 483 (M+1).

EXAMPLE 178

{6-[7-(2-Methyl-1H-indol-5-ylamino)-thieno[3,2-b]pyridin-2-yl]-pyridin-2-yl}-morpholin-4-yl-methanone The title compound was prepared from [6-(7-chloro-thieno[3,2-b]pyridin-2-yl)-pyridin-2-yl]-morpholin-4-yl-methanone and 2-methyl-5-aminoindole by the procedure analogous to example 148(c) above. $^1$H NMR (400 MHz, CD$_3$OD) δ8.10 (d, 1H), 7.98 (d, 1H), 7.89 (t, 1H), 7.83 (s, 1H), 7.56 (d, 1H), 7.33 (s, 1H), 7.29 (d, 1H), 6.96 (d, 1H), 6.61 (d, 1H), 6.11 (s, 1H), 3.74 (s, 4H), 3.49 (s, 4H), 2.42 (s, 3H); RP18-HPLC RT: 4.58 minutes; API MS: 470 (M+1).

EXAMPLE 179

[2-(1-Methoxymethyl-1H-imidazol-2-yl)-thieno[3,2-b]pyridin-7-yl]-(2-methyl-1H-indol-5-yl)-amine The title compound was prepared from 7-chloro-2-(1-methoxymethyl-1H-imidazol-2-yl)-thieno[3,2-b]pyridine and 2-methyl-5-aminoindole by the procedure analogous to example 148(c) above. $^1$H NMR (400 MHz, CD$_3$OD) δ8.15 (d, 1H), 7.85 (s, 1H), 7.53 (s, 1H), 7.37 (m, 2H), 7.11 (s, 1H), 7.02 (d, 1H), 6.81 (d, 1H), 6.19 (s, 1H), 5.46 (s, 2H), 3.38 (s, 1H), 2.44 (s, 1H); RP18-HPLC RT: 4.38 minutes; API MS: 390 (M+1).

EXAMPLE 180

(2-Methyl-1H-indol-5-yl)-[2-(2-methyl-1-oxy-pyridin-4-yl)-thieno[3,2-b]pyridin-7-yl]-amine The title compound was prepared from 7-chloro-2-(2-methyl-1-oxy-pyridin-4-yl)-thieno[3,2-b]pyridine and 2-methyl-5-aminoindole by the procedure analogous to example 148(c) above. $^1$H NMR (400 MHz, CD$_3$OD) δ8.06 (d, 1H), 7.97 (d, 1H), 7.55 (s, 1H), 7.51 (s, 1H), 7.32 (m, 1H), 7.22 (m, 2H), 6.85 (d, 1H), 6.51 (d, 1H), 6.03 (s, 1H), 2.36 (s, 3H), 2.35 (s, 3H); RP18-HPLC RT: 3.79 minutes; API MS: 387 (M+1).

EXAMPLE 181

(2-Methyl-1H-indol-5-yl)-[2-(1-oxy-pyridin-4-yl)-thieno[3,2-b]pyridin-7-yl]-amine The title compound was prepared from 7-chloro-2-(1-oxy-pyridin-4-yl)-thieno[3,2-b]pyridine and 2-methyl-5- aminoindole by the procedure analogous to example 148(c) above. $^1$H NMR (400 MHz, CD$_3$OD) δ8.24 (m, 2H), 8.10 (s, 1H), 7.74 (m, 3H), 7.28 (m, 2H), 6.94 (d, 1H), 6.62 (d, 1H), 6.10 (s, 1H), 2.40 (s, 3H); API MS: 373 (M+1).

EXAMPLE 182

(2-Methyl-1H-indol-5-yl)-[2-(2-methyl-pyridin-4-yl)-thieno[3,2-b]pyridin-7-yl]-amine Phosphorous trichloride (0.10 mL of a 2M solution in dichloromethane, 0.20 mmol) was added to a solution of (2-methyl-1H-indol-5-yl)-[2-(2-methyl-1-oxy-pyridin-4-yl)-thieno[3,2-b]pyridin-7-yl]-amine in 2 mL dichloromethane. The resulting mixture was heated at reflux for 1 hour. Methanol was added and the reaction mixture was concentrated onto silica gel. Purification by flash chromatography eluting with methanol/chloroform (1/9, v/v) afforded (2-methyl-1H-indol-5-yl)-[2-(2-methyl-pyridin-4-yl)-thieno[3,2-b]pyridin-7-yl]-amine (15 mg, 20%). $^1$H NMR (400 MHz, CD$_3$OD) δ8.43 (d, 1H), 8.13 (d, 1H), 7.85 (s, 1H), 7.64 (s, 1H), 7.55 (d, 1H), 7.34 (m, 2H), 6.98 (d, 1H), 6.63 (d, 1H), 6.12 (s, 1H), 2.57 (s, 3H), 2.42 (s, 3H); RP18-HPLC RT: 4.80 minutes; API MS: 371 (M+1).

What is claimed is:

1. A compound of the formula 1 or 2

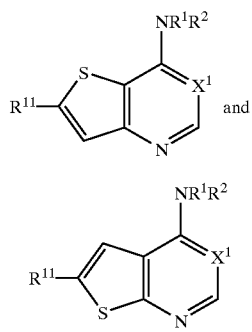

or a pharmaceutically acceptable salt or hydrate thereof, wherein:

wherein X' is CH;

R' is H, $C_1$-$C_6$ alkyl or —C(O)($C_1$-$C_6$ alkyl);

$R^2$ is $C_6$-$C_{10}$ aryl or 5–13 membered heterocyclic, wherein said $R^2$ groups are optionally substituted by 1 to 5 $R^5$ substituents, each $R^5$ is independently selected from halo, cyano, nitro, trifluoromethoxy, trifluoromethyl, azido, —C(O)$R^8$, —C(O)O$R^8$, —OC(O)$R^8$, —OC(O)O$R^8$, —NR$^6$C(O)R$^7$, —C(O)NR$^6$R$^7$, —NR$^6$R$^7$, —SO$_2$NR$^6$R$^7$, $C_1$-$C_6$ alkyl, —(CH$_2$)$_j$O(CH$_2$)$_q$NR$^6$R$^7$, —(CH$_2$)$_t$O(CH$_2$)$_q$OR$^9$, —(CH$_2$)$_t$OR$^9$, —S(O)$_j$($C_1$-$C_6$ alkyl), —(CH$_2$)$_t$($C_6$-$C_{10}$ aryl), —(CH$_2$)$_t$(5–10 membered heterocyclic), —(CH$_2$)$_t$O(CH$_2$)$_j$($C_6$-$C_{10}$ aryl), —(CH$_2$)$_t$O(CH$_2$)$_q$(5-10 membered heterocyclic), —C(O)(CH$_2$)$_t$(5–10 membered heterocyclic), —(CH$_2$)$_j$NR$^7$(CH$_2$)$_q$NR$^6$R$^7$, —(CH$_2$)$_j$NR$^7$CH$_2$C(O)NR$^6$R$^7$, (CH$_2$)$_j$NR$^7$(CH$_2$)$_q$NR$^9$C(O)R$^8$, —(CH$_2$)$_j$NR$^7$(CH$_2$)$_q$O(CH$_2$)$_q$OR$^9$, —(CH$_2$)$_j$NR$^7$(CH$_2$)$_q$S(O)$_j$($C_1$-$C_6$alkyl), —(CH$_2$)$_j$NR$^7$(CH$_2$)$_q$R$^6$, —SO$_2$(CH$_2$)$_t$($C_6$-$C_{10}$ aryl), and —SO$_2$(CH$_2$)$_t$ (5–10 membered heterocyclic), wherein j is an integer ranging from 0 to 2, t is an integer ranging from 0 to 6, q is an integer ranging from 2 to 6, the —(CH$_2$)$_q$— and —(CH$_2$)$_t$— moieties of the foregoing $R^5$ groups optionally include a carbon-carbon double or triple bond where t is an integer between 2 and 6, and the alkyl, aryl and heterocyclic moieties of the foregoing $R^5$ groups are optionally substituted by 1 to 3 substituents independently selected from halo, cyano, nitro, trifluoromethyl, azido, —C(O)$R^8$, —C(O)O$R^8$, —OC(O)$R^8$, —OC(O)O$R^8$, —NR$^6$C(O)R$^7$, —C(O)NR$^6$R$^7$, —(CH$_2$)$_t$NR$^6$R$^7$, $C_1$-$C_6$ alkyl, —(CH$_2$)$_t$$C_6$-$C_{10}$ aryl), —(CH$_2$)$_t$(5–10 membered heterocyclic), —(CH$_2$)$_t$O(CH$_2$)$_q$OR$^9$, and —(CH$_2$)$_t$OR$^9$, wherein t is an integer ranging from 0 to 6 and q is an integer ranging from 2 to 6;

each $R^6$ and $R^7$ is independently selected from H, $C_1$-$C_6$ alkyl, —(CH$_2$)$_t$($C_6$-$C_{10}$ aryl), —(CH$_2$)$_t$(5–10 membered heterocyclic), —(CH$_2$)$_t$O(CH$_2$)$_q$OR$^9$, and —(CH$_2$)$_t$OR$^9$, wherein t is an integer ranging from 0 to 6 and q is an integer ranging from 2 to 6, and the alkyl, aryl and heterocyclic moieties of the foregoing $R^6$ and $R^7$ groups are optionally substituted by 1 to 3 substituents independently selected from halo, cyano, nitro, trifluoromethyl, azido, —C(O)$R^8$, —C(O)O$R^8$, —OC(O)$R^8$, —NR$^9$C(O)R$^{10}$, —C(O)NR$^9$R$^{10}$, —NR$^9$R$^{10}$, $C_1$-$C_6$ alkyl, —(CH$_2$)$_t$($C_6$-$C_{10}$ aryl), —(CH$_2$)$_t$(5–10 membered heterocyclic), —(CH$_2$)$_t$O(CH$_2$)$_q$OR$^9$, and —(CH$_2$)$_t$OR$^9$, wherein t is an integer ranging from 0 to 6 and q is an integer ranging from 2 to 6, with the proviso that where $R^6$ and $R^7$ are both attached to the same nitrogen, then $R^6$ and $R^7$ are not both bonded to the nitrogen directly through an oxygen;

each $R^8$ is independently selected from H, $C_1$-$C_{10}$ alkyl, —(CH$_2$)$_t$($C_6$-$C_{10}$ aryl), and —(CH$_2$)$_t$(5–10 membered heterocyclic), wherein t is an integer ranging from 0 to 6;

each $R^9$ and $R^{10}$ is independently selected from H and $C_1$-$C_6$ alkyl; and, $R^{11}$ is H, $C_1$-$C_6$ alkyl, —C(O)NR$^6$R$^9$, —C(O)($C_6$-$C_{10}$ aryl), —(CH$_2$)$_t$($C_6$-$C_{10}$ aryl), or —(CH$_2$)$_t$(5–10 membered heterocyclic), wherein t is an integer ranging from 0 to 6, wherein said $R_{11}$ groups, other than H, are optionally substituted by 1 to 5 $R^5$ groups.

2. A compound of claim 1 wherein said compound is a compound of formula 1 wherein $R^{11}$ is —(CH$_2$)$_t$($C_6$-$C_{10}$ aryl) or —(CH$_2$)$_t$(5–10 membered heterocyclic), wherein t is an integer ranging from 0 to 6, wherein said $R^{11}$ groups are optionally substituted by 1 to 5 $R^5$ groups.

3. A compound of claim 2 wherein $R^{11}$ is phenyl or pyridyl, wherein said phenyl and pyridyl are optionally substituted by 1 to 5 $R^5$ groups.

4. A compound of claim 1 wherein said compound is a compound of formula 1 wherein $R^2$ is phenyl optionally substituted by 1 to 5 $R^5$ substituents.

5. A compound of claim 1 wherein said compound is a compound of formula 1 wherein $R^2$ is a group of the formula

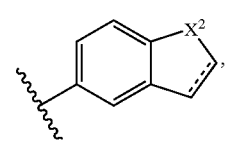

-continued

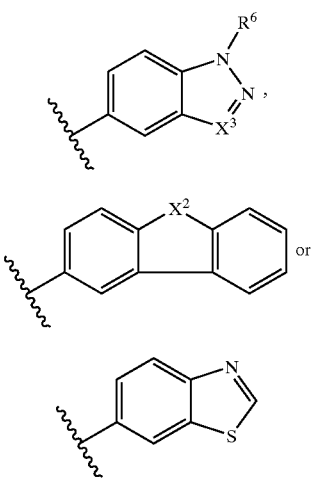

wherein X² is —S— or —N(R⁶)—, X³ is N or CH, the dashed line in formula 3 represents an optional double bond, and the above R² groups of formulas 3 and 5 are optionally substituted by 1 to 5 R⁵ substituents and the R² groups of formulas 4 and 6 are optionally substituted by 1 to 3 R⁵ substituents.

6. A compound of claim 5 wherein R² is a group of formula 3 above wherein said group is optionally substituted by 1 to 5 R⁵ substituents.

7. A compound according to claim 1 selected from the group consisting of

[2-(4-Fluoro-phenyl)-thieno[3,2-b]pyridin-7-yl]-(1H-indol-5-yl)-amine;
(1H-Indol-5-yl)-(2-thiophen-2-yl-thieno[3,2-b]pyridin-7-yl)-amine;
4-[7-(1H-Indol-5-ylamino)-thieno[3,2-b]pyridin-2-yl]-benzaldehyde;
(1H-Indol-5-yl)-[2-(4-methylsulfanyl-phenyl)-thieno[3,2-b]pyridin-7-yl]-amine;
(1H-Indol-5-yl)-thieno[3,2-b]pyridin-7-yl-amine;
2-{4-[7-(1H-Indol-5-ylamino)-thieno[3,2-b]pyridin-2-yl]-phenoxy}-ethanol;
[2-(4-Dimethylamino-phenyl)-thieno[3,2-b]pyridin-7-yl]-(1H-indol-5-yl)-amine;
4-[7-(1H-Indol-5-ylamino)-thieno[3,2-b]pyridin-2-yl]-benzoic acid methyl ester;
(1H-Indol-5-yl)-(2-thiophen-3-yl-thieno[3,2-b]pyridin-7-yl)-amine;
(1H-Indol-5-yl)-(2-{4-[(2-methoxy-ethylamino)-methyl]-phenyl}-thieno[3,2-b]pyridin-7-yl)-amine;
Furan-2-yl-(4-{4-[7-(1H-indol-5-ylamino)-thieno[3,2-b]pyridin-2-yl]-benzyl}-piperazin-1-yl)-methanone;
4-[7-(1H-Indol-5-ylamino)-thieno[3,2-b]pyridin-2-yl]-phenol;
2-(2-{4-[7-(1H-Indol-5-ylamino)-thieno[3,2-b]pyridin-2-yl]-benzylamino}-ethoxy-ethanol;
2-{4-[7-(1H-Indol-5-ylamino)-thieno[3,2-b]pyridin-2-yl]-benzylamino}-ethanol;
N-{4-[7-(1H-Indol-5-ylamino)-thieno[3,2-b]pyridin-2-yl]-benzyl}-N',N'-dimethyl-hexane-1,6-diamine;
2-({4-[7-(1H-Indol-5-ylamino)-thieno[3,2-b]pyridin-2-yl]-benzyl}-methyl-amino)-ethanol;
(1H-Indol-5-yl)-(2-{4-[(2-piperazin-1-yl-ethylamino)-methyl]-phenyl}-thieno[3,2-b]pyridin-7-yl)-amine;
(2-{4-[(3-Imidazol-1-yl-propylamino)-methyl]-phenyl}-thieno[3,2-b]pyridin-7-yl)-(1H-indol-5-yl)-amine;
2-((2-Hydroxy-ethyl)-{4-[7-(1H-indol-5-ylamino)-thieno[3,2-b]pyridin-2-yl]-benzyl}-amino)-ethanol;
[2-(4-Dimethylaminomethyl-phenyl)-thieno[3,2-b]pyridin-7-yl]-(1H-indol-5-yl)-amine;
N-{4-[7-(1H-Indol-5-ylamino)-thieno[3,2-b]pyridin-2-yl]-benzyl}-N',N'-dimethyl-ethane-1,2-diamine;
(1-{4-[7-(1H-Indol-5-ylamino)-thieno[3,2-b]pyridin-2-yl]-benzyl}-pyrrolidin-2-yl-methanol;
2-(4-{4-[7-(1H-Indol-5-ylamino)-thieno[3,2-b]pyridin-2-yl]-benzyl}-piperazin-1-yl)-ethanol;
(1H-Indol-5-yl)-{2-[4-(2-morpholin-4-yl-ethoxy)-phenyl]-thieno[3,2-b]pyridin-7-yl}-amine;
1-{4-[7-(1H-Indol-5-ylamino)-thieno[3,2-b]pyridin-2-yl]-benzyl}-piperidine-4-carboxylic acid amide;
{4-[7-(1H-Indol-5-ylamino)-thieno[3,2-b]pyridin-2-yl]-phenyl}-methanol;
2-{4-[7-(1H-Indol-5-ylamino)-thieno[3,2-b]pyridin-2-yl]-benzylamino}-butan-1-ol;
N-{4-[7-(1H-Indol-5-ylamino)-thieno[3,2-b]pyridin-2-yl]-benzyl}-N'-methyl-ethane-1,2-diamine;
(1H-Indol-5-yl)-[2-(4-Morpholin-4-ylmethyl-phenyl)-thieno[3,2-b]pyridin-7-yl]-amine;
3-{4-[7-(1H-Indol-5-ylamino)-thieno[3,2-b]pyridin-2-yl]-benzylamino}-propan-1-ol;
1-(3-{4-[7-(1H-Indol-5-ylamino)-thieno[3,2-b]pyridin-2-yl]-benzylamino}-propyl)-pyrrolidin-2-one;
(1H-Indol-5-yl)-{2-[4-(2-methoxy-ethoxy)-phenyl]-thieno[3,2-b]pyridin-7-yl}-amine;
2-(2-{4-[7-(1H-Indol-5-ylamino)-thieno[3,2-b]pyridin-2-yl]-benzylamino}-ethylamino)-ethanol;
3-{4-[7-(1H-Indol-5-ylamino)-thieno[3,2-b]pyridin-2-yl]-benzylamino}-2,2-dimethyl-propan-ol;
3-{4-[7-(1H-Indol-5-ylamino)-thieno[3,2-b]pyridin-2-yl]-benzylamino}-propane-1,2-diol;
[2-(4-{[2-(1H-Imidazol-4-yl)-ethylamino]-methyl}-phenyl)-thieno[3,2-b]pyridin-7-yl]-1H-indol-5-yl)-amine;
N-(2-{4-[7-(1H-Indol-5-ylamino)-thieno[3,2-b]pyridin-2-yl]-benzylamino}-ethyl)-acetamide;
2-{4-[7-(1H-Indol-5-ylamino)-thieno[3,2-b]pyridin-2-yl]-benzylamino}-acetamide;
2-{4-[7-(1H-Indol-5-ylamino)-thieno[3,2-b]pyridin-2-yl]-benzylamino}-propane-1,3-diol;
N-(4-Methoxy-phenyl)-N'-[2-(3-nitro-phenyl)-thieno[3,2-b]pyridin-7-yl]-benzene-1,4-diamine;
(7-Methoxy-1H-indol-5-yl)-(2-phenyl-thieno[3,2-b]pyridin-7-yl)-amine;
(1H-Indol-5-yl)-[2-(4-methylaminomethyl-phenyl)-thieno[3,2-b]pyridin-7-yl]-amine;
N-{4-[7-(1H-Indol-5-ylamino)-thieno[3,2-b]pyridin-2-yl]-benzyl}-ethane-1,2-diamine;
{4-[7-(1H-Indol-5-ylamino)-thieno[3,2-b]pyridin-2-yl]-benzylamino}-acetic acid methyl ester;
N-{4-[7-(1H-Indol-5-ylamino)-thieno[3,2-b]pyridin-2-yl]-benzyl}-N',N'-dimethyl-propane-1,3-diamine;
(1H-Indol-5-yl)-(2-pyridin-2-yl-thieno[3,2-b]pyridin-7-yl)-amine;
(1H-Indol-5-yl)-(2-{4-[(2-morpholin-4-yl-ethylamino)-methyl]-phenyl}-thieno[3,2-b]pyridin-7-yl)-amine;
(1H-Indol-5-yl)-{2-[4-(pyrrolidin-3-ylaminomethyl)-phenyl]-thieno[3,2-b]pyridin-7-yl}-amine;
1-(4-{4-[7-(1H-Indol-5-ylamino)-thieno[3,2-b]pyridin-2-yl]-benzyl}-piperazin-1-yl)-ethanone;
1-{4-[7-(1H-Indol-5-ylamino)-thieno[3,2-b]pyridin-2-yl]-benzyl}-pyrrolidine-2-carboxylic acid amide;
N-(4-Methoxy-phenyl )-N'-[2-(6-methoxy-pyridin-3-yl)-thieno[3,2-b]pyridin-7-yl]-benzene-1,4-diamine;

(1H-Indol-5-yl)-(2-pyridin-3-yl-thieno[3,2-b]pyridin-7-yl)-amine;

4-[7-(1H-Indol-5-ylamino)-thieno[3,2-b]pyridin-2-yl]-but-3-yn-1-ol;

N-(4-Methoxy-phenyl)-N'-(2-thiophen-2-yl-thieno[3,2-b]pyridin-7-yl)-benzene-1,4-diamine;

N-(2-Hydroxy-ethyl)4-[7-(1H-indol-5-ylamino)-thieno[3,2-b]pyridin-2-yl]-benzamide;

N-(3-Imidazol-1-yl-propyl)-4-[7-(1H-indol-5-ylamino)-thieno[3,2-b]pyridin-2-yl]-benzamide;

3-[4-(4-{4-[7-(1H-Indol-5-ylamino)-thieno[3,2-b]pyridin-2-yl]-benzylamino}-butyl)-piperazin-1-yl]-propan-1-ol;

(1H-Indol-5-yl)-[2-(4-{[4-(4-methyl-piperazin-1-yl)-butylamino]-methyl}-phenyl)-thieno[3,2-b]pyridin-7-yl]-amine;

2-[4-(4-{4-[7-(1H-Indol-5-ylamino)-thieno[3,2-b]pyridin-2-yl]-benzylamino}-butyl)-piperazin-1-yl]-ethanol;

1-Imidazol-1-yl-3-{4-[7-(1H-indol-5-ylamino)-thieno[3,2-b]pyridin-2-yl]-benzylamino}-propan-2-ol;

5-{4-[7-(1H-Indol-5-ylamino)-thieno[3,2-b]pyridin-2-yl]-benzylamino}-pentan-1-ol;

2-[2-(4-{4-[7-(1H-Indol-5-ylamino)-thieno[3,2-b]pyridin-2-yl]-benzyl}-piperazin-1yl)-ethoxy]-ethanol;

(1H-Indol-5-yl)-(2-{4-[(2-methylsulfanyl-ethylamino)-methyl]-phenyl}-thieno[3,2-b]pyridin-7-yl)-amine;

2-[(2-Hydroxy-ethyl)-(3-{4-[7-(1H-indol-5-ylamino)-thieno[3,2-b]pyridin-2-benzylamino}-propyl)-amino]-ethanol;

N-(2-Amino-ethyl)-N'-{4-[7-(1H-indol-5-ylamino)-thieno[3,2-b]pyridin-2-yl]-benzyl}-ethane-1,2-diamine;

2-(3-{4-[7-(1H-Indol-5-ylamino)-thieno[3,2-b]pyridin-2-yl]-benzylamino}-propylamino)-ethanol;

N-{4-[7-(1H-Indol-5-ylamino)-thieno[3,2-b]pyridin-2-yl]-benzyl}-hexane-1,6-diamine;

(2-Methyl-1H-indol-5-yl)-[2-(4-morpholin-4-ylmethyl-phenyl)-thieno[3,2-b]pyridin-7-yl-amine;

2-{4-[7-(2-Methyl-1H-indol-5-ylamino)-thieno[3,2-b]pyridin-2-yl]-benzylamino}-ethanol;

(1H-Indol-5-yl)-[2-(6-methoxy-pyridin-3-yl)-thieno[3,2-b]pyridin-7-yl]-amine;

{5-[7-(1H-Indol-5-ylamino)-thieno[3,2-b]pyridin-2-yl]-pyridin-2-yl}-methanol;

N,N-Dimethyl-N'-{4-[7-(2-methyl-1H-indol-5-ylamino)-thieno[3,2-b]pyridin-2-yl]-benzyl}-propane-1,3-diamine;

2-[(2-Hydroxy-ethyl)-(3-{4-[7-(2-methyl-1H-indol-5-ylamino)-thieno[3,2-b]pyridin-2-yl]-benzylamino}-propyl)-amino]-ethanol;

2-{4-[7-(2-Methyl-1H-indol-5-ylamino)-thieno[3,2-b]pyridin-2-yl]-benzylamino}-propane-1,3-diol;

3-{4-[7-(2-Methyl-1H-indol-5-ylamino)-thieno[3,2-b]pyridin-2-yl]-benzylamino}-propane-1,2-diol;

1-(3-{4-[7-(2-Methyl-1H-indol-5-ylamino)-thieno[3,2-b]pyridin-2-yl]-benzylamino}-propyl)-pyrrolidin-2-one;

N-(2-Amino-ethyl)-N'-{4-[7-(2-methyl-1H-indol-5-ylamino)-thieno[3,2-b]pyridin-2-yl]-benzyl}-ethane-1,2-diamine;

2-(2-{4-[7-(2-Methyl-1H-indol-5-ylamino)-thieno[3,2-b]pyridin-2-yl]-benzylamino}-ethylamino)-ethanol;

3-{4-[7-(2-Methyl-1H-indol-5-ylamino)-thieno[3,2-b]pyridin-2-yl]-benzylamino}-propan-1-ol;

1-{4-[7-(2-Methyl-1H-indol-5-ylamino)-thieno[3,2-b]pyridin-2-yl]-benzyl}-piperidine-4-carboxylic acid amide;

2-(2-{4-[7-(2-Methyl-1H-indol-5-ylamino)-thieno[3,2-b]pyridin-2-yl]-benzylamino}-ethoxy)-ethanol;

2-(Methyl-{4-[7-(2-methyl-1H-indol-5-ylamino)-thieno[3,2-b]pyridin-2-yl]-benzyl}-amino)-ethanol;

N-Methyl-N'-{4-[7-(2-methyl-1H-indol-5-ylamino)-thieno[3,2-b]pyridin-2-yl]-benzyl}-ethane-1,2-diamine;

(1H-Indol-5-yl)-[2-(3-nitro-phenyl)-thieno[3,2-b]pyridin-7-yl]-amine;

N-{4-[7-(2-Methyl-1H-indol-5-ylamino)-thieno[3,2-b]pyridin-2-yl]-benzyl}-ethane-1,2-diamine;

(2-Methyl-1H-indol-5-yl)-(2-{4-[(2-piperazin-1-yl-ethylamino)-methyl]-phenyl}-thieno[3,2-b]pyridin-7-yl)-amine;

N,N-Dimethyl-N'-{4-[7-(2-methyl-1H-indol-5-ylamino)-thieno[3,2-b]pyridin-2-yl]-benzyl}-ethane-1,2-diamine;

2-{4-[7-(2-Methyl-1H-indol-5-ylamino)-thieno[3,2-b]pyridin-2-yl]-benzylamino}-butan-1-ol;

(2-Methyl-1H-indol-5-yl)-(2-{4-[(2-morpholin-4-yl-ethylamino)-methyl]-phenyl}-thieno[3,2-b]pyridin-7-yl)-amine;

(2-Methyl-1H-indol-5-yl)-{2-[4-(pyrrolidin-3-ylaminomethyl)-phenyl]-thieno[3,2-b]pyridin-7-yl}-amine;

{6-[7-(1H-Indol-5-ylamino)-thieno[3,2-b]pyridin-2-yl]-pyridin-3-yl}-methanol;

{6-[7-(2-Methyl-1H-indol-5-ylamino)-thieno[3,2-b]pyridin-2-yl]-pyridin-3-yl}-methanol;

3-[4-(4-{4-[7-(2-Methyl-1H-indol-5-ylamino)-thieno[3,2-b]pyridin-2-yl]-benzylamino}-butyl)-piperazin-1-yl]-propan-1-ol;

2-[4-(4-{4-[7-(2-Methyl-1H-indol-5-ylamino)-thieno[3,2-b]pyridin-2-yl]-benzylamino}-butyl)-piperazin-1-yl]-ethanol;

(2-{4-[(3-Imidazol-1-yl-propylamino)-methyl]-phenyl}-thieno[3,2-b]pyridin-7-yl)-(2-methyl-1H-indol-5-yl)-amine;

1-Imidazol-1-yl-3-{4-[7-(2-methyl-1H-indol-5-ylamino)-thieno[3,2-b]pyridin-2-yl]-benzylamino}-propan-2-ol;

2-[(2-Hydroxy-ethyl)-(4-{4-[7-(2-methyl-1H-indol-5-ylamino)-thieno[3,2-b]pyridin-2-yl]-benzylamino}-butyl)-amino]-ethanol;

N,N-Diethyl-N'-{4-[7-(2-methyl-1H-indol-5-ylamino)-thieno[3,2-b]pyridin-2-yl]-benzyl}-propane-1,3-diamine;

[2-(3-Amino-phenyl)-thieno[3,2-b]pyridin-7-yl]-(1H-indol-5-yl)-amine;

(2-Methyl-1H-indol-5-yl)-(2-{4-[(3-morpholin-4-yl-propylamino)-methyl]-phenyl}-thieno[3,2-b]pyridin-7-yl)-amine;

[2-(4-Dimethylaminomethyl-phenyl)-thieno[3,2-b]pyridin-7-yl]-(2-methyl-1H-indol-5-yl)-amine;

1-[5-(2-Pyridin-2-yl-thieno[3,2-b]pyridin-7-ylamino)-2,3-dihydro-indol-1-yl]-ethanone;

(2,3-Dihydro-1H-indol-5-yl)-(2-pyridin-2-yl-thieno[3,2-b]pyridin-7-yl)-amine;

(1H-Benzotriazol-5-yl)-(2-pyridin-2-yl-thieno[3,2-b]pyridin-7-yl)-amine;

5-(2-Phenyl-thieno[3,2-b]pyridin-7-ylamino)-1H-indole-3-carbaldehyde;

(1H-Indazol-5-yl)-(2-pyridin-2-yl-thieno[3,2-b]pyridin-7-yl)-amine;

(2-Methyl-1H-indol-5-yl)-(2-pyridin-2-yl-thieno[3,2-b]pyridin-7-yl)-amine;

(1H-Benzoimidazol-5-yl)-(2-phenyl-thieno[3,2-b]pyridin-7-yl)-amine;

5-(2-Pyridin-2-yl-thieno[3,2-b]pyridin-7-ylamino)-1H-indole-2-carboxylic acid dimethylamide;

{5-[7-(2-Methyl-1H-indol-5-ylamino)-thieno[3,2-b]pyridin-2-yl]-pyridin-2-yl)-methanol;

N-(3-Imidazol-1-yl-propyl)-6-[7-(1H-indol-5-ylamino)-thieno[3,2-b]pyridin-2-yl]-nicotinamide;

N-(3-Hydroxy-propyl)-6-[7-(2-methyl-1H-indol-5-ylamino)-thieno[3,2-b]pyridin-2-yl]-nicotinamide;

[2-(5-Amino-pyridin-2-yl)-thieno[3,2-b]pyridin-7-yl]-(2-methyl-1H-indol-5-yl)-amine;
N-[2-(2-Hydroxy-ethoxy)-ethyl]-6-[7-(2-methyl-1H-indol-5-ylamino)-thieno[3,2-b]pyridin-2-yl]-nicotinamide;
[2-(3-Methyl-3H-imidazol-4-yl)-thieno[3,2-b]pyridin-7-yl]-(2-methyl-1H-indol-5-amine;
2-{1-Methyl-5-[7-(2-methyl-1H-indol-5-ylamino)-thieno[3,2-b]pyridin-2-yl]-1H-imidazol-2-yl}-propan-2-ol;
[2-(1-Methyl-1H-imidazol-2-yl)-thieno[3,2-b]pyridin-7-yl]-(2-methyl-1H-indol-5-amine;
(2-Methyl-1H-indol-5-yl)-(2-thiazol-2-yl-thieno[3,2-b]pyridin-7-yl)-amine;
2-{2-[7-(2-Methyl-1H-indol-5-ylamino)-thieno[3,2-b]pyridin-2-yl]-thiazol-5-yl}-propan-2-ol;
4-[7-(2-Methyl-1H-indol-5-ylamino)-thieno[3,2-b]pyridin-2-yl]-benzaldehyde;
and the pharmaceutically acceptable salts and hydrates thereof.

8. A compound according to claim 1 selected from the group consisting of (2-Furan-3-yl-thieno[3,2-b]pyridin-7-yl)-(2-methyl-1H-indol-5-yl)-amine;
[2-(2-Ethoxy-thiazol-5-yl)-thieno[3,2-b]pyridin-7-yl]-(2-methyl-1H-indol-5-yl)-amine;
(2-Methyl-1H-indol-5-yl )-[2-(4-methyl-thiazol-2-yl)-thieno[3,2-b]pyridin-7-yl]-amine;
[2-(3-Methoxymethyl-3H-imidazol-4-yl)-thieno[3,2-b]pyridin-7-yl]-(2-methyl-1H-indol-5-yl)-amine;
(2-Benzooxazol-2-yl-thieno[3,2-b]pyridin-7-yl)-(2-methyl-1H-indol-5-yl)-amine;
(2-Methyl-1H-indol-5-yl)-[2-(4-methyl-thiophen-2-yl)-thieno[3,2-b]pyridin-7-yl]-amine;
(2-Benzo[1,3]dioxol-5-yl-thieno[3,2-b]pyridin-7-yl)-(2-methyl-1H-indol-5-yl)-amine;
(2-Methyl-1H-indol-5-yl)-(2-thiophen-2-yl-thieno[3,2-b]pyridin-7-yl)-amine;
2-[7-(2-Methyl-1H-indol-5-ylamino)-thieno[3,2-b]pyridin-2-yl]-pyrrole-1-carboxylic acid tert-butyl ester;
(2-Methyl-1H-indol-5-yl)-[2-(5-methyl-thiophen-2-yl)-thieno[3,2-b]pyridin-7-yl]-amine;
{2-[5-(4-Methoxy-phenyl)-oxazol-2-yl]-thieno[3,2-b]pyridin-7-yl}-(2-methyl-1H-indol-5-yl)-amine;
(2-Methyl-1H-indol-5-yl )-[2-(6-methyl-pyridin-2-yl)-thieno[3,2-b]pyridin-7-yl]-amine;
{2-[2-(2,5-Dimethyl-pyrrol-1-yl)-pyrimidin-5-yl]-thieno[3,2-b]pyridin-7-yl}-(2-methyl-1H-indol-5-yl)-amine;
(2-Methyl-1H-indol-5-yl)-[2-(1H-pyrrol-2-yl)-thieno[3,2-b]pyridin-7-yl]-amine;
{2-[6-(2,5-Dimethyl-pyrrol-1-yl)-2-methyl-pyridin-3-yl]-thieno[3,2-b]pyridin-7-yl}-(2-methyl-1H-indol-5-yl)-amine;
(2-[6-(2,5-Dimethyl-pyrrol-1-yl)-5-methyl-pyridin-3-yl]-thieno[3,2-b]pyridin-7-yl}-(2-methyl-1H-indol-5-yl)-amine;
2-{4-Methyl-2-[7-(2-methyl-1H-indol-5-ylamino)-thieno[3,2-b]pyridin-2-yl]-thiazol-5-yl}-propan-2-ol;
(2-Methyl-1H-indol-5-yl)-(2-phenyl-thieno[3,2-b]pyridin-7-yl)-amine;
[2-(3-Methyl-3H-imidazol-4-yl)-thieno[3,2-b]pyridin-7-yl]-phenyl-amine;
6-[7-(2-Methyl-1H-indol-5-ylamino)-thieno[3,2-b]pyridin-2-yl]-pyridine-2-carboxylic acid methyl ester;
2-{6-[7-(2-Methyl-1H-indol-5-ylamino)-thieno[3,2-b]pyridin-2-yl]-pyridin-2-yl}-propan-2-ol;
{6-[7-(2-Methyl-1H-indol-5-ylamino)-thieno[3,2-b]pyridin-2-yl]-pyridin-2-yl}-methanol;
{6-[7-(2-Methyl-1H-indol-5-ylamino)-thieno[3,2-b]pyridin-2-yl]-pyridin-2-yl}-(4-methyl-piperazin-1-yl)-methanone
{6-[7-(2-Methyl-1H-indol-5-ylamino)-thieno[3,2-b]pyridin-2-yl]-pyridin-2-yl}-morpholine-4-yl-methanone;
[2-(1-Methoxymethyl-1H-imidazol-2-yl)-thieno[3,2-b]pyridin-7-yl]-(2-methyl-1H-indol-5-yl)-amine;
(2-Methyl-1H-indol-5-yl)-[2-(2-methyl-1-oxy-pyridin-4-yl)-thieno[3,2-b]pyridin-7-yl]-amine;
(2-Methyl-1H-indol-5-yl)-[2-(1-oxy-pyridin-4-yl)-thieno[3,2-b]pyridin-7-yl]-amine;
(2-Methyl-1H-indol-5-yl)-[2-(2-methyl-pyridin-4-yl)-thieno[3,2-b]pyridin-7-yl]-amine;

and the pharmaceutically acceptable salts, solvates and prodrugs thereof.

9. A compound of the formula 25 or 26

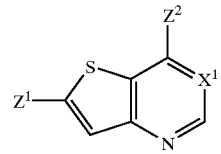

25

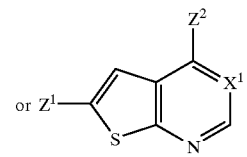

26 or a pharmaceutically acceptable salt or hydrate thereof, wherein:
wherein $X^1$ is CH;
$Z^1$ is halo and $Z^2$ is —$NR^1R^2$; or
$Z^1$ is $R^{11}$ and $Z^2$ is halo; or
$Z^1$ and $Z^2$ are each independently halo;
$R^1$ is H, $C_1$-$C_6$ alkyl or —$C(O)(C_1$-$C_6$ alkyl);
$R^2$ is $C_6$-$C_{10}$ aryl or 5-13 membered heterocyclic, wherein said $R^2$ groups are optionally substituted by 1 to 5 $R^5$ substituents,
each $R^5$ is independently selected from halo, cyano, nitro, trifluoromethoxy, trifluoromethyl, azido, —$C(O)R^8$, —$C(O)OR^8$, —$OC(O)R^8$, —$OC(O)OR^8$, —$NR^6C(O)R^7$, —$C(O)NR^6R^7$, —$NR^6R^7$, —$SO_2NR^6R^7$, $C_1$-$C_6$ alkyl, —$(CH_2)_jO(CH_2)_qNR^6R^7$, —$(CH_2)_jO(CH_2)_qOR^9$, —$(CH_2)_jOR^9$, —$S(O)_j(C_1$-$C_6$ alkyl), —$(CH_2)_t(C_6$-$C_{10}$ aryl), —$(CH_2)_t(5$–$10$ membered heterocyclic), —$(CH_2)_jO(CH_2)_j(C_6$-$C_{10}$ aryl), —$(CH_2)_jO(CH_2)_q(5$–$10$ membered heterocyclic), —$C(O)(CH_2)_t(5$–$10$ membered heterocyclic), $(CH_2)_jNR^7(CH_2)_qNR^6R^7$, —$(CH_2)_jNR^7CH_2C(O)NR^6R^7$, —$(CH_2)_jNR^7(CH_2)_qNR^9C(O)R^8$, —$(CH_2)_jNR^7(CH_2)_tO(CH_2)_qOR^9$, —$(CH_2)_jNR^7(CH_2)_qS(O)_j(C_1$-$C_6$ alkyl), —$(CH_2)_jNR^7(CH_2)_tR^6$, —$SO_2(CH_2)_t(C_6$-$C_{10}$ aryl), and —$SO_2(CH_2)_t$ (5–10 membered heterocyclic), wherein j is an integer ranging from 0 to 2, t is an integer ranging from 0 to 6, q is an integer ranging from 2 to 6, the —$(CH_2)_q$— and —$(CH_2)_t$— moieties of the foregoing $R^5$ groups optionally include a carbon-carbon double or triple bond where t is an integer between 2 and 6, and the alkyl, aryl and heterocyclic moieties of the foregoing $R^5$ groups are optionally substituted by 1 to 3 substituents independently selected from halo, cyano, nitro, trifluoromethyl, azido, —$C(O)R^8$, —$C(O)OR^8$, —OC(O)R$^8$, —OC(O)OR$^8$, —NR$^6$C(O)R$^7$, —C(O)NR$^6$R$^7$, —(CH$_2$)$_t$NR$^6$R$^7$, C$_1$-C$_6$ alkyl, —(CH$_2$)$_t$(C$_6$-C$_{10}$ aryl), —(CH$_2$)$_t$(5–10 membered heterocyclic), —(CH$_2$)$_t$O(CH$_2$)$_q$OR$^9$, and —(CH$_2$)$_t$OR$^9$, wherein t is an integer ranging from 0 to 6 and q is an integer ranging from 2 to 6;

each R$^6$ and R$^7$ is independently selected from H, C$_1$-C$_6$ alkyl, —(CH$_2$)$_t$(C$_6$-C$_{10}$ aryl), —(CH$_2$)$_t$(5–10 membered heterocyclic), —(CH$_2$)$_t$O(CH$_2$)$_q$OR$^9$, and —(CH$_2$)$_t$OR$^9$, wherein t is an integer ranging from 0 to 6 and q is an integer ranging from 2 to 6, and the alkyl, aryl and heterocyclic moieties of the foregoing R$^6$ and R$^7$ groups are optionally substituted by 1 to 3 substituents independently selected from halo, cyano, nitro, trifluoromethyl, azido, —C(O)R$^8$, —C(O)OR$^8$, —OC(O)OR$^8$, —NR$^9$C(O)R$^{10}$, —C(O)NR$^9$R$^{10}$, —NR$^9$R$^{10}$, C$_1$-C$_6$ alkyl, —(CH$_2$)$_t$(C$_6$-C$_{10}$ aryl), —(CH$_2$)$_t$(5–10 membered heterocyclic), —(CH$_2$)$_t$O(CH$_2$)$_q$OR$^9$, and —(CH$_2$)$_t$OR$^9$, wherein t is an integer ranging from 0 to 6 and q is an integer ranging from 2 to 6, with the proviso that where R$^6$ and R$^7$ are both attached to the same nitrogen, then R$^6$ and R$^7$ are not both bonded to the nitrogen directly through an oxygen;

each R$^8$ is independently selected from H, C$_1$-C$_{10}$ alkyl, —(CH$_2$)$_t$(C$_6$-C$_{10}$ aryl), and —(CH$_2$)$_t$(5–10 membered heterocyclic), wherein t is an integer ranging from 0 to 6;

each R$^9$ and R$^{10}$ is independently selected from H and C$_1$-C$_6$ alkyl; and, R$^{11}$ is H, C$_1$-C$_6$ alkyl, —C(O)NR$^6$R$^9$, —C(O)(C$_6$-C$_{10}$ aryl), —(CH$_2$)$_t$(C$_6$-C$_{10}$ aryl, or —(CH$_2$)$_t$(5–10 membered heterocyclic), wherein t is an integer ranging from 0 to 6, wherein said R$^{11}$ groups, other than H, are optionally substituted by tert-butyl-dimethyl-silanyl and 1 to 3 R$^5$ groups.

10. A pharmaceutical composition for the treatment of a hyperproliferative disorder in a mammal which comprises a therapeutically effective amount of a compound of claim 1 and a pharmaceutically acceptable carrier.

11. The pharmaceutical composition of claim 10 wherein said hyperproliferative disorder is cancer.

12. The pharmaceutical composition of claim 11 wherein said cancer is brain, lung, kidney, renal, ovarian, squamous cell, bladder, gastric, pancreatic, breast, head, neck, oesophageal, gynecological, prostate, colorectal or thyroid cancer.

13. The pharmaceutical composition of claim 10 wherein said hyperproliferative disorder is noncancerous.

14. The pharmaceutical composition of claim 13 said disorder is a benign hyperplasia of the skin or prostate.

15. A pharmaceutical composition for the treatment of a hyperproliferative disorder in a mammal which comprises a therapeutically effective amount of a compound of claim 1 in combination with an anti-tumor agent selected from the group consisting of mitotic inhibitors, alkylating agents, anti-metabolites, intercalating antibiotics, enzymes, topoisomerase inhibitors, biological response modifiers, anti-hormones, and anti-androgens, and a pharmaceutically acceptable carrier.

16. The pharmaceutical composition of claim 1 wherein said disease is selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

17. A method of treating a hyperproliferative disorder in a mammal which comprises administering to said mammal a therapeutically effective amount of a compound of claim 1.

18. The method of claim 17 wherein said hyperproliferative disorder is cancer.

19. The method of claim 18 wherein said cancer is brain, lung, squamous cell, renal, kidney, ovarian, bladder, gastric, pancreatic, breast, head, neck, oesophageal, prostate, colorectal, gynecological or thyroid cancer.

20. The method of claim 17 wherein said hyperproliferative disorder is noncancerous.

21. The method of claim 20 wherein said disorder is a benign hyperplasia of the skin or prostate.

22. A method for the treatment of a hyperproliferative disorder in a mammal which comprises administering to said mammal a therapeutically effective amount of a compound of claim 1 in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

23. A method of treating pancreatitis or kidney disease in a mammal which comprises administering to said mammal a therapeutically effective amount of a compound of claim 1.

24. A method for treating a disease related to vasculogenesis or angiogenesis in a mammal which comprises administering to said mammal a therapeutically effective amount of a compound of claim 1.

25. The method of claim 24 wherein said disease is selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

* * * * *